US010682325B2

(12) United States Patent
Comb et al.

(10) Patent No.: US 10,682,325 B2
(45) Date of Patent: *Jun. 16, 2020

(54) COMPOSITIONS AND METHODS FOR THE TREATMENT OF LIVER DISEASES AND DISORDERS ASSOCIATED WITH ONE OR BOTH OF HYPERAMMONEMIA OR MUSCLE WASTING

(71) Applicant: AXCELLA HEALTH INC., Cambridge, MA (US)

(72) Inventors: William Comb, Melrose, MA (US); Sean Carroll, Cambridge, MA (US); Raffi Afeyan, Boston, MA (US); Michael Hamill, Wellesley, MA (US)

(73) Assignee: AXCELLA HEALTH INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/103,207

(22) Filed: Aug. 14, 2018

(65) Prior Publication Data

US 2019/0046487 A1 Feb. 14, 2019

Related U.S. Application Data

(60) Provisional application No. 62/697,772, filed on Jul. 13, 2018, provisional application No. 62/614,214, filed on Jan. 5, 2018, provisional application No. 62/545,362, filed on Aug. 14, 2017.

(51) Int. Cl.
| | |
|---|---|
| *A61K 31/198* | (2006.01) |
| *A61P 1/16* | (2006.01) |
| *A61K 31/17* | (2006.01) |
| *A61K 31/4172* | (2006.01) |
| *A23L 2/00* | (2006.01) |
| *A61K 45/06* | (2006.01) |
| *A61K 9/14* | (2006.01) |
| *A61K 38/03* | (2006.01) |

(52) U.S. Cl.
CPC ............ *A61K 31/198* (2013.01); *A23L 2/00* (2013.01); *A61K 9/145* (2013.01); *A61K 31/17* (2013.01); *A61K 31/4172* (2013.01); *A61K 38/03* (2013.01); *A61K 45/06* (2013.01); *A61P 1/16* (2018.01)

(58) Field of Classification Search
None
See application file for complete search history.

(56) References Cited

U.S. PATENT DOCUMENTS

| | | |
|---|---|---|
| 693,094 A | 2/1902 | Wilson |
| 2,457,820 A | 1/1949 | Howe et al. |
| 3,832,465 A | 8/1974 | Ghadimi |
| 3,950,529 A | 4/1976 | Fischer et al. |
| 3,988,466 A | 10/1976 | Takagi et al. |
| 4,496,703 A | 1/1985 | Steinmetzer |
| 4,871,550 A | 10/1989 | Millman |
| 4,898,879 A | 2/1990 | Madsen et al. |
| 4,908,214 A | 3/1990 | Bobee et al. |
| 5,028,622 A | 7/1991 | Plaitakis |
| 5,034,377 A | 7/1991 | Adibi et al. |
| 5,106,836 A | 4/1992 | Clemens et al. |
| 5,229,136 A | 7/1993 | Mark et al. |
| 5,276,018 A | 1/1994 | Wilmore |
| 5,348,979 A | 9/1994 | Nissen et al. |
| 5,356,873 A | 10/1994 | Mark et al. |
| 5,405,835 A | 4/1995 | Mendy |
| 5,438,042 A | 8/1995 | Schmidl et al. |
| 5,504,072 A | 4/1996 | Schmidl et al. |
| 5,520,948 A | 5/1996 | Kvamme |
| 5,571,783 A | 11/1996 | Montagne et al. |
| 5,576,351 A | 11/1996 | Yoshimura et al. |
| 5,712,309 A | 1/1998 | Finnin et al. |
| 5,719,133 A | 2/1998 | Schmidl et al. |
| 5,719,134 A | 2/1998 | Schmidl et al. |
| 5,723,446 A | 3/1998 | Gray et al. |
| 5,728,678 A | 3/1998 | Trimbo et al. |
| 5,731,290 A | 3/1998 | Schneider |
| 5,733,884 A | 3/1998 | Barbul et al. |
| 5,744,157 A | 4/1998 | Droge |
| 5,756,481 A | 5/1998 | Amal et al. |
| 5,780,039 A | 7/1998 | Greenberg et al. |
| 5,817,329 A | 10/1998 | Gardiner |
| 5,849,335 A | 12/1998 | Ballevre et al. |
| 5,863,906 A | 1/1999 | Amal et al. |
| 5,866,537 A | 2/1999 | Bianchi |

(Continued)

FOREIGN PATENT DOCUMENTS

| | | |
|---|---|---|
| AU | 2014212003 | 9/2015 |
| CN | 1582912 A | 2/2005 |

(Continued)

OTHER PUBLICATIONS

Nutricia Metabolics ("Practical Guide for the Use of Nutricia's TYR Products," downloaded from www.nutricialearningcenter.com/globalassets/pdfs/metabolics/tyr_guidelines on Nov. 20, 2019, publically available on Jan. 11, 2013) (Year: 2013).*
"2016 Nutrica Product Reference Guide" downloaded from nutriciana.com/pages/2016_Canada_PRG.pdf on Nov. 20, 2019 (Year: 2016).*
Jang, C. et al., "A Branched-Chain Amino Acid Metabolite Drives Vascular Fatty Acid Transport and Causes Insulin Resistance," Nat Med., Apr. 2016; 22(4):421-6. doi: 10.1038/nm.4057. Epub Mar. 7, 2016.
Jegatheesan et al., "Hepatic steatosis: a role for citrulline," Curr Opin Clin Nutr Metab Care (2016) vol. 19, No. 5, pp. 360-365.
Jegatheesan et al., "Preventive effects of citrulline on Western diet-induced non-alcoholic fatty liver disease in rats," Br J Nutr (2016) vol. 1161, pp. 191-203.
Jegatheesan, P. et al., "Citrulline and Nonessential Amino Acids Prevent Fructose-Induced Nonalcoholic Fatty Liver Disease in Rats," Nutr, Oct. 2015; 145(10):2273-9.

(Continued)

*Primary Examiner* — Christina Bradley
(74) *Attorney, Agent, or Firm* — Lando & Anastasi, LLP

(57) ABSTRACT

This disclosure provides compositions and methods for treating or preventing liver diseases and disorders with hyperammonemia or muscle wasting in a subject.

42 Claims, 8 Drawing Sheets

(56) References Cited

U.S. PATENT DOCUMENTS

| | | |
|---|---|---|
| 5,977,073 A | 11/1999 | Khaled |
| 6,013,273 A | 1/2000 | Schneider et al. |
| 6,031,000 A | 2/2000 | Nissen et al. |
| 6,051,236 A | 4/2000 | Portman |
| 6,087,398 A | 7/2000 | Goodman |
| 6,096,785 A | 8/2000 | Schneider |
| 6,143,786 A | 11/2000 | Gohman et al. |
| 6,218,420 B1 | 4/2001 | Dioguardi |
| 6,274,612 B1 | 8/2001 | Bryan |
| 6,281,244 B1 | 8/2001 | Schneider et al. |
| 6,328,998 B1 | 12/2001 | Cavazza |
| 6,346,264 B1 | 2/2002 | White |
| 6,376,544 B2 | 4/2002 | Lowry et al. |
| 6,391,332 B1 | 5/2002 | Somerville et al. |
| 6,458,338 B1 | 10/2002 | Adjei et al. |
| 6,521,591 B1 | 2/2003 | Smeets et al. |
| 6,833,350 B2 | 12/2004 | Ballevre et al. |
| 6,864,230 B2 | 3/2005 | Ostrom |
| 6,864,242 B2 | 3/2005 | Ernest |
| 7,300,665 B2 | 11/2007 | Mowrey et al. |
| 7,468,193 B2 | 12/2008 | Schiffrin et al. |
| 7,622,447 B2 | 11/2009 | Lautt et al. |
| 7,645,796 B2 | 1/2010 | Murakami et al. |
| 7,790,688 B2 | 9/2010 | Wolfe et al. |
| 7,794,744 B2 | 9/2010 | Ballevre et al. |
| 7,879,796 B2 | 2/2011 | Edens et al. |
| 7,973,077 B2 | 7/2011 | Dioguardi |
| 8,012,924 B2 | 9/2011 | Abe et al. |
| 8,012,926 B2 | 9/2011 | Abe et al. |
| 8,133,503 B2 | 3/2012 | Laflamme et al. |
| 8,148,356 B2 | 4/2012 | Pavliv |
| 8,173,706 B2 | 5/2012 | Anderson et al. |
| 8,211,944 B2 | 7/2012 | Dioguardi |
| 8,362,080 B2 | 1/2013 | Sekhar |
| 8,383,680 B2 | 2/2013 | Whippie et al. |
| 8,389,471 B2 | 3/2013 | Edens et al. |
| 8,389,576 B2 | 3/2013 | Jalan et al. |
| 8,399,445 B2 | 3/2013 | Pavliv |
| 8,409,592 B2 | 4/2013 | Vidal et al. |
| 8,455,531 B2 | 6/2013 | Kramer et al. |
| 8,466,187 B2 | 6/2013 | Kramer et al. |
| 8,492,439 B2 | 7/2013 | Anderson et al. |
| 8,501,676 B2 | 8/2013 | Hageman |
| 8,524,772 B2 | 9/2013 | Arad et al. |
| 8,536,216 B2 | 9/2013 | Dioguardi |
| 8,648,040 B2 | 2/2014 | Edens et al. |
| 8,653,061 B2 | 2/2014 | Pavliv |
| 8,697,630 B2 | 4/2014 | Hayes et al. |
| 8,703,719 B1 | 4/2014 | Abraham et al. |
| 8,703,725 B2 | 4/2014 | Troup et al. |
| 8,716,249 B2 | 5/2014 | Wolfe et al. |
| 8,722,738 B2 | 5/2014 | Pavliv et al. |
| 8,734,316 B2 | 5/2014 | Schmidt |
| 8,785,498 B2 | 7/2014 | Anderson et al. |
| 8,840,950 B2 | 9/2014 | Hibbert et al. |
| 8,846,759 B2 | 9/2014 | Luiking et al. |
| 8,895,059 B2 | 11/2014 | Vrana et al. |
| 8,946,473 B2 | 2/2015 | Anderson et al. |
| 8,952,045 B1 | 2/2015 | Kramer et al. |
| 8,952,046 B1 | 2/2015 | Kramer et al. |
| 8,952,065 B2 | 2/2015 | Pavliv |
| 8,957,101 B1 | 2/2015 | Kramer et al. |
| 9,017,727 B2 | 4/2015 | Buijsse |
| 9,034,925 B2 | 5/2015 | Anderson et al. |
| 9,066,537 B2 | 6/2015 | Hofman et al. |
| 9,066,953 B2 | 6/2015 | Heaton et al. |
| 9,192,593 B2 | 11/2015 | Hirabayashi et al. |
| 9,198,889 B2 | 12/2015 | Heaton et al. |
| 9,216,162 B2 | 12/2015 | Goldstein |
| 9,233,090 B2 | 1/2016 | Breuille et al. |
| 9,260,379 B2 | 2/2016 | Anderson et al. |
| 9,271,521 B2 | 3/2016 | Okita et al. |
| 9,314,444 B2 | 4/2016 | Szewczyk |
| 9,320,759 B2 | 4/2016 | Pan |
| 9,327,028 B2 | 5/2016 | Pavliv et al. |
| 9,364,463 B2 | 6/2016 | Ferrando et al. |
| 9,375,451 B2 | 6/2016 | Hibbert et al. |
| 9,408,410 B2 | 8/2016 | Zemel et al. |
| 9,408,834 B2 | 8/2016 | Zemel et al. |
| 9,410,963 B2 | 8/2016 | Martin et al. |
| 9,492,498 B2 | 11/2016 | Van Goudoever et al. |
| 9,539,226 B2 | 1/2017 | Lee et al. |
| 9,561,194 B2 | 2/2017 | Schiffrin et al. |
| 9,596,870 B2 | 3/2017 | Zanghi et al. |
| 9,604,909 B2 | 3/2017 | Anderson et al. |
| 9,867,391 B2 | 1/2018 | Dardevet et al. |
| 9,878,004 B2 | 1/2018 | Williams et al. |
| 9,913,818 B2 | 3/2018 | Moinard et al. |
| 10,039,735 B2 | 8/2018 | Jalan et al. |
| 10,045,999 B2 | 8/2018 | Jourdan et al. |
| 10,085,947 B2 | 10/2018 | Shah et al. |
| 10,123,985 B2 | 11/2018 | Sabatini et al. |
| 10,201,513 B2 | 2/2019 | Hamill et al. |
| 10,238,617 B2 | 3/2019 | Hamill et al. |
| 10,471,034 B2 | 11/2019 | Hamill et al. |
| 10,596,136 B2 | 3/2020 | Chakravarthy et al. |
| 2001/0018066 A1 | 8/2001 | Hahn |
| 2001/0041187 A1 | 11/2001 | Hastings et al. |
| 2002/0006907 A1 | 1/2002 | Gardiner et al. |
| 2003/0187049 A1 | 10/2003 | Dioguardi |
| 2004/0023889 A1 | 2/2004 | Gardiner et al. |
| 2004/0067224 A1 | 4/2004 | Ernest |
| 2004/0082659 A1 | 4/2004 | Cooke et al. |
| 2004/0087490 A1 | 5/2004 | Troup et al. |
| 2004/0120983 A1 | 6/2004 | Connolly |
| 2004/0213838 A1 | 10/2004 | Mazer et al. |
| 2005/0020656 A1 | 1/2005 | Horie et al. |
| 2005/0032898 A1 | 2/2005 | Ohtani |
| 2005/0053679 A1 | 3/2005 | Lee et al. |
| 2005/0176827 A1 | 8/2005 | Lee et al. |
| 2005/0197398 A1 | 9/2005 | Sonaka et al. |
| 2006/0002913 A1 | 1/2006 | Gehlsen |
| 2006/0004101 A1 | 1/2006 | Okita et al. |
| 2006/0052455 A1 | 3/2006 | Koga et al. |
| 2006/0159746 A1 | 7/2006 | Troup et al. |
| 2006/0198899 A1 | 9/2006 | Gardiner et al. |
| 2006/0205633 A1 | 9/2006 | Nishitani et al. |
| 2007/0060651 A1 | 3/2007 | Larson et al. |
| 2007/0142469 A1 | 6/2007 | Thomas et al. |
| 2007/0197647 A1 | 8/2007 | Kumada et al. |
| 2007/0212447 A1 | 9/2007 | Nogata et al. |
| 2007/0243211 A1 | 10/2007 | Jaffe |
| 2007/0270355 A1 | 11/2007 | Garcia et al. |
| 2007/0286909 A1 | 12/2007 | Smith et al. |
| 2008/0038321 A1 | 2/2008 | Tsuji et al. |
| 2008/0102137 A1 | 5/2008 | Guffey |
| 2008/0114065 A1 | 5/2008 | Pacioretty et al. |
| 2008/0114067 A1 | 5/2008 | Yamamoto |
| 2008/0161398 A1 | 7/2008 | Verlaan et al. |
| 2008/0182811 A1 | 7/2008 | Ohsu et al. |
| 2008/0268038 A1 | 10/2008 | Wolfe |
| 2009/0011077 A1 | 1/2009 | Schiffrin et al. |
| 2009/0018196 A1 | 1/2009 | Bjork et al. |
| 2009/0048153 A1 | 2/2009 | Varma et al. |
| 2009/0105123 A1 | 4/2009 | Tisdale et al. |
| 2009/0170786 A1 | 7/2009 | Greenberg |
| 2009/0181903 A1 | 7/2009 | Wolfe et al. |
| 2009/0186098 A1 | 7/2009 | Briceno |
| 2009/0203606 A1 | 8/2009 | Wolfe et al. |
| 2009/0306209 A1 | 12/2009 | Daugherty et al. |
| 2010/0021573 A1 | 1/2010 | Gonzalez et al. |
| 2010/0092610 A1 | 4/2010 | Haschke et al. |
| 2010/0104548 A1 | 4/2010 | Rossetti et al. |
| 2010/0119692 A1 | 5/2010 | Hamman et al. |
| 2010/0152107 A1 | 6/2010 | Le-Henand et al. |
| 2010/0233304 A1 | 9/2010 | Pan |
| 2010/0267831 A1 | 10/2010 | Kobayashi et al. |
| 2010/0280119 A1 | 11/2010 | Anderson et al. |
| 2011/0077198 A1 | 3/2011 | Tisdale et al. |
| 2011/0081329 A1 | 4/2011 | Smith et al. |
| 2011/0229447 A1 | 9/2011 | Schiffrin et al. |
| 2011/0257236 A1 | 10/2011 | Koyama et al. |
| 2011/0269678 A1 | 11/2011 | Breuille et al. |
| 2011/0294727 A1 | 12/2011 | Hibbert et al. |

(56) References Cited

U.S. PATENT DOCUMENTS

| | | |
|---|---|---|
| 2012/0020947 A1 | 1/2012 | Shirazi et al. |
| 2012/0157526 A1 | 6/2012 | Jalan et al. |
| 2012/0178672 A1 | 7/2012 | Wolfe et al. |
| 2012/0195873 A1 | 8/2012 | Miller et al. |
| 2012/0208885 A1 | 8/2012 | Anderson et al. |
| 2012/0251512 A1 | 10/2012 | Farmer et al. |
| 2012/0270860 A1 | 10/2012 | Yoon et al. |
| 2012/0315354 A1 | 12/2012 | Palzer et al. |
| 2012/0329846 A1 | 12/2012 | Matsumoto et al. |
| 2013/0143836 A1* | 6/2013 | Yue .............. A61K 31/197 514/52 |
| 2013/0209433 A1 | 8/2013 | Rossetti et al. |
| 2013/0210715 A1 | 8/2013 | Greenberg et al. |
| 2013/0211135 A1 | 8/2013 | Anderson et al. |
| 2013/0225510 A1 | 8/2013 | Greenberg |
| 2013/0296429 A1 | 11/2013 | Anderson et al. |
| 2014/0004205 A1 | 1/2014 | Satyaraj |
| 2014/0037601 A1 | 2/2014 | Greenberg |
| 2014/0093609 A1 | 4/2014 | Roy et al. |
| 2014/0135396 A1 | 5/2014 | Goessling et al. |
| 2014/0147549 A1 | 5/2014 | Jeukendrup et al. |
| 2014/0155448 A1 | 6/2014 | Kato et al. |
| 2014/0249078 A1 | 9/2014 | Breuille et al. |
| 2014/0255511 A1 | 9/2014 | Dardevet et al. |
| 2014/0271984 A1 | 9/2014 | Pouteau et al. |
| 2014/0288327 A1 | 9/2014 | Anderson et al. |
| 2014/0294788 A1 | 10/2014 | Bailey et al. |
| 2014/0295002 A1 | 10/2014 | Heaton et al. |
| 2014/0303099 A1 | 10/2014 | Wolfe et al. |
| 2014/0342040 A1 | 11/2014 | Miller et al. |
| 2014/0343112 A1 | 11/2014 | Ferrando et al. |
| 2014/0356479 A1 | 12/2014 | Serrano |
| 2014/0357553 A1 | 12/2014 | Smola et al. |
| 2014/0357576 A1 | 12/2014 | Breuille et al. |
| 2015/0118351 A1 | 4/2015 | Haschke et al. |
| 2015/0133684 A1 | 5/2015 | Anderson et al. |
| 2015/0223501 A1 | 8/2015 | Huynh-Ba et al. |
| 2015/0246066 A1 | 9/2015 | Nelson |
| 2015/0251990 A1 | 9/2015 | Anderson et al. |
| 2015/0313262 A1 | 11/2015 | Zanghi et al. |
| 2016/0027657 A1 | 1/2016 | Shi et al. |
| 2016/0051814 A1 | 2/2016 | Arigoni et al. |
| 2016/0067201 A1 | 3/2016 | Zemel et al. |
| 2016/0128960 A1 | 5/2016 | Faure et al. |
| 2016/0158305 A1 | 6/2016 | Thomson |
| 2016/0243202 A1 | 8/2016 | Vincent |
| 2016/0302451 A1 | 10/2016 | Hudnall |
| 2016/0338982 A1 | 11/2016 | Ruettimann et al. |
| 2016/0339078 A1 | 11/2016 | Hamill et al. |
| 2016/0367509 A1 | 12/2016 | Pan |
| 2017/0027897 A1 | 2/2017 | Wang et al. |
| 2017/0042189 A1 | 2/2017 | Pibarot et al. |
| 2017/0079897 A1 | 3/2017 | Minus |
| 2017/0079935 A1 | 3/2017 | Schiffrin et al. |
| 2017/0135973 A1 | 5/2017 | Wang et al. |
| 2017/0196944 A1 | 7/2017 | Portman |
| 2017/0360734 A1 | 12/2017 | Blum |
| 2017/0368026 A1 | 12/2017 | Faure et al. |
| 2017/0368027 A1 | 12/2017 | Blum-Sperisen et al. |
| 2017/0370910 A1 | 12/2017 | Rezzi et al. |
| 2018/0015122 A1 | 1/2018 | Villamil Torres et al. |
| 2018/0021278 A1 | 1/2018 | Faure et al. |
| 2018/0036270 A1 | 2/2018 | Aw et al. |
| 2018/0044281 A1 | 2/2018 | Anderson et al. |
| 2018/0125926 A1 | 5/2018 | Williams et al. |
| 2018/0161293 A1 | 6/2018 | Jalan et al. |
| 2018/0169044 A1 | 6/2018 | Hamill et al. |
| 2018/0169045 A1 | 6/2018 | Hamill et al. |
| 2018/0169046 A1 | 6/2018 | Hamill et al. |
| 2018/0169047 A1 | 6/2018 | Hamill et al. |
| 2018/0200192 A1 | 7/2018 | Gammans |
| 2018/0207118 A1 | 7/2018 | Hamill et al. |
| 2018/0207119 A1 | 7/2018 | Hamill et al. |
| 2018/0221320 A1 | 8/2018 | Rose et al. |
| 2018/0296516 A1 | 10/2018 | Hamill et al. |
| 2019/0000866 A1 | 1/2019 | Siegel et al. |
| 2019/0046486 A1 | 2/2019 | De Rienzo et al. |
| 2019/0046487 A1 | 2/2019 | Comb et al. |
| 2019/0105294 A1 | 4/2019 | Hamill et al. |
| 2019/0388374 A1 | 12/2019 | Hanlon et al. |
| 2019/0388375 A1 | 12/2019 | Hanlon et al. |
| 2019/0388376 A1 | 12/2019 | Carroll et al. |
| 2019/0388377 A1 | 12/2019 | Hamill et al. |

FOREIGN PATENT DOCUMENTS

| | | |
|---|---|---|
| CN | 101049500 A | 10/2007 |
| CN | 101332209 B | 12/2010 |
| CN | 101214050 B | 8/2011 |
| CN | 101664384 | 9/2011 |
| CN | 102327259 A | 1/2012 |
| CN | 102961377 A | 3/2013 |
| CN | 105092753 A | 11/2015 |
| CN | 106632605 A | 5/2017 |
| CN | 107242552 A | 10/2017 |
| CN | 108041501 A | 5/2018 |
| CN | 108524453 A | 9/2018 |
| EP | 0147699 A2 | 7/1985 |
| EP | 0656178 | 7/1995 |
| EP | 0827744 A2 | 3/1998 |
| EP | 0882451 A1 | 12/1998 |
| EP | 0891719 A1 | 1/1999 |
| EP | 1004302 A2 | 5/2000 |
| EP | 1025844 A1 | 8/2000 |
| EP | 1083915 B1 | 3/2001 |
| EP | 1108429 A2 | 6/2001 |
| EP | 0764405 B1 | 11/2002 |
| EP | 1399139 A2 | 3/2004 |
| EP | 1541141 A1 | 6/2005 |
| EP | 1552826 A1 | 7/2005 |
| EP | 1637163 A1 | 3/2006 |
| EP | 0983726 B1 | 10/2006 |
| EP | 0674902 B1 | 4/2007 |
| EP | 1774966 A1 | 4/2007 |
| EP | 1774973 A1 | 4/2007 |
| EP | 1938813 A1 | 7/2008 |
| EP | 2060914 A2 | 5/2009 |
| EP | 1374863 B1 | 9/2009 |
| EP | 2095728 A2 | 9/2009 |
| EP | 1085862 B1 | 1/2011 |
| EP | 2091526 B1 | 5/2011 |
| EP | 2340725 A1 | 7/2011 |
| EP | 2413924 B1 | 2/2012 |
| EP | 2440200 B1 | 4/2012 |
| EP | 2196203 B1 | 8/2012 |
| EP | 2601951 A1 | 6/2013 |
| EP | 2327315 B1 | 10/2013 |
| EP | 1549299 B1 | 8/2014 |
| EP | 2792354 A2 | 10/2014 |
| EP | 2799067 A1 | 11/2014 |
| EP | 2865382 A1 | 4/2015 |
| EP | 2968241 B1 | 1/2016 |
| EP | 2977418 A1 | 1/2016 |
| EP | 2786750 B1 | 6/2016 |
| EP | 2327316 B1 | 11/2016 |
| EP | 2574333 B1 | 1/2017 |
| EP | 2440217 B1 | 12/2017 |
| EP | 3263100 A1 | 1/2018 |
| EP | 3298908 A2 | 3/2018 |
| GB | 1034358 A | 6/1966 |
| GB | 2029220 B | 3/1983 |
| GB | 2113524 B | 7/1985 |
| JP | 2003238401 A | 8/2003 |
| JP | 2007055992 A | 3/2007 |
| JP | 2011116775 A | 6/2011 |
| JP | 2011132174 A | 7/2011 |
| JP | 5067160 B2 | 11/2012 |
| JP | 5100033 B2 | 12/2012 |
| JP | 5516654 B2 | 6/2014 |
| JP | 6110444 B2 | 4/2017 |
| KR | 20060124732 A | 12/2006 |
| KR | 100970664 B1 | 7/2010 |
| WO | 1983000085 A1 | 1/1983 |
| WO | 9414458 A1 | 7/1994 |

(56) References Cited

FOREIGN PATENT DOCUMENTS

| | | |
|---|---|---|
| WO | 9804254 A1 | 2/1998 |
| WO | 9854985 A1 | 12/1998 |
| WO | 2001026642 A2 | 4/2001 |
| WO | 2001056402 A2 | 8/2001 |
| WO | 2002002092 A2 | 1/2002 |
| WO | 2003103582 A2 | 12/2003 |
| WO | 2004058242 A1 | 7/2004 |
| WO | 2005017094 A2 | 2/2005 |
| WO | 2005021596 A2 | 3/2005 |
| WO | 2005084323 A2 | 9/2005 |
| WO | 2005102301 A2 | 11/2005 |
| WO | 2005110124 A1 | 11/2005 |
| WO | 2006083381 A2 | 8/2006 |
| WO | 2006105112 A2 | 10/2006 |
| WO | 2007002365 A2 | 1/2007 |
| WO | 2007056176 A2 | 5/2007 |
| WO | 2007064618 A1 | 6/2007 |
| WO | 2009109460 A1 | 9/2009 |
| WO | 2010115055 A1 | 10/2010 |
| WO | 2010144498 A2 | 12/2010 |
| WO | 2011030104 A1 | 3/2011 |
| WO | 2011044230 A9 | 8/2011 |
| WO | 2011097273 A1 | 8/2011 |
| WO | 2012005582 A1 | 1/2012 |
| WO | 2012048043 A1 | 4/2012 |
| WO | 2012088075 A1 | 6/2012 |
| WO | 2012092035 A1 | 7/2012 |
| WO | 2012097061 A1 | 7/2012 |
| WO | 2012143402 A1 | 10/2012 |
| WO | 2013006658 A1 | 1/2013 |
| WO | 2013028547 A1 | 2/2013 |
| WO | 2013108871 A1 | 7/2013 |
| WO | 2013188258 A1 | 12/2013 |
| WO | 2014172341 A1 | 10/2014 |
| WO | 2015015149 A1 | 2/2015 |
| WO | 2015048333 A2 | 4/2015 |
| WO | 2015048340 A2 | 4/2015 |
| WO | 2015048342 A2 | 4/2015 |
| WO | 2015048345 A2 | 4/2015 |
| WO | 2015048346 A2 | 4/2015 |
| WO | 2015048348 A2 | 4/2015 |
| WO | 2015061607 A1 | 4/2015 |
| WO | 2015131152 A1 | 9/2015 |
| WO | 2015161448 A1 | 10/2015 |
| WO | 2016003263 A1 | 1/2016 |
| WO | 2016058919 A1 | 4/2016 |
| WO | 2016088078 A1 | 6/2016 |
| WO | 2016094316 A1 | 6/2016 |
| WO | 2016097299 A1 | 6/2016 |
| WO | 2016116580 A1 | 7/2016 |
| WO | 2016121829 A1 | 8/2016 |
| WO | 2016128576 A1 | 8/2016 |
| WO | 2016172112 A1 | 10/2016 |
| WO | 2017001590 A1 | 1/2017 |
| WO | 2017031131 A1 | 2/2017 |
| WO | 2017033272 A1 | 3/2017 |
| WO | 2017053613 A1 | 3/2017 |
| WO | 2017083758 A1 | 5/2017 |
| WO | 2017085138 A1 | 5/2017 |
| WO | 2017107863 A1 | 6/2017 |
| WO | 2017127333 A1 | 7/2017 |
| WO | 2017193154 A1 | 11/2017 |
| WO | 2017202939 A1 | 11/2017 |
| WO | 2018013873 A1 | 1/2018 |
| WO | 2018117954 A1 | 6/2018 |
| WO | 2018118941 A1 | 6/2018 |
| WO | 2018118957 A1 | 6/2018 |
| WO | 2019036442 A1 | 2/2019 |
| WO | 2019036471 A1 | 2/2019 |

OTHER PUBLICATIONS

Jegatheesan, P. et al., "Effect of Specific Amino Acids on Hepatic Lipid Metabolism in Fructose-Induced Non-Alcoholic Fatty Liver Disease," (2016) Clinical Nutrition, 35: 175-182.

Jennings et al., "Associations between branched chain amino acid intake and biomarkers of adiposity and mardiometabolic health independent of genetic factors: A twin study," Intl J Cardiology (2016) vol. 223, pp. 992-998.

Jha et al., "Network Integration of Parallel Metabolic and Transcriptional Data Reveals Metabolic Modules that Regulate Macrophage Polarization," Immunity (2015) vol. 42, pp. 419-430.

Jiao, J. et al., "Chronic leucine Supplementation Improves Lipid Metabolism in C57BL/6J Mice Fed with a High-Fat/Cholesterol Diet," Food Nutr Res., Sep. 9, 2016; 60:31304. doi: 10.3402/fnr.v60.31304. eCollection 2016.

Jobgen, W. et al., "Dietary L-Arginine Supplementation Reduces White Fat Gain and Enhances Skeletal Muscle and Brown Fat Masses in Diet-Induced Obese Rats," J Nutr, Feb. 2009; 139(2):230-7.

Kakazu et al., "Plasma amino acids imbalance in cirrhotic patients disturbs the tricarboxylic acid cycle of dendritic cell," Sci Rep (2013) vol. 3, Article 3459, 8 pages.

Kakumitsu, S. et al., "Effects of L-Arginine on the Systemic, Mesenteric, and Hepatic Circulation in Patients With Cirrhosis," Hepatology, Feb. 1998; 27(2):377-82.

Kanda et al., "Post-exercise whey protein hydrolysate supplementation induces a greater increase in muscle protein synthesis than its constituent amino acid content," Br J Nutr (2013) vol. 110, pp. 981-987.

Katsanos et al., "Whey protein ingestion in elderly results in greater muscle protein accrual than ingestion of its constituent essential amino acid content," Nutr Res (2008) vol. 28, No. 10, pp. 651-658.

Kawaguchi et al., "Branched-Chain Amino Acids Prevent Hepatocarcinogenesis and Prolong Survival of Patients With Cirrhosis," Clinical Gastroenterology and Hepatology (2014) vol. 12, pp. 1012-1018.e1.

Kawaguchi et al., "Effects of Oral Branched-Chain Amino Acids on Hepatic Encephalopathy and Outcome in Patients With Liver Cirrhosis," Nutr Clin Pract (2013) vol. 28, No. 5, pp. 580-588.

Kawaguchi et aL, "Wheat-bran autolytic peptides containing a branched-chain amino acid attenuate non-alcoholic steatohepatitis via the suppression of oxidative stress and the upregulation ofAMPJ/ACC in high-fat diet-fed mice," International J Molecular Medicine (2017) vol. 39, pp. 407-414.

Kelleher et al., "The mTORC1 signaling repressors REDD1/2 are rapidly induced and activation of p70S6K1 by leucine is defective in skeletal muscle of an immobilized rat hindlimb," Am J Physiol Endocrinol Metab (2013) vol. 304, pp. E229-E236.

Kerksick et al., "The Antioxidant Role of Glutathione and N-Acetyl-Cysteine Supplements and Exercise-Induced Oxidative Stress," Journal of the International Society of Sports Nutrition (2005), vol. 2, No. 2, pp. 38-44.

Khoshbaten, M. et al., "N-Acetylcysteine Improves Liver Function in Patients with Non-Alcoholic Fatty Liver Disease," Hepat Mon, 2010 Winter; 10(1):12-6. Epub Mar. 1, 2010.

Kim et al., "Acetyl CoA Carboxylase Inhibition Reduces Hepatic Steatosis but Elevates Plasma Triglycerides in Mice and Humas: A Bedside to Bench Investigation," Cell Metabolism (2017) vol. 26, pp. 394-406.

Kim et al., "Quantity of dietary protein intake, but not pattern of intake, affects net protein balance primarily through differences in protein synthesis in older adults," Am J Physiol Endocrinol Metab (2015) vol. 308, No. 1, pp. E21-E28.

Kinny-Köster et al., "Plasma Amino Acid Concentrations Predct Mortality in Patients with End-Stage Liver Disease," PLOS One (2016) vol. 11, No. 7, Article e0159205, 13 pages.

Kircheis et al., "Therapeutic Efficacy of L-Ornithine-L-Aspartate Infusions in Patients With Cirrhosis and Hepatic Encephalopathy: Results of a Placebo-Controlled, Double-Blind Study," Hepatology (1997) vol. 25, pp. 1351-1360.

Kitajima et al., "Supplementation with branched-chain amino acids ameliorates hypoalbuminemia, prevents sarcopenia, and reduces fat accumulation in the skeletal muscles of patients with liver cirrhosis," J Gastroenterol (2017) doi 10.1007/s00535-017-1370-x, 11 pages.

(56) References Cited

OTHER PUBLICATIONS

Knudsen et al., "L-leucine methyl ester stimulates insulin secretion and islet glutamate dehydrogenase," Am J Physiol (1983) vol. 245, pp. E338-E346.

Krenitsky, "Nutrition Update in Hepatic Failure," Practical Gastroenterology (2014) pp. 47-55.

Kumar et al., "Ammonia lowering reverses sarcopenia or cirrhosis by restoring skeletal muscle proteostasis," Hepatol (2017) vol. 65, No. 6, pp. 2045-2058.

Kuwahata et al., "Supplementation with branched-chain amino acids attenuates hepatic apoptosis in rats with chronic liver disease," Nutrition Research (2012) vol. 32, pp. 522-529.

Kwanten et al., "Role of autophagy in the pathophysiology of nonalcoholic fatty liver disease: A controversial issue," World J Gastroenterol (2014) vol. 20, Issue 23, pp. 7325-7338.

Le Plénier et al., "Citrulline directly modulates muscle protein syntheses via the PI3K/MAPK/4E-BP1 pathway in a malnourished state: evidence from in vivo, ex vivo, and in vitro studies," Am J Physiol Endocrinol Metab (2017) vol. 312, pp. E27-E36.

Li et al., "A Novel Dual Eigen-Analysis of Mouse Multi-Tissues' Expression Profiles Unveils New Perspectives into Type 2 Diabetes," Sci Rep (2017) vol. 7, Article 5044, 12 pp.

Li et al., "Leucine supplementation increases SIRT1 expression and prevents mitochondrial dysfunction and metabolic disorders in high-fat diet-induced obese mice," Am J Endocrinol Metab (2012) vol. 303, pp. E1234-E1244.

Li, T. et al., "Branched-Chain Amino Acids Alleviate Nonalcoholic Steatohepatitis in Rats," Appl Physiol Nutr Metab., Aug. 2013; 38(8):836-43. doi: 10.1139/apnm-2012-0496. Epub Mar. 8, 2013.

Liu et al., "Gene-metabolite network analysis in different nonalcoholic fatty liver disease phernotypes," Experimental & Molecular Medicine (2017) vol. 49, e283, 9 pp.

Liu et al., "Leucine Supplementation Differently Modulates Branched-Chain Amino Acid Catabolism, Mitochondrial Function and Metabolic Profiles at the Different Stages of Insulin Resistance in Rats on High-Fat Diet," Nutrients (2017) vol. 9, Article 565, 20 pp.

Liu, B. et al., "Glutamine Attenuates Obstructive Cholestasis in Rats Via famesoid X Receptor-Mediated Regulation of Bsep and Mrp2," Can J Physiol Pharmacol, Feb. 2017; 95(2):215-223. doi: 10.1139/cjpp-2016-0389. Epub Oct. 5, 2016.

Lucotti, P. et al., "Beneficial Effects of a Long-Term Oral L-Arginine Treatment Added to a Hypocaloric Diet and Exercise Training Program in Obese, Insulin-Resistant Type 2 Diabetic Patients," (2006) Am J Physiol Endocrinol Metab, 291: E906-E912.

Luiking et al., "Arginine de novo and nitric oxide production in disease states," Am J Physiol Endocrinol Metab (2012) vol. 303, pp. E1177-E1189.

Lynch et al., "Branched-chain amino acids in metabolic signalling and insulin resistance," Nat Rev Endocrinol (2014) vol. 10, No. 12, pp. 723-736.

Lynch et al., "Tissue-specific effects of chronic dietary leucine and norleucine supplementation on protein synthesis in rats," Am J Physiol Endocrinol Metab (2002) vol. 283, pp. E824-E835.

Macotela et al., "Dietary Leucine—An Environmental Modifier of Insulin Resistance Acting on Multiple Levels of Metabolism," PLoS ONE (2011) vol. 6, e21187, 13 pp.

Madden et al., "Ten Amino Acids Essential for Plasma Protein Production Effective Orally or Intravenously," J Exper Med (1943) vol. 77, No. 3, pp. 277-295.

Maddrey, W.C., "Branched Chain Amino Acid Therapy in Liver Disease (abstract only)," J Am Coll Nutr. 1985;4(6):639-50.

Mager, D.R. et al., "Branched-Chain Amino Acid Needs in Children with Mild-to-Moderate Chronic Cholestatic Liver Disease," J. Nutr, 136: 133-139, 2006.

Malaguarnera et al., "Branched chain amino acids supplemented with L-acetylcamitine versus BCAA treatmentin hepatic coma: a randomized and controlled double blind study," Eur J Gastroenterol Hepatol (2009) vol. 21, No. 7, pp. 762-770, Abstract Only.

Mansoor et al., "Effect of an enteral diet supplemented with a specific protein blend of amino acid on plasma and muscle protein synthesis in ICU patients," Clinical Nutrition (2007) vol. 26, pp. 30-40.

Marchesini et al., "Branched-Chain Amino Acid Supplementation in Patients with Liver Diseases," J Nutr (2005) vol. 135, pp. 1596S-1601S.

Marchesini et al., "Nutritional Supplementation With Branched-Chain Amino Acids in Advanced Cirrhosis: A Double-Blind, Randomized Tial," Gastroenterology (2003) vol. 124, No. 7, pp. 1792-1801.

Mardinoglu et al., "Personal model-assisted identification of NAD+ and glutathione metabolism as intervention target in NAFLD," Mol Sys Biol (2017) vol. 13, Article 916, 17 pages.

Marra et al., "Lipotoxicity and the gut-liver axis in NASH pathogenesis," Journal of Hepatology (2017), doi: 10.1016/j.ihep.2017.11.014, 44 pp.

Marra et al., "Roles for Chemokines in Liver Disease," Gastroenterology (2014) vol. 147, pp. 577-594.

Martin et al., "Leucine elicits myotube hypertrophy and enhances maximal contractile force in tissue engineered skeletal muscle in vitro," J Cell Physiol (2017) vol. 232, pp. 2788-2797.

Martin et al., "Whey Proteins Are More Efficient than casein in the Recovery of Muscle Functional Properties following a Casting Induced Muscle Atrophy," PLOS One (2013) vol. 8, No. 9, Article e75408, 8 pp.

Massafra et al., "Famesoid X Receptor Activation Promotes Hepatic Amino Acid Catabolism and Ammonium Clearance in Mice," Gastroenterology (2017) doi: 10.1053/j.gastro.2017.01.014, 48 pp.

Matoori et al., "Recent advances in the treatment of hyperammonemia," Adv Drug Deliv Rev (2015) doi: 10.1016/j.addr.2015.04.009, 14 pages.

McCarty et al., "The cardiometabolic benefits of glycine: Is glycine an 'antidote' to dietary fructose," Open Heart (2014) vol. 1, Article e000103, 9 pp.

McCarty, "Supplementation with Phycocyanobilin, Citrulline, Taurine, and Supranutritional Doses of Folic Acid and Biotin-Potential for Preventing or Slowing the Progression of Diabetic Complications," Healthcare (2017) vol. 5, Article 15, 28 pp.

McCormack et al., "Circulating Branched-chain Amino Acid Concentrations Are Associated with Obesity and Future Insulin Resistance in Children and Adolescents," Pediatr Obes (2013) vol. 8, No. 1, pp. 52-61.

McCullough et al., "Stable isotope-based flux studies in nonalcoholic fatty liver disease," Pharmacology & Therapeutics (2017) doi: 10.1016/j.pharmthera.2017.07.008, 12 pp.

McKnight et al., "Beneficial effects of L-arginine on reducing obesity: potential mechanisms and important implications for human health," Amino Acids (2010) vol. 39, pp. 349-357.

Meex et al., "Hepatokines: linking nonalcoholic fatty liver disease and insulin resistance," Nat Rev Endocrinol (2017) doi: 10.1038/nrendo.2017.56, 12 pp.

Miczke A. et al., "Effect of L-Arginine Supplementation on Insulin Resistance and Serum Adiponectin Concentration in Rats with Fat Diet," (2015) Int J Clin Exp Med, 2015; 8(7); 10358-66.

Mikulski et al., "Effects of supplementation with branched chain amino acids and ornithine aspartate on plasma ammonia and central fatigue during exercise in healthy men," Folia Neuropathol (2015) vol. 53, No. 4, pp. 377-386.

Mirmiran, P. et al., "The Association of Dietary L-Arginine Intake and Serum Nitric Oxide Metabolites in Adults: A Population-Based Study," Nutrients, May 20, 2016; 8(5). pii: E311.

Mittal et al., "A randomized controlled trial comparing lactulose, probiotics, and L-ornithine L-aspartate in treatment of minimal hepatic encephalopathy," Eur J Gastroenterol Hepatol (2011) vol. 23, pp. 725-732.

Moinard et al., "Arginine behaviour after arginine or citrulline administration in older subjects," Br J Nutr (2016) vol. 115, pp. 399-404.

Moinard et al., "Dose-ranging effects of citrulline administration on plasma amino acids and hormonal patterns in healthy subjects: the Citrudose pharmacokinetic study," Br J Nutr (2007) vol. 99, pp. 855-862.

(56) References Cited

OTHER PUBLICATIONS

Monti, L.D. et al., "Beneficial Role of L-Arginine in Cardiac Matrix Remodelling in Insulin Resistant Rats," (2008)—European Journal of Clinical Investigation, vol. 38(11):849-56.
Monti, L.D. et al., "Effect of a Long-Term Oral L-Arginine Supplementation on Glucose Metabolism: a Randomized, Double-Blind, Placebo-Controlled Trial," (2012) Diabetes, Obesity and Metabolism 14: 893-900, 2012.
Mordier et al., "Leucine limitation induces autophagy and activation of lysosome-dependent proteolysis in C2C12 myotubes through a mammalian target of rapamycin-independent signaling pathway," J Biol Chem (2000) vol. 275, pp. 29900-29906.
Morgan et al., "Plasma amino-acid patterns in liver disease," Gut (1982) vol. 23, pp. 362-370.
Moriwaki et al., Branched-chain amino acids as a protein- and energy-source in liver cirrhosis, Biochemical and Biophysical Research Communications (2004) vol. 313, pp. 405-409.
Murgas Torrazza et al., "Leucine supplementation of a low-protein meal increases skeletal muscle and visceral tissue protein synthesis in neonatal pigs by stimulating mTOR-dependent translation initiation," J Nutr (2010) vol. 140, pp. 2145-2152.
Murphy et al., "Leucine supplemmentation enhances integrative myofibrillar protein syntesis in free-living older men consuming lower- and higher-protein diets: a parallel-group crossover study," Am J Clin Nutr (2016) vol. 104, pp. 1594-1606.
Musso et al., "Non-alcoholic steatohepatitis: emerging molecular targets and therapeutic strategies," Nat Rev Drug Discovery (2016) vol. 15, pp. 249-274.
Muto et al., "Overweight and obesity increase the risk for liver cancer in patients with liver cirrhosis and long-term oral supplementation with branched-chain amino acid granules inhibits liver carcinogenesis in heavier patients with liver cirrhosis," Hepatology Research (2006) vol. 35, pp. 204-214.
Muto, Y, et al., "Effect of Oral Branched-Chain Amino Acid Granules on Event-Free Survival in Patients with Liver Cirrhosis," Clin Gastroenterol Hepatol., Jul. 2005; 3(7):705-13.
Naganuma et al., "Effect of the Medical Walking and Leucine Enriced Amino acid Containing Food for Female Non-Alcoholic Fatty Liver Disease: Randomized Controlled Trial," Clinical Nutrition (2016) vol. 35, p. S62, Poster SUN-P050.
Najmi et al., "Effect of l-ornithinel l-aspartate against thioacetamide-induced hepatic damage in rats," Indian J Pharmacol (2010) vol. 42, No. 6, pp. 384-387.
Nakanishi et al., "Treatment with L-Valine Ameliorates Liver Fibrosis and Restores Thrombopoiesis in Rats Exposed to Carbon Tetrachloride," Tohoku J Exp Med (2010) vol. 221, pp. 151-159.
Nakaya et al., "BCAA-enriched snack improves nutritional state of cirrhosis," Nutrition (2007) vol. 23, pp. 113-120.
Nakaya et al., "Severe catabolic state after prolonged fasting in cirrhotic patients: effect of oral branched-chain amino-acid-enriched nutrient mixture," J Gastroenterol (2002) vol. 37, pp. 531-536.
Nanji et al., "Arginine Reverses Ethanol-Induced Inflammatory and Fibrotic Changes in Liver Despite Continued Ethanol Administration," J Pharmacol Exp Ther (2010) vol. 299, No. 3, pp. 832-839.
Ndraha et al., "The Effect of L-ornithine L-aspartate and Branch Chain Amino Acids on Encephalopathy and Nutritional Status in Liver Cirrhosis with Malnutrition," Acta Med Indones-Indones J Intern Med (2011) vol. 43, No. 1, pp. 18-22.
Newgard, C.B. et al., "A Branched-Chain Amino Acid-Related Metabolic Signature that Differentiates Obese and Lean Humans and Contributes to Insulin Resistance," Cell Metab., Apr. 2009; 9(4):311-26. doi: 10.1016/j.cmet.2009.02.002.
Nicastro et al., "An overview of the therapeutic effects of leucine supplementation on skeletal muscle under atrophic conditions," Amino Acids (2011) vol. 40, pp. 287-300.
Nielsen, "Systems Biology of Metabolism: A Driver for Developing Personalized and Precision Medicine," Cell Metabolism (2017) vol. 25, pp. 572-579.

Nilsson et al., "Metabolic effects of amino acid mixtures and whey protein in healthy subjects: studies using glucose-equivalent drinks," Am J Clin Nutr (2007) vol. 85, pp. 996-1004.
Nishiguchi et al., "Effect of oral supplementation with branched-chain amino acid granules in the early stage of cirrhosis," Hepatology Research (2004) vol. 30, Supplement, pp. 36-41, Abstract Only.
Nishikata et al., "Dietary lipid-dependent regulation of de novo lipogenesis and lipid partitioning by ketogenic essential amino acids in mice," Nutrition and Diabetes (2011) vol. 1, e5, 12 pp.
Nishitani et al., "Pharmacological activities of branched-chain amino acids: augmentation of albumin synthesis in liver and improvement of glucose metabolism in skeletal muscle," Hepatology Research (2004) vol. 30, Supplement, pp. 19-24, Abstract Only.
Nissen et al., "Effect of leucine metabolite b-hydroxy-b-methylbutyrate on muscle metabolism during resistance-exercise training," J Applied Physiology (1996) vol. 81, pp. 2095-2104.
Nissim et al., "Agmatine Stimulates Hepatic Fatty Acid Oxidation: A Possible Mechanism for Up-Regulation of Ureagenesis," J Biol Chem (2006) vol. 281, No. 13, pp. 8486-8496.
Nissim, I et al., "The Molecular and Metabolic Influence of Long Term Agmatine Consumption," (2014)—The Journal of Biological Chemistry, vol. 289, No. 14, pp. 9710-9729.
Noguchi et al., "Effect of Anaplerotic Fluxes and Amino Acid Availability on Hepatic Lipoapoptosis," J Biol Chem (2009) vol. 284, No. 48, pp. 33425-33436.
Noguchi et al., "Ketogenic Essential Amino Acids Modulate Lipid Synthetic Pathways and Prevent Hepatic Steatosis in Mice," PLOS One (2010) vol. 5, Issue 8, Article e12057, 14 pp.
Norton et al., "Leucine content of dietary proteins is a determinant of postprandial skeletal muscle protein synthesis in adult rats," Nutr Metab vol. 9, 67 (2012).
Norton et al., "The leucine content of a complete meal directs peak activation but not duration of skeletal muscle protein synthesis and mammalian target of rapamycin signaling in rats," J Nutr (2009) vol. 139, pp. 1103-1109.
Ohara et al., "L-Carnitine Suppresses Loss of Skeletal Muscle Mass in Patients With Liver Cirrhosis," Hepatology Communications (2018) vol. 2, No. 8, pp. 906-918.
Okita et al., "Nutritional Treatment of Liver Cirrhosis by Branched-Chain Amino Acid-Enriched Nutrient Mixture," J Nutr Sci Vitaminol (1985) vol. 31, No. 3, pp. 291-303.
Pacana, T. et al., "Dysregulated Hepatic Methionine Metabolism Drives Homocysteine Elevation in Diet-Induced Nonalcoholic Fatty Liver Disease," PLoS One, Aug. 31, 2015; 10(8):e0136822. doi: 10.1371/journal.pone.0136822. eCollection 2015.
Paddon-Jones et al., "Essential Amino Acid and Carbohydrate Supplementation Ameliorates Muscle Protein Loss in Humans during 28 Days Bedrest," J Clin Endocrinol Metab (2004) vol. 89, pp. 4351-4358.
Palacio et al., "Anti-inflammatory properties of N-acetylcysteine on lipopolysaccharide-activated macrophages," Inflamm Res (2011) vol. 60, pp. 695-704.
Pennings et al., "Whey protein stimulates postprandial muscle protein accretion more effectively than do casein hydrolysate in older men," Am J Clin Nutr (2011) vol. 93 pp. 997-1005.
Peters et al., "Dose-dependent effects of leucine supplementation on preservation of muscle mass in cancer cachectic mice," Oncol Rep (2011) vol. 26, pp. 247-254.
Petrat et al., "Glycine, a simple physiological compund protecting by yet puzzling mechanism(s) against ischaemia-reperfusion injury: current knowledge," Br J Pharmacol (2011) vol. 165, pp. 2059-2072.
Piatti, P.M. et al., "Long-Term Oral L-Arginine Administration Improves Peripheral and Hepatic Insulin Sensitivity in Type 2 Diabetic Patients," (2001) Diabetes Care, vol. 24, No. 5, May 2001; 24(5):875-80.
Piccolo, B.D. et al., "Plasma Amino Acid and Metabolite Signatures Tracking Diabetes Progression in the UCD-T2DM Rat Model," Am J Physiol Endocrinol Metab, Jun. 1, 2016; 310(11):E958-69. doi: 10.1152/ajpendo.00052.2016. Epub Apr. 19, 2016.
Pilar et al., "L-Ornithine Aspartate Among Cirrhotic Patients with Hepatic Encephalopathy: Does it make a difference?" Phil J of Gastroenterology (2006) vol. 2, pp. 87-94.

(56) References Cited

OTHER PUBLICATIONS

Pinheiro et al., "Metabolic and functional effects of beta-hydroxy-beta-methylbutyrate (HMB) supplementation in skeletal muscle," Eur J Appl Physiol (2012) vol. 112, pp. 2531-2537, first published online Nov. 2011, doi: 10.1007/s00421-011-2224-5.
Pintile, D.G. et al., "Hepatic Stellate Cells' Involvement in Progenitor Mediated Liver Regeneration," Lab Invest, Aug. 2010; 90(8):1199-208. doi: 10.1038/labinvest.2010.88. Epub May 3, 2010.
Poo et al., "Efficacy of oral L-ornithine-L-aspartate in cirrhotic patients with hyperammonemic hepatic encephalopathy. Results of a randomized, lactulose-controlled study," Annals of Hepatology (2006) vol. 5, No. 4, pp. 281-288.
Prod'Homme et al., "Insulin and amino acids both strongly participate to the regulation of protein metabolism," Curr Opin Clin Nutr Metab Care (2004) vol. 7, pp. 71-77.
Qiu et al., "Hyperammonemia-mediated autophagy in skeletal muscle contributes to sarcopenia of cirrhosis," Am J Physiol Endocrinol Metab (2012) vol. 303, pp. E983-E993.
Reccia et al., "Non-alcoholic fatty liver disease: A sign of systemic disease," Metabolism Clinical and Experimental (2017) vol. 72, pp. 94-108.
Rees et al., "Effect of L-ornithine-L-aspartate on patients with and without TIPS undergoing glutamine challenge: a double-blind, placebo controlled trial," Gut (2000) vol. 47, pp. 571-574.
Ren et al., "Serum Amino Acids Profile and the Beneficial Effects of L-Arginine or L-Glutamine Supplementation in Dextran Sulfate Sodium Colitis," PLOS One (2014) vol. 9, Issue 2, Article e88335, 13 pages.
Ritze et al., "Effect of tryptophan supplementation on diet-induced non-alcoholic fatty liver disease in mice," Br J Nutr (2014) vol. 112, pp. 1-7.
Rombouts et al., "Targeting the muscle for the treatment and prevention of hepatic encephalopathy," Journal of Hepatology (2016) vol. 65, pp. 876-878.
Romero-Gómez et al., "Altered resonse to oral glutamine challenge as prognostic factor for overt episodes in patientswith minimal hepatic encephalopathy," Journal of Heaptology (2002) vol. 37, pp. 781-787.
Romero-Gómez et al., "Prognostic Value of Altered Oral Glutamine Challenge in Patients With Minimal Hepatic Encephalopathy," Hepatology (2004) vol. 39, No. 4, pp. 939-943.
Rose et al., "L-Ornithine-L-Aspartate in Experimental Portal-Systemic Encephalopathy: Therapeutic Efficacy and Mechanism of Action," Metab Brain Dis (1998) vol. 13, No. 2, pp. 147-157.
Rose et al., "L-Ornithine-L-Aspartate Lowers Plasma and Cerebrospinal Fluid Ammonia and Prevents Brain Edema in Rats with Acute Liver Failure," Hepatology (1999) vol. 30, No. 3, pp. 636-640.
Roseguini et al., "Effects of N-Acetylcysteine on skeletal muscle structure and function in a mouse model of peripheral arterial insufficiency," J Vasc Surg (2015) vol. 61, pp. 777-786.
Rui, "Energy Metabolism in the Liver," Compr Physiol (2014) vol. 4, No. 1, pp. 177-197.
Saad et al., "Attenuation of carbon tetrachloride induced hepatic fibrosis by glycine, vitamin E, and vitamin C," J Exp Integr Med (2014) vol. 4, Issue 3, pp. 180-186.
Sabater et al., "Altered Nitrogen Balance and Decreased Urea Excretion in Male Rats Fed Cafeteria Diet Are Related to Arginine Availability," BioMed Research International (2014) vol. 2014, Article 959420, 9 pp.
Sakai, H. et al., "Chemoprevention of Obesity-Related Liver Carcinogenesis by Using Pharmaceutical and Nutraceutical Agents," World J Gastroenterol, Jan. 7, 2016; 22(1): 394-406.
Salvatore et al., "Prevention of Ammonia Toxicity by Amino-acids concerned in the Biosynthesis of Urea," Nature (1961) vol. 191, No. 4789, pp. 705-706.
Samuel et el., "Nonalcoholic Fatty Liver Disease as a Nexus of Metabolic and Hepatic Diseases," Cell Metabolism (2017) vol. 27, doi: 10.1016/j.cmet.2017.08.002, 20 pp.
Sansbury, B.E. et al., "Regulation of Obesity and Insulin Resistance by Nitric Oxide," (2014)—Free Radical Biology and Medicine, 73: 383-399.
Schiffrin, "Enteral nutrition in the ICU. The Nestle Modulis innovation. Physiopathology of the traumatized patient in the ICU," Nutrition clinique et metabolisme (2007) vol. 21, p. S6-S10. Abstract Only.
Schmid et al., "A double-blind, randomized, placebo-controlled trial of intravenous L-ornithine-L-aspartate on postural control in patients with cirrhosis," Liver International (2010) doi: 10.1111/j.1478-3231.2010.02213.x, pp. 574-582.
Schuppan et al., "Determinants of Fibrosis Progression and Regression in NASH," Journal of Hepatology (2017), doi: 10.1016/j.jhep.2017.11.012, 39 pp.
Schwarz et al., "Dietary Protein Affects Gene Expression and Prevents Lipid Accumulation in the Liver in Mice," PLOS One (2012) vol. 7, Issue 10, Article e47303, 9 pp.
Schwimmer, J.B. et al., "In Children With Nonalcoholic Fatty Liver Disease, Cysteamine Bitartrate Delayed Release Improves Liver Enzymes but Does Not Reduce Disease Activity Scores," Gastroenterology, 2016; 151:1141-1154.
Sellmann et al., "Oral arginine supplementation protects female mice from the onset of non-alcoholic steatohepatitis," Amino Acids (2016) vol. 49, No. 7, pp. 1215-1225.
Sellmann et al., "Oral Supplementation of Glutamine Attenuates the Progression of Nonalcoholic Steatohepatitis in C57BL/6J Mice," J Nutr (2017) doi: 10.3945/jn.117.253815, 9 pp.
Sellmann, C. et al., "Oral Glutamine Supplementation Protects Female Mice from Nonalcoholic Steatohepatitis," J Nutr, Oct. 2015; 145(10):2280-6. doi: 10.3945/jn.115.215517. Epub Aug. 5, 2015.
Sen et al., "Oxidative stress after human exercise: effect of N-acetylcysteine supplementation," J Appl Physiol (1994) vol. 76, No. 6, pp. 2570-2577.
Sen et al., "Thiol homeostasis and supplements in physical exercise," Am J Clin Nutr (2000) vol. 72, Supp., pp. 653S-659S.
Setshedi et al., "N-Acetylcysteine Improves Hepatic Insulin Resistance Associated with High-Fat Diet and Alcohol-Induced Steatohepatitis," Gastroenterology (2010) vol. 138, No. 5, p. S801, Abstract S1846.
Sharawy et al., "Attentuation of insulin resistance in rats by agmatine: role of SREBP-1c, mTOR and GLUT-2," Naunyn-Schmiedeberg's Arch Pharmacol (2016) vol. 389, pp. 45-56.
Sharawy et al., "The ergogenic suplement ß-hydroxy-ß-methylbutyrate (HMB) attenuates insulin resistance through suppressinf Glut-2 in rat liver," Can J Physiol Pharmacol (2016) vol. 94, pp. 488-497.
Shimizu, M. et al., "Nutraceutical Approach for Preventing Obesity-Related Colorectal and Liver Carcinogenesis," Int. J. Mol. Sci., 2012, 13, 579-595.
Shrestha et al., "Glutamine inhibits CCl4 induced liver fibrosis in mice and TGF-ß1 mediated epithelial-mesenchymal transition in mouse hepatocytes," Food and Chemical Toxicology (2016) vol. 93, pp. 129-137.
Sidransky et al., "Skeletal muscle protein metabolism changes in rats force-fed a diet inducing an experimental Kwashiorkor-like model," Am J Clin Nutr (1970) vol. 23, pp. 1154-1159.
Sim et al., "L-Serine Supplementation Attenuates Alcoholic Fatty Liver by Enhancing Homocysteine Metabolism in Mice and Rats," J Nutr (2014) vol. 145, pp. 260-267.
Simpson et al., "The nutritional geometry of liver disease including non-alcoholic fatty liver disease (NAFLD)," J Hepatol (2017), doi: 10.1016/; j.jhep.2017.10.005, 10 pp.
Smith et al., "Dietary omega-3 fatty acid supplementation increases the rate of muscle protein synthesis in older adults: a randomized controlled trial," American Journal of Clinical Nutrition (2011) vol. 93, pp. 402-412.
Churchward-Venne et al., "Leucine supplementation of a low-protein mixed macronutrient beverage enhances myofibrillar protein synthesis in young men: a double-blind, randomized trial," Am J Clin Nutr (2014) vol. 99, pp. 276-286.

(56) References Cited

OTHER PUBLICATIONS

Churchward-Venne et al., "Supplementation of a suboptimal protein dose with leucine or essential amino acids: effects on myofibrillar protein syntheses at rest and following resistance exercise in men," J Physiol (2012) vol. 590, No. 11, pp. 2751-2765.
Clemmensen et al., "Oral L-Arginine Stimulates GLP-1 Secretion to Improve Glucose Tolerance in Male Mice," Endocrinology (2013) vol. 154, No. 11, pp. 3978-3983.
ClincalTrials.gov Identifier: NCT01434108 "Effects of the Administration of Ornithine Phenylacetate in Patients with Cirrhosis and Upper Gastrointestinal Bleeding," Clinicaltrials.gov, last updated Mar. 24, 2015, 7 pages.
ClincalTrials.gov Identifier: NCT01548690 "Safety Study of Ornithine Phenylacetate to Treat Patients With Acute Liver Failure (STOP-ALF)," Clinicaltrials.gov, last updated Jan. 12, 2018, 13 pages.
ClincalTrials.gov Identifier: NCT01634230 "Emergency Use of OCR-002 in Acute Liver Failure," Clinicaltrials.gov, last updated Jun. 18, 2014, 4 pages.
ClincalTrials.gov Identifier: NCT01966419 "Phase 2B Efficacy/Safety of Ornithine Phenylacetate in Hospitalized Cirrhotic Patients With Hepatc Encephalopathy (STOP-HE) (STOP-HE)," Clinicaltrials. gov, last updated Aug. 21, 2018, 6 pages.
ClincalTrials.gov Identifier: NCT03159390 "Metabolism of Ornithine Phenylacetate (OCERA OP)," Clinicaltrials.gov, last updated May 23, 2017, 6 pages.
Cuthbertson et al., "Anabolic signaling deficits underlie amino acid resistance of wasting, aging muscle," The FASEB Journal (2005) vol. 19, pp. 422-424.
D'Antona et al., "A Peculiar Formula of Essential Amino Acids Prevents Rosuvastatin Myopathy in Mice," Antioxidents & Redox Signaling (2016) vol. 25, No. 11, pp. 595-608.
D'Antona et al., "Branched-Chain Amino Acid Supplementation Promotes Survival and Supports Cardiac and Skeletal Muscle Mitochondrial Biogenesis in Middle-Aged Mice," Cell Metabolism (2010) vol. 12, pp. 362-372.
Dam et al., "Branched-chain amino acids and muscle ammonia detoxification in cirrhosis," Metab Brain Dis (2013) vol. 28, pp. 217-220.
Dam et al., "Branched-chain amino acids increase arterial blood ammonia in spite of enhanced intrinsic muscle ammonia metabolism in patients with cirrhosis and healthy subjects," Am J Physiol Gastrointest Liver Physiol (2011) vol. 301, pp. G269-G277.
Dangin et al., "The digestion rate of protein is an independent regulating factor of postprandial protein retention," Am J Physiol Endocrinol Metab (2001) vol. 280, pp. E340-E348.
Dardevet et al., "Muscle Wasting and Resistance of Muscle Anabolism: The 'Anabolic Threshold Concept' for Adapted Nutritional Strategies during Sarcopenia" The Scientific World Journal (2012) vol. 93, article 269531.
Dashtabi, A. et al., "Oral L-Arginine Administration Improves Anthropometric and Biochemical Indices Associated With Cardiovascular Diseases in Obese Patients: A Randomized, Single Blind Placebo Controlled Clinical Trial," (2016) Res Cardiovasc Med, February; 5(1): e29419.
Davuluri et al., "Metabolic adaptation of skeletal muscle to hyperammonemia drives the beneficial effects of L-leucine in cirrhosis," J Hepatology (2016) vol. 65, pp. 929-937.
De Bandt et al., "A Randomized Controlled Trial of the Influence of the Mode of Enteral Onithine μ-Ketoglutarate Administration in Burn Patients," J Nutr (1998) vol. 128, pp. 563-569.
Deglaire et al., Hydrolyzed dietary casein as compared with the intact protein reduces postprandial peripheral, but not whole-body, uptake of nitrogen in humans, Am J Clin Nutr (2009) vol. 90, pp. 1011-1022.
Deldicque et al., "Antagonistic effects of leucine and glutamine on the mTOR pathway in myogenic C2C12 cells," Amino Acids (2008) vol. 35, No. 1, pp. 147-155, first published online Nov. 2007.
Deminice et al., "Creatine Supplementation Prevents the Accumulation of Fat in the Livers of Rats Fed a High-Fat Diet," J Nutr (2011) vol. 141, pp. 1799-1804.

Diaz-Rua, E. et al., "Long-Term Intake of a High-Protein Diet Increases Liver Triacylglycerol Deposition Pathways and Hepatic Signs of Injury in Rats," Journal of Nutritional Biochemistry, 46 (2017) 39-48.
Diaz-Rua, E. et al., "Sustained Exposure to Diets with an Unbalanced Macronutrient Proportion Alters Key Genes Involved in Energy Homeostasis and Obesity-Related Metabolic Parameters in Rats," 2014 Food & Function, pp. 1-15.
Dickinson et al., "Aging differentially affects human skeletal muscle amino acid transporter expression when essential amino acids are ingested after exercise," Clin Nutr (2013) vol. 32, pp. 273-280.
Dickinson et al., "Mammalian Target of Rapamycin Complex 1 Activation IS Required for the Stimulation of Human Skeletal Muscle Protein Synthesis by Essential Amino Acids," J Nutr (2011) vol. 141, pp. 856-862.
Dilger et al., "Oral N-acetyl-L-cysteine is a safe and effective precursor of cysteine," J Anim Sci (2007) vol. 85, pp. 1712-1718.
Dillon, "Nutritionally essential amino acids and metabolic signaling in aging," Amino Acids (2012). doi:10.1007/s00726-012-1438-0, 11 pp.
Dirks et al., "Skeletal Muscle Disuse Atrophy Is Not Attenuated by Dietary Protein Supplementation in Healthy Older Men," J Nutr (2014) vol. 144, pp. 1196-1203.
Dohil, R., et al., "Enteric-Coated Cysteamine for the Treatment of Paediatric Non-Alcoholic Fatty Liver Disease," Alimentary Pharmacology & Therapeutics, 33.9 (2011): 1036-1044.
Doi et al., "Isoleucine, a Blood Glucose-Lowering Amino Acid, Increases Glucose Uptake in Rat Skeletal Muscle in the Absence of Increases in AMP-Activated Protein Kinase Activity," J Nutr (2005) vol. 135, pp. 2103-2108.
Doi, M. et al., "Hypoglycemic Effect of Isoleucine Involves Increased Muscle Glucose Uptake and Whole Body Glucose Oxidation and Decreased Hepatic Gluconeogenesis," Am. J. Physiol. Endocrinal Metab., 2007, pp. E1683-E1693, vol. 292.
Dou et al., "Ameliorative effects of glycine in an experimental nonalcoholic steatohepatitis and its correlation between TREM-1 and TREM-2," Am J Transl Res (2016) vol. 8, No. 2, pp. 284-297.
Dreyer et al., "Essential amino acid supplementation in patients following total knee arthroplasty," J Clin Invest (2013) vol. 123, No. 11, pp. 4654-4666.
Dreyer et al., "Leucine-enriched essential amino acid and carbohydrate ingestion following resistance exercise enhances mTOR signaling and protein synthesis in human muscle," Am J Physiol Endocrinol Metab (2008) vol. 294, E392-400.
Drummond et al. "Bed rest impairs skeletal muscle amino acid transporter expression, mTORC1 signaling, and protein synthesis in response to essential amino acids in older adults," Am J Physiol Endocrinol Metab (2012) vol. 302, pp. E1113-E1122.
Drummond et al., "Skeletal muscle protein anabolic response to resistance exercise and essential amino acids is delayed with aging," J Appl Physiol (2008) vol. 104, pp. 1452-1461.
Dröge et al., "Role of Cysteine and Glutathione in HIV infection and cancer cachexia: Therapeutic intervention with N-acetylcysteine," Advances in Phamacology (1997) vol. 38, pp. 581-600.
Du et al., "Effects of Histidine Supplementation on Global Serum and Urine 1H NMR-based Metabolomics and Serum Amino Acid Profiles in Obese Women from a Randomized Controlled Study," J Proteome Res (2017) vol. 16, pp. 2221-2230.
Ejima et al., "A novel diet-induced murine model of steatohepatitis with fibrosis for screening and evaluation of drug candidates for nonalcoholic steatohepatitis," Physiol Rep (2016) vol. 4, No. 21, Article e13016, 13 pp.
Eley et al., "Effect of branched-chain amino acids on muscle atrophy in cancer cachexia," Biochem J (2007) vol. 407, pp. 113-120.
English et al., "Leucine partially protects muscle mass and function during bed rest in middle-aged adults," Am J Clin Nutr (2016) vol. 103, pp. 465-473.
Escobar et al., "Regulation of cardiac and skeletal muscle protein synthesis by individual branched-chain amino acids in neonatal pigs," Am J Physiol Endocrinol Metab (2006) vol. 290, pp. E612-E621.

(56) References Cited

OTHER PUBLICATIONS

Estes et al., "Modeling the Epidemic of Nonalcoholic Fatty Liver Disease Demonstrates an Exponential Increase in Burden of Disease," Presented at the American Association for Study of Liver Disease in Boston (2016), doi: 10.1002/hep.29466, 26 pp.

Evans et al., "Efficacy of a novel formulation of L-Carnitine, creatine, and leucine on lean body mass and functional muscle strength in healthy older adults: a randomized, double-blind placebo-controlled study," Nutrition & Metabolism (2017) vol. 14, No. 7, 15 pp.

Falach-Malik et al., "N-Acetyl-L-Cysteine inhibits the development of glucose intolerance and hepatic steatosis in diabetes-prone mice," Am J Transl Res (2016) vol. 8, No. 9, pp. 3744-3756.

Farghaly et al., "L-arginine and aminoguanidine reduce colonic damage of acetic acid-induced colitis in rats: potential modulation of nuclear factor-KB/p65," Clin Exp Pharmacol Physiol (2014) vol. 41, No. 10, pp. 769-779, Abstract Only.

Farid et al., "Effects of dietary curcumin or N-acetylcysteine on NF-KB activity and contractile performance in ambulatory and unloaded murine soleus," Nutrition & Metabolism (2005) vol. 2, No. 20, 8 pages.

Fazelian, S et al., "Effects of L-Arginine Supplementation on Antioxidant Status and Body Composition in Obese Patients with Pre-diabetes: A Randomized Controlled Clinical Trial," (2014) Adv Pharm Bull, 4(Suppl 1), 449-454.

Ferrando et al., "EAA supplementation to increase nitrogen intake improves muscle function during bed rest in the elderly," Clinical Nutrition (2010) vol. 29, pp. 18-23.

Francaux et al., "Aging Reduces the Activation of the mTORC1 Pathway after Resistance Exercise and Protein Intake in Human Skeletal Muscle: Potential Role of REDD1 and Impaired Anabolic Sensitivity," Nutrients (2016) vol. 8, Article 47, 16 pp.

Addison et al., "Intermuscular Fat: A Review of the Consequences and Causes," International Journal of Endrocrinology (2014)vol. 2014, Article 309570, 11 pp.

Holloway et al., "A Novel Amino Acid Composition Ameliorates Short-Term Muscle Disuse Atrophy in Healthy Young Men," Frontiers in Nutrition (2019) vol. 6, Article 105, 10 pages.

International Search Report and Written Opinion issued in PCT/US2019/037932, dated Oct. 7, 2019.

International Search Report and Written Opinion issued in PCT/US2019/037936, dated Oct. 2, 2019.

Lee et al., "AXA1125, a novel defined amino acid composition (DAAC), improves NAFLD activity score (NAS) and reduces fibrosis in two rodent models of nonalcoholic steatohepatitis (NASH)," EASL Abstracts from the First NAFLD Summit (2017) Abstract P02-05, pp. 64-65.

Smith et al., "Treatment of Non-Alcoholic Fatty Liver Disease (NAFLD): Role of AMPK," Am J Physiol Endocrinol Metab (2016) doi:10.1152/ajpendo.00225.2016, 25 pp.

Soomro et al., "Role of Branched Chain Amino Acids in the Management of Hepatic Encephalopathy," World J Med Sci (2008) vol. 3, No. 2, pp. 60-64.

Staedt et al., "Effects of ornithine aspartate on plasma ammonia and plasma amino acids in patients with cirrhosis. A double-blind, randomized study using a four-fold crossover design," Journal of Hepatology (1993) vol. 19, pp. 424-430.

Stauch et al., "Oral L-ornithine-L-aspartate therapy of chronic heaptic encephalopathy: results of a placebo-controlled double-blind study," Journal of Hepatology (1998) vol. 28, pp. 856-864.

Stokes et al., "L-ornithine L-aspartate for people with cirrhosis and hepatic encephalopathy," Cochrane Database of Systematic Reviews (2016) Issue 10, Art No. CD012410, 14 pages.

Sun et al., "Melatonin improves non-alcoholic fatty liver disease via MAPK-JNK/P38 signaling in high-fat-diet-induced obese mice," Lipids in Health and Disease (2016) vol. 15, Article 202, 8 pp.

Sunny et al., "Cross-talk between branched-chain amino acids and hepatic mitochondria is compromised in nonalcoholic fatty liver disease," Am J Physiol Endocrinol Metab (2015) vol. 309, pp. E311-E319.

Suryawan et al., "Leucine stimulates protein synthesis in skeletal muscle of neonatal pigs by enhancing mTORC1 activation," Am J Physiol Endocrinol Metab (2008) vol. 295, pp. E868-E875.

Tachibana et al., "Intake of Mung Bean Protein Isolate Reduces Plasma Triglyceride Level in Rats," Functional Foods in Health and Disease (2013) vol. 3, No. 9, pp. 365-376.

Tajiri et al., "Branched-chain amino acids in liver diseases," World J Gastroenterol (2013) vol. 19, Issue 43, pp. 7620-7629.

Takaguchi et al., "Effects of branched-chain amino acid granules on serum albumin level and prognosis are dependent on treatment adherence in patients with liver cirrhosis," Hepatology Research (2013) vol. 43, pp. 459-466.

Takashi et al., "Branched-chain amino acids alleviate hepatic steatosis and liver injury in choline-deficient high-fat diet induced NASH mice," Metabolism (2017) doi: 10.1016/j.metabol.2016.12.013, 45 pp.

Takegoshi, K. et al., "Branched-Chain Amino Acids Prevent Hepatic Fibrosis and Development of Hepatocellular Carcinoma in a Non-Alcoholic Steatohepatitis Mouse Model," Oncotarget, Mar. 14, 2017; 8(11):18191-18205. doi:10.18632/oncotarget.15304.

Talvas et al., "Regulation of protein synthesis by leucine starvation involves distinct mechanisms in mouse C2C12 myoblasts and myotubes," J Nutr (2006) vol. 136, pp. 1466-1471.

Tan, B et al., "Regulatory Roles for L-Arginine in Reducing White Adipose Tissue," (2012) Frontiers in Bioscience, 17, 2237-2246, Jun. 1.

Tanaka et al., "Branched-chain Amino Acid-Rich Supplements Containing Microelements Have Antioxidant Effects on Nonalcoholic Steatohepatitis in Mice," J Parenteral and Enteral Nutrition (2016) vol. 40, No. 4, pp. 519-528.

Theytaz et al., "Effects of supplementation with essential amino acids on intrahepatic lipid concentrations during frutose overfeeding in mice," Am J Clin Nutr (2012) vol. 96, pp. 1008-1016.

Thomsen et al., "Experimental nonalcoholic steatohepatitis compromises ureagenesis, an essential hepatic metabolic function," Am J Physiol Gastrointest Liver Physiol (2014) vol. 307, pp. G295-G301.

Thong-Ngam et al., "N-acetylcysteine attenuates oxidative stress and liver pathoogy in rats with non-alcoholic steatohepatitis," World J Gastroenterol (2007) vol. 13, No. 38, pp. 5127-5132.

Tsien et al., "Metabolic and Molecular Responses to Leucine-Enriched Branched Chain Amino Acid Supplementation in the Skeletal Muscle of Alcoholic Cirrhosis," Hepatology (2015) vol. 61, No. 6, pp. 2018-2029.

Ullrich et al., "Intragastric administration of leucine or isoleucine lowers the blood glucose response to a mixed-nutrient drink by different mechanisms in healthy, lean volunteers," Am J Clin Nutr (2016) vol. 104, pp. 1274-1284.

Van De Poll et al., "Intestinal and hepatic metabolism of glutamine and citrulline in humans," J Physiol (2007) vol. 581, No. 2, pp. 819-827.

Van Vliet et al., "The Skeletal Muscle Anabolic Response to Plant-versus Animal-Based Protein Consumption," J Nutr (2015) vol. 14, No. 5, pp. 1981-1991.

Varakanahalli et al., "Secondary prophylaxis of hepatic encephalopathy in cirrhosis of liver: a double-blind randomized controlled trial of L-ornithine L-aspartate versus placebo," Eur J Gastroenterol Hepatol (2018) vol. 30, pp. 951-958.

Vela et al., "Efficacy of oral L-orinthine L-aspartate in cirrhotic patients with hyperammonemic hepatic encephalopathy," Annals of Hepatology (2011) vol. 10, Supp. 2, pp. S55-S59.

Ventura et al., "Evidence for a role of the ileum in the control of nitrogen homeostasis via the regulation of arginine metabolism," Br J Nutr (2011) vol. 106, pp. 227-236.

Ventura-Cots et al., "Impact of ornithine phenylacetate (OCR-002) in lowering plasma ammonia after upper gastrointestinal bleeding in cirrhotic patients," Ther Adv Gastroenterol (2016) vol. 9, No. 6, pp. 823-836.

Wahren, J. et al., "Is Intravenous Administration of Branched Chain Amino Acids Effective in the Treatment of Hepatic Encephalopathy? A Multicenter Study. (abstract only)," Hepatology, Jul.-Aug. 1983; 3(4):475-80.

(56) References Cited

OTHER PUBLICATIONS

Watanabe et al., Beneficial Effect of Food Substitute Containing L-Arginine, w-3 Poly Unsaturated Fatty Acid, and Ribonucleic Acid in Preventing or Improving Metabolic Syndrome: A Study in 15 Overweight Patients and a Study of Fatty Acid Metabolism in Animals, J Clin Biochem Nutr (2009) vol. 44, pp. 266-274.
Wilkinson et al., "Effects of leucine and its metabolite b-hydroxy-b-methylbutyrate on human skeletal muscle protein metabolism," J Physiol (2013) vol. 591, No. 11, pp. 2911-2923.
Wilson et al., "Differential effects of long-term leucine infusion on tissue protein synthesis in neonatal pigs," Amino Acids (2011) vol. 40, pp. 157-165.
Xu et al., "Ketogenic essential amino acids replacement diet ameliorated hepatosteatosis with altering autophagy-associated molecules," Biochimica et Biophysica Acta (2013) vol. 1832, pp. 1605-1612.
Yamada et al., Association between insulin resistance and plasma amino acid profile in non-diabetic Japanese subjects, J Diabetes Invest (2015) vol. 6, pp. 408-415.
Yamamoto et al., "Branched-chain amino acids protect against dexamethasone-induced soleus muscle atrophy in rats," Muscle Nerve (2010) vol. 41, pp. 819-827.
Yang et al., "Resistance exercise enhances myofibrillar protein synthesis with graded intakes of whey protein in older men," Br J Nutr (2012) vol. 108, pp. 1780-1788.
Yao et al., "Dietary Arginine Supplementation Increases mTOR Signaling Activity in Skeletal Muscle of Neonatal Pigs," J Nutr (2008) vol. 138, pp. 867-872.
Yi et al., N-Acetylcysteine improves intestinal function in lipopolysaccharides challenged piglets through multiple signaling pathways, Amino Acids (2017) doi: 10.1007/s00726-017-2389-2, 15 pp.
Yin et al., "Supplementing L-leucine to a low-protein diet increases tissue protein synthesis in weanling pigs," Amino Acids (2010) vol. 39, pp. 1477-1486.
Yokota et al., "Leucine restores murine hepatic triglyceride accumulation induced by a low-protein diet by suppressing autophagy and excessive endoplasmic reticulum stress," Amino Acids (2016) vol. 48, pp. 1013-1021.
Yoshiji et al., "Branched-chain amino acids suppress the cumulative recurrence of hepatocellular carcinoma under condititions of insulin-resistance," Oncology Reports (2013) vol. 30, pp. 545-552.
Younossi et al., "Global burden of NAFLD and NASH: trends, predictions, risk factors and prevention," Nat Rev (2017) doi:10.1038/nrgastro.2017.109, 10 pp.
Yuan et al., "Leucine supplementation improves leptin sensitivity in high-fat diet fed rats," Food & Nutrition Research (2015) vol. 59, Article 27373, 6 pp.
Zarfeshani et al., "Leucine alters hepatic glucose/lipid homeostasis via the myostatin-AMP-activated protein kinase pathway—potential implications for nonalcoholic fatty liver disease," Clinical Epigenetics (2014) vol. 6, Article 27, 12 pages.
Zeanandin et al., "Differential effect of long-term leucine supplementation on skeletal muscle and adipose tissue in old rats: an insulin signaling pathway approach," Age (2012) vol. 34, pp. 371-387.
Zhang et al., "Branched Chain Amino Acids Cause Liver Injury in Obese/Diabetic Mice by Promoting Adipocyte Lipolysis and Inhibiting Hepatic Autophagy," EBioMedicine (2016) vol. 13, pp. 157-167.
Zhang et al., Supporting Materials for "Branched Chain Amino Acids Cause Liver Injury in Diabetic Mice by Promoting Adipocyte Lipolysis and Inhibiting Hepatic Autophagy," EBioMedicine (2016) doi.org/10.1016/j.ebiom.2016.10.013, 15 pp.
Zhang, Y. et al., "Increasing Dietary Leucine Intake Reduces Diet-Induced Obesity and Improves Glucose and Cholesterol Metabolism in Mice via Multimechanisms," Diabetes. Jun. 2007; 56(6):1647-54. Epub Mar. 14, 2007.
Zhou et al., "Glycine protects against high sucrose and high fat-induced non-alcoholic steatohepatitis in rats," Oncotarget (2016) vol. 7, No. 49, pp. 80223-8237.

[No Author Listed] MediKAL Nutrience Hepatosol-LOLA product information, retrieved from www.medikalnutrience.com/EN/Product/By-Brand/Hepatosol-LOLA, last accessed Sep. 13, 2018, 9 pages.
[No Author Listed] New Drug Application 18-676 and Approval Letter for HepatAmine (1982), 73 pages.
[No Author Listed] NUTRIHEP product information, retrieved from www.nestlehealthscience-me.com/en/brands/nutrihep/nutrihep, last accessed Sep. 12, 2013.
Abid et al., "Efficacy of L-ornithine-L-aspartate as an Adjuvant Therapy in Cirrhotic Patients with Hepatic Encephalopathy," Journal of the College of Physicians and Surgeons Pakistan (2011) vol. 21, No. 11, pp. 666-671.
Abu-Serie, M.M. et al., "Investigation into the Antioxidant Role of Arginine in the Treatment and the Protection for Intralipid-Induced NASH," (2015), Lipids in Health and Disease, 14:128.
Achamrah et al., "Glutamine and the regulation of intestinal permeability: from bench to bedside," Curr Opin Clin Nutr Metab Care (2017) vol. 20, pp. 86-91.
Acharya et al., "Efficacy of L-Ornithine L-Aspartate in Acute Liver Failure: A Double-Blind, Randomized, Placebo-Controlled Study," Gastroenterology (2009) vol. 136, pp. 2159-2168.
Adeva et al., "Insulin resistance and the metabolism of branched-chain amino acids in humans," Amino Acids (2012) vol. 43, pp. 171-181.
Adibi et al., "Metabolism of branched-chain amino acids in altered nutrition," Metab Clin Exp (1976) vol. 25, pp. 1287-1302.
Agarwal et al., "Supplemental Citrulline Is More Efficient than Arginine in Increasing Systemic Arginine Availability in Mice," J Nutr (2017) doi: 10.3945/jn.116.240382, 7 pp.
Agli et al., "Erythrocytes participate significantly in blood transport of amino acids during the post absorptive state in normal humans," Eur J Appl Physiol (1998) vol. 78, pp. 502-508.
Agten et al., "N-Acetylcysteine protects the rat diaphragm from the decreased contractility associated with controlled mechanical ventilation," Crit Care Med (2011) vol. 39, No. 4, pp. 777-782.
Ahmad et al., "L-Ornithine-L-Aspartate Infusion Efficacy in Hepatic Encephalopathy," Journal of the College of Physicians and Surgeons Pakistan (2008) vol. 18, No. 11, pp. 684-687.
Amodio et al., "Nutritional Management of Hepatic Encephalopathy in Patients With Cirrhosis: International Society for Hepatic Encephalopathy and Nitrogen Metabolism Consensus," Hepatology (2013) vol. 58, pp. 325-336.
Anthony et al., "Leucine stimulates translation initiation in skeletal muscle of postabsorptive rats via a rapamycin-sensitive pathway," J Nutr (2000) vol. 130, pp. 2413-2419.
Apostol et al., "A Decrease in Glucose Production Is Associated With an Increase in Plasma Citrulline Response to Oral Arginine in Normal Volunteers," Metabolism (2003) vol. 52, No. 11, pp. 1512-1516.
Araujo et al., "Benefits of L-alanine or L-arginine supplementation against adiposity and glucose intolerance in monosodium glutamate-induced obesity," Eur J Nutr (2016) doi: 10.1007/s00394-016-1245-6, 12 pp.
Aversa et al., "ß-hydroxy-ß-methylbutyrate (HMB) attenuates muscle and body weight loss in experimental cancer cachexia," International J of Oncology (2011) vol. 38, pp. 713-720.
B. Braun Medical Inc., Package Insert for HepatAmine, NDA 18-6761S-022 pp. 5-15, Revised May 2003.
B. Braun Medical Inc., Product Catalog for HepatAmine (8% Amino Acid Injection), 2012, retrieved from www.obraunusa.com/content/dam/catalog/bbraun/bbraunProductCatalog/CW_US/en-us/b0/hepatamine-8-aminoacidinjectionbrochure.pdf.bb-.38324315/hepatamine-8-aminoacidinjectionbrochure.pdf.
B. Braun Medical Inc., Product Catalog, retrieved from www.bbraunusa.com/en/products-and-therapies/product-catalog.html, last accessed Sep. 13, 2018.
Backx et al., "Leucine Supplementation Does Not Attenuate Skeletal Muscle Loss during Leg Immobilization in Healthy, Young Men," Nutrients (2018) vol. 10, Article 635, 12 pages.
Bahadoran et al., "Dietary L-arginine intake and the incidence of coronary heart disease: Tehran lipid and glucose study," Nutrition & Metabolism (2016) vol. 13, No. 23, 9 pp.

(56) References Cited

OTHER PUBLICATIONS

Balage et al., "Leucine supplementation in rats induced a delay in muscle IR/PI3K signaling pathway associated with overall impaired glucose tolerance," The Journal of Nutritional Biochemistry (2011) vol. 22, pp. 219-226 (Abstract Only).
Balage et al., "Long-term effects of leucine supplementation on body composition," Curr Opin Clin Nutr Metab Care (2010) vol. 13, pp. 265-270.
Baptista et al., "Leucine attenuates skeletal muscle wasting via inhibition of ubiquitin ligases," Muscle Nerve (2010) vol. 41, pp. 800-808.
Bauchart-Thevret et al., "Arginine-induced stimulation of protein synthesis and survival in IPEC-J2 cells is mediated by mTOR but not nitric oxide," Am J Physiol Endocrinol Metab (2010) vol. 299, pp. E899-E909.
Baum et al., "Docosahexaenoic Acid (DHA), not Leucine, May Protect HepG2 Cells from Palmitate-Induced Non-Alcoholic Fatty Liver Disease," FASEB J (2017) Abstract No. 1036.7.
Baum et al. "Leucine reduces the duration of insulin-induced PI 3-kinase activity in rat skeletal muscle," Am J Physiol Endocrinol Metab (2005) vol. 288, pp. E86-E91.
Baumgardner, J.N. et al., "N-Acetylcysteine Attenuates Progression of Liver Pathology in a Rat Model of Nonalcoholic Steatohepatitis," J Nutr, Oct. 2008; 138(10):1872-9.
Bernard et al., "An amino acid mixture is essential to optimize insulin-stimulated glucose uptake and GLUT4 translocation in perfused rodent hindlimb muscle," J Appl Physiol (2012) vol. 113, pp. 97-104.
Binder et al., "Leucine Supplementation Protects from Insulin Resistance by Regulating Adiposity Levels," PLOS One (2013) vol. 8, No. 9, Article e74705, 12 pp.
Bos et al., "Postprandial Kinetics of Dietary Amino Acids Are the Main Determinant of Their Metabolism after Soy or Milk Protein Ingestion in Humans," J Nutr (2003) vol. 133, pp. 1308-1315.
Bostock et al., "Effects of Essential Amino Acid Supplementation on Muscular Adaptations to 3 Weeks of Combined Unilateral Glenohumeral & Radiohumeral Joints Immobilisation," J Athl Enhancemnet (2013) vol. 2, No. 3, Article 1000116, 9 pp.
Breen et al., "Skeletal muscle protein metabolism in the elderly: Interventions to counteract the 'anabolic resistance' of ageing," Nutr Metab (2011) vol. 8: 68, 11 pp.
Breuillard et al., "Citrulline and nitrogen homeostasis: an overview," Amino Acids (2015) vol. 47, pp. 685-691.
Breuille et al., "Beneficial effect of amino acid supplementation especially cysteine, on body nitrogen economy in septic rats," Clinical Nutrition (2006) vol. 25, pp. 634-642.
Butterworth et al., "Hepatoprotection by L-Ornithine L-Aspartate in Non-Alcoholic Fatty Liver Disease," Dig Dis (2018) DOI: 10.1159/000491429, 6 pages.
Bémeur et al., "Nutrition in the Management of Cirrhosis and its Neurological Complications," J Clin Exp Hepatol (2014) vol. 4, No. 2, pp. 141-150.
Børsheim et al., "Amino acid supplementation decreases plasma and liver triglycerides in elderly," Nutrition (2009) vol. 25, No. 3, pp. 281-288.
Børsheim et al., "Effect of amino acid supplementation on muscle mass, strength and physical function in elderly," Clin Nutr (2008) vol. 27, pp. 189-195.
Campollo et al., "Protein tolerance to standard and high protein meals in patients with liver cirrhosis," World J Hepatol (2017) vol. 9, Issue 14, pp. 667-676.
Campos-Ferraz et al., "Distinct effects of leucine or a mixture of the branched-chain amino acids (leucine, isoleucine, and valine) supplementation on resistance to fatigue, and muscle and liver-glycogen degradation, in trained rats," Nutrition (2013) vol. 29, pp. 1388-1394.
Capel et al., "Combining citrulline with atorvastatin preserves glucose homeostasis in a murine model of diet-induced obesity," Br J Pharmacol (2015) vol. 172, pp. 4996-5008.

Capel et al., "Lysosomal and proteasome-dependent proteolysis are differentially regulated by insulin and/or amino acids following feeding in young, mature and old rats," J Nutr Biochem (2009) vol. 20, pp. 570-576.
Carraro et al., "Whole body and plasma protein synthesis in exercise and recovery in human subjects," Am J Physiol Endocinol Metab (1990) vol. 258, pp. E821-E831.
Chang et al., "Leucine inhibits oxidation of glucose and pyruvate in skeletal muscles during fasting," J Biol Chem (1978) vol. 253, pp. 3696-3701.
Charlton, M., "Branched-Chain Amino Acid Enriched Supplements as Therapy for Liver Disease," 2006 J. Nutrition, 136: 295S-298S.
Chartrand et al., "Influence of Amino Acids in Dairy Products on Glucose Homeostasis: The Clinical Evidence," Can J Diabetes (2017), 9 pp.
Cheng et al., "Adipose Tissue Dysfunction and Altered Systemic Amino Acid Metabolism Are Associated with Non-Alcoholic Fatty Liver Disease," PLOS One (2015) doi:10.1371/journal.pone.0138889, 17 pp.
[No Author Listed] Twinlab "Anti-catabolic HMB Fuel Plus: HMB, NAC, Glutamine & Creatine," Product Label, 1996.
Alvares-da-Silva et al., "Oral l-ornithine-l-aspartate in minimal hepatic encephalopathy: A randomized, double-blind, placebo-controlled trial," Hepatology Research (2014) vol. 44, pp. 956-963.
Argilés et al., "Branched-chain amino acid catabolism and cancer cachexia (Review)," Oncol Rep (1996) vol. 3, No. 4, pp. 687-690.
Bai et al., "Randomised clinical trial: L-ornithine-L-aspartate reduces significantly the increase of venous ammonia concentration after TIPSS," Ailment Pharmacol Ther (2014) vol. 40, pp. 63-71.
Brioche et al., "Muscle wasting and aging: Experimental models, fatty infiltrations, and prevention," Molecular Aspects of Medicine (2016) VI. 50, pp. 56-87.
Calvey et al., "Controlled Trial of Nutritional Supplementation With and Without Branched Chain Amino Acid Enrichment, in Treatment of Acute Alcoholic Heptatitis," Journal of Hepatology (1985) vol. 1, pp. 141-151.
Campos-Ferraz et al., "An overview of amine as nutritional supplements to counteract cancer cachexia," J Cachexia Sarcopenia Muscle (2014) vol. 5, No. 2, pp. 105-110.
Chen et al., "Therapeutic effect of L-ornithine-L-aspartate on liver cirrhosis complicated by hepatic encephalopathy," J First Mil Med Univ (2005) vol. 25, No. 6, pp. 718-722. Abstract Only.
Cholewa et al., "Dietary proeteins and amino acids in the control of the muscle mass during immobilization and aging: role of the MPS response," Amino Acids (2017) vol. 49, No. 5, pp. 811-820.
Deutz et al., "Protein intake and exercise for optimal muscle function with again: Recoomndations from the ESPEN Expert Group," Clinical Nutrition (2014) vol. 33, pp. 929-936.
Egberts et al., "Branched Chain Amino Acids in the Treatment of Latent Portosystemic Encephalopathy," Gastroenterology (1985) vol. 88, pp. 887-895.
Feher et al., "Effect of ornithine-aspartate infusion on elevated serum ammonia concentration in cirrhotic patients—results of a randomized, placebo-controlled double-blind multicentre trial," Med Sci Monit (1997) vol. 3, No. 5, pp. 669-673.
Gluud et al., "Branched-chain amino acids for people with hepatic encephalopathy," The Cochrane Review (2015) Issue 9, 89 pages.
Gomes et al., "Hepatic injury and disturbed amino acid metabolism in mice following prolonged exposure to organophosphorus pesticides," Human and Experimental Toxicology (1999) vol. 18, No. 1, pp. 33-37.
Gumucio et al., "Aging-associated exacerbation in fatty degeneration and infiltration after rotator cuff tear," J Shoulder Elbow Surg (2014) vol. 23, pp. 99-108.
Hayashi et al., "A Randomized Controlled Trial of Branched-Chain Amino Acid (BCAA)-Enriched Elemental Diet (ED-H) for Hepatic Encephalopathy," J Gastroenterol Hepatol (1991) vol. 6, p. 191, Abstract Only.
Higuera-de-la-Tijera et al., Primary Prophylaxis to Preventthe Development of Hepatic Enchephalopathy in Cirrhotic Patients with Acute Variceal Bleeding, Candian Journal of Gastroenterology and Hepatology (2018) Article 3015891, 10 pages.

(56) References Cited

OTHER PUBLICATIONS

Horst et al., "Comparison of Dietary Protein with an Oral, Branched Chain-Enriched Amino Acid Supplement in Chronic Portal-Systemic Encephalopathy: A Randomized Controlled Trial," Hepatology (1984) vol. 4, No. 2, pp. 279-287.
International Search Report and Written Opinion issued in PCT/US2018/046705, dated Nov. 23, 2018, 13 pages.
Kircheis et al., "Assessment of low-grade hepatic encephalopathy: a critical analysis," Journal of Hepatology (2007) vol. 47, pp. 642-650.
Les et al., "Effects of Branched-Chain Amino Acids Supplementation in Patients with Cirrhosis and a Previous Episode of Hepatic Encephalopathy: A Randomized Study," Am J Gastroenterol (2011) vol. 106, pp. 1081-1088.
Marchesini et al., "Long-term oral branched-chain amino acid treatment in chronic hepatic encephalopathy," Journal of Hepatology (1990) vol. 11, pp. 92-101.
Ortiz de Montellano et al., "A New Step in the Treatment of Sickle Cell Disease," Biochemistry (2018) vol. 57, No. 5, pp. 470-471, Abstract.
Pace et al., "Effect of N-acetylcysteine on Dense Cell Formation in Sickle Cell Disease," American Journal of Hematology (2003) vol. 73, No. 1, pp. 26-32.
Plauth et al., "Long-term treatment of latent portosystemic encephalopathy with branched-chain amino acids," Journal of Heaptology (1993) vol. 73, pp. 308-314.
Rathmacher et al., "Supplementation with a combination of beta-hydroxy-beta-methylbutyrate (HMB), arginine, and glutamine is safe and could improve hematological parameters," J Parenter Enteral Nutr (2004) vol. 28, No. 2, pp. 65-75.
Roederer et al., "N-Acetylcysteine: A New Approach to Anti-HIV Therapy," AIDS Research and Human Retroviruses (1992) vol. 8, No. 2, pp. 209-217.
Sharma et al., "Effect of Rifazimin, Probiotics, and l-Ornithine l-Aspartate on Minimal Hepatic Encephalopathy: A Randomized Controlled Trial," Saudi J Gastroenterol (2014) vol. 20, pp. 225-232.
Sidhu et al., "L-Ornithine L-Aspartate in Bouts of Overt Hepatic Encephalopathy," Hepatology (2018) vol. 67, No. 2, pp. 700-710.
Waugh et al., "Evidence that L-Arginine is a Key Amino Acid in Sickle Cell Anemia—A Preliminary Report," Nutrition Research (1999) vol. 19, No. 4, pp. 501-518.
Frank et al., "Dietary protein and lactose increase translation initiation factor activation and tissue protein synthesis in neonatal pigs," Am J Physiol Endocrinol Metab (2006) vol. 290, pp. E225-E233.
Fresenius Kabi, Kabiven® Product Information revised 2016, 24 pages.
Fresenius Kabi, Perikabiven® Product Information revised 2016, 24 pages.
Freudenberg, A. et al., "Comparison of High-Protein Diets and Leucine Supplementation in the Prevention of Metabolic Syndrome and Related Disorders in Mice," J Nutr Biochem, Nov. 2012; 23(11):1524-30.
Freudenberg, A. et al., "Dietary L-Leucine and L-Alanine Supplementation Have Similar Acute Effects in the Prevention of High-Fat Diet Induced Obesity," (2012) Amino Acids, 44:519-528.
Frontiers in Hepatology: NASH and Nutritional Therapy pp. 92-114 (Kiwamu Okita, Ed., 2005) Springer-Verlag, Toyko, Japan.
Fu et al., "Leucine amplifies the effets of metformin on insulin sensitivity and glycemic control in diet-induced obese mice," Metabolism Clinical and Experimental (2015), dx.doi.org/10.1016/j.metabol.2015.03.007, 12 pp.
Fujita et al., "Essential amino acid and carbohydrate ingestion before resistance exercise does not enhance postexercise muscle protein synthesis," J Appl Physiol (2009) vol. 106, pp. 1730-1739.
Fujita et al., "Nutrient signalling in the regulation of human muscle protein synthesis," The Journal of Physiology (2007) vol. 582, pp. 813-823.
Fujita, S. et al., "Amino Acids and Muscle Loss with Aging," J Nutr, Jan. 2006; 136(1 Suppl): 277S-280S.
Fukuda et al., "L-Ornithine affects peripheral clock gene expression in mice," Sci Rep (2016) vol. 6, Article 34665, 11 pp.
Gaggini et al., "Altered amino acid concentrations in NAFLD: impact of obesity and insulin resistance," Hepatology, doi: 10.1002/hep.29465, published online Nov. 2017.
Garcia Caraballo et al., "A high-protein diet is anti-steatotic and has no pro-inflammatory side effects in dyslipidaemic APOE2 knock-in mice," Br J Nutr (2014) vol. 112, pp. 1251-1265.
Garcia-Caraballo, S. et al., "Prevention and Reversal of Hepatic Steatosis with a High-Protein Diet in Mice," Biochim Biophys Acta, May 2013; 1832(5):685-95. doi: 10.1016/j.bbadis.2013.02.003. Epub Feb. 11, 2013.
Garg et al., "Therapeutic strategies for preventing skeletal muscle fibrosis after injury," Frontiers in Pharmacology (2015) vol. 6, Article 87, 9 pages.
Gebhardt et al., "Treatment of Cirrhotic Rats with L-Ornithine-L-Aspartate Enhances Urea Synthesis and Lowers Serum Ammonia Levels," J Pharmacol Exp Therapeutics (1997) vol. 283, No. 1, pp. 1-6.
Giam et al., "Effects of Dietary L-Arginine on Nitric Oxide Bioavailability in Obese Normotensive and Obese Hypertensive Subjects," Nutrients (2016) vol. 8, Article 364, 3 pp.
Glover et al., "Immobilization induces anabolic resistance in human myofibrillar protein synthesis with low and high dose amino acid infusion," J Physiol (2008) vol. 586, No. 24, pp. 6049-6061.
Gluchowski et al., "Lipid droplets and liver disease: from basic biology to clinical implications," Nat Rev Gastroenterol Hepatol (2017) doi:10.1038/nrgastro.2017.32, 13 pp.
Gluud et al., "Oral Branched-chain Amino Acids Have a Beneficial Effect on Manifestations of Hepatic Encephaolpathy in a Systematic Review with Meta-Analyses of Randomized Controlled Trials," J Nutr (2013) doi: 10.3945/jn.113.174375, 6 pages.
Goh et al., "L-ornithine L-aspartate for prevention and treatment of hepatic encephalopathy in people with cirrhosis," Cochrane Database of Systematic Reviews (2018) Issue 5, Art No. CD012410, 4 pages.
Goldberg et al., "Oxidation of amino acids by diaphragms from fed and fasted rats," Am J Physiol (1972) vol. 223, pp. 1384-1391.
Goldberg, "Protein synthesis during work-induced growth of skeletal muscle," J Cell Biol (1968) vol. 36, pp. 653-658.
Goldberg, "Protein turnover in skeletal muscle. I. Protein catabolism during work-induced hypertrophy and growth induced with growth hormone," J Biol Chem (1969) vol. 244, No. 12, pp. 3217-3222.
Gomes-Marcondes et al., "A leucine-supplemented diet improved protein content of skeletal muscle in young tumor-bearing rats," Braz J Med Biol Res (2003) vol. 36, pp. 1589-1594.
Gornik et al., "Arginine and Endothelial and Vascular Health," J Nutr (2004) vol. 134, pp. 2880S-2887S.
Graf et al., "Effects of whey protein supplements on metabolism: evidence from human intervention studies," Curr Opin Clin Nutr Metab Care (2011) vol. 14, pp. 569-580.
Guillet et al., "Mitochondrial and sarcoplasmic proteins, but not myosin heavy chain, are sensitive to leucine supplementation in old rat skeletal muscle," Exp Gerontol (2004) vol. 39, pp. 745-751.
Guo et al., "Chronic leucine supplementation improves glycemic control in etiologically distinct mouse models of obesity and diabetes mellitus," Nutrition & Metabolism (2010) vol. 7, Article 57, 10 pp.
Habu et al., "Effect of oral supplementation with branched-chain amino acid granules on serum albumin level in the early stage of cirrhosis: a randomized pilot trial," Hepatology Research (2003) vol. 25, Issue 3, pp. 312-318, Abstract Only.
Haegens et al., "Leucine induces myofibrillar protein accretion in cultured skeletal muscle through mTOR dependent and -independent control of myosin heavy chain mRNA levels," Mol Nutr Food Res (2012) vol. 56, pp. 741-752.
Hagström et al., "Fibrosis stage but not NASH predicts mortality and time to development of severe liver disease in biopsy-proven NAFLD," Journal of Hepatology (2017), doi: 10.1016/j.jhep.2017.07.027, 37 pp.

(56) References Cited

OTHER PUBLICATIONS

Ham et al., "Arginine protects muscle cells from wasting in vitro in a an mTORC1-dependent and NO-independent manner," Amino Acids (2014) vol. 46, Issue 12, pp. 2643-2652.
Harris, L.-A. et al., "Alterations in 3-Hydroxyisobutyrate and FGF21 Metabolism are Associated with Protein Ingestion-Induced Insulin Resistance," Diabetes (Publish Ahead of Print), published online May 4, 2017, 34 pages.
Harrison et al., "Vitamin E and Vitamin C Treatment Improves Fibrosis in Patients With Nonalcoholic Steatohepatitis," Am J Gastroenterol (2003) vol. 98, pp. 2485-2490.
Hassan, A. et al., "Effects of Oral L-Carnitine on Liver Functions after Transarterial Chemoembolization in Intermediate-Stage HCC Patients," Mediators Inflamm, 2015; 2015:608216. doi: 10.1155/2015/608216. Epub Nov. 19, 2015.
Herlong et al., "The Use of Ornithine Salts of Branched-Chain Ketoacids in Portal-Systemic Encephalopathy," Annals of Internal Medicine (1980) vol. 93, pp. 545-550.
Hermier et al., "NO synthesis from arginine is favored by a-linolenic acid in mice fed a high-fat diet," Amino Acids (2016) vol. 48, pp. 2157-2168.
Holdsworth et al., "Body protein metabolism and plasma amino acits in cirrhosis of the liver. The effect of varying the branched chain amino acid content of intravenous amino acid solutions," Clinical Nutrition (1984) vol. 3, pp. 153-162.
Holecek, "Branched-chain amino acid supplementation in treatment of liver cirrhosis: Updated views on how to attenuate their harmful effects on cataplerosis and ammonia formation," Nutrition (2017) vol. 41, pp. 80-85.
Holecek, "Branched-chain amino acids and ammonia metabolism in liver disease," Nutrition (2013) vol. 29, pp. 1186-1191.
Holecek, "Evidence of a vicious cycle in glutamine synthesis and breakdown in pathogenesis of hepatic encephalopathy-therapeutic perspectives," Metab Brain Dis (2014) vol. 29, pp. 9-17.
Holecek, "Three targets of branched-chain amino acid supplementation in the treatment of liver disease," Nutrition (2010) vol. 26, pp. 482-490.
International Search Report and Written Opinion issued in PCT/US2017/067345, dated Mar. 9, 2018, 13 pages.
International Search Report and Written Opinion issued in PCT/US2017/067368, dated Apr. 18, 2018, 12 pages.
Ishikawa, "Early administration of branched-chain amino acid granules," World J Gastroenterol (2012) vol. 18, Issue 33, pp. 4486-4490.
Iwakiri et al., "Nitric oxide in liver diseases," Trends in Pharmacological Sciences (2015) vol. 36, No. 8, pp. 524-536.
Iwasa et al., "Branched-Chain Amino Acid Supplementation Reduces Oxidative Stress and Prolongs Survival in Rats with Advanced Liver Cirrhosis," PLOS One (2013) vol. 8, Issue 7, Article e70309, 11 pages.
Jackman et al., "Branched-Chain Amino Acid Ingestion Stimulates Muscle Myofibrillar Protein Synthesis following Resistance Exercise in Humans," Frontiers in Physiology (2017) vol. 8, Article 390, 12 pages.
Jalan et al., "L-Ornithine phenylacetate (OP): A novel treatment for hyperammonemia and hepatic encephalopathy," Medical Hypotheses (2007) vol. 69, pp. 1064-1069.
[No Author Listed] National Guideline Centre, Royal College of Physicians, "Cirrhosis in over 16s, Assessment and Management," NICE guideline NG50, Appendices A-H, Jul. 2016, 351 pages.
[No Author Listed] PubChem entry for L-Orinthine-L-aspartate, PubChem CID 10220941 (2019), 17 pages.
Hurt et al., "L-Arginine for the Treatment of Centrally Obese Subjects: A Pilot Study," Journal of Dietary Supplements (2014) vol. 11, No. 1, pp. 40-52.
Martina et al., "Long-Term N-Acetylcysteine and L-Arginine Administration Reduces Endothelial Activation and Systolic Blood Pressure in Hyptertensive Patients With Type 2 Diabetes," Diabetes Care (2008) vol. 31, No. 5, pp. 940-944.
Miyake et al., "Long-term Branched-chain Amino Acid Supplementation Improves Glucose Tolerance in Patients with Nonalcoholic Steatohepatitis-related Cirrhosis," Intern Med (2012) vol. 51, pp. 2151-2155.
Squires et al., "A Prospective Clinical Trial Shows That Intravenous N-Aceyticysteine (NAC) Does Not Improve Survival in Pediatric Patients With Non-Acetaminophen Acute Liver Failure," Gastroenterology (2011) vol. 140, Issue 5, Supplement 1, p. S-897.
U.S. Appl. No. 16/674,317, filed Nov. 5, 2019.
Van Loon et al., "Amino Acid Ingestion Strongly Enhances Insulin Secretion in Patients With Long-Term Type 2 Diabetes," Diabetes Care (2003) vol. 26, No. 3, pp. 625-630.

* cited by examiner

COMPOSITIONS AND METHODS FOR THE TREATMENT OF LIVER DISEASES AND DISORDERS ASSOCIATED WITH ONE OR BOTH OF HYPERAMMONEMIA OR MUSCLE WASTING

RELATED APPLICATIONS

This application claims priority to U.S. Ser. No. 62/545,362 filed Aug. 14, 2017, U.S. Ser. No. 62/614,214 filed Jan. 5, 2018, and U.S. Ser. No. 62/697,772 filed Jul. 13, 2018, the contents of which are each incorporated herein by reference in their entireties.

BACKGROUND

An estimated 600,000 individuals in the US suffer from cirrhosis and 14,000 of these patients are in end-stage disease and await liver transplant. Studies have suggested that up to 40-60% of cirrhosis patients have concomitant muscle wasting. The resultant frailty is a significant cause for functional decline, cirrhosis-related complications, hospitalizations, and mortality in patients with end-stage liver disease (ESLD). Liver transplant is the definitive cure for ESLD, but physical decline, independent of liver disease severity, is associated with increased risk of de-listing from transplant waitlists.

An estimated 40-50% of cirrhosis patients exhibit cirrhotic sarcopenia. Cirrhotic sarcopenia is a frequent complication in cirrhosis that adversely impacts the survival and quality of life of patients. Cirrhotic sarcopenia is a systemic disease resulting from hyperammonemia due to a dysfunctional urea cycle in cirrhosis, in which the muscle detoxifies the ammonia, but at the expense of muscle mass. Sarcopenia lowers the survival, decreases the chances of receiving a transplant, and increases the risks of cirrhosis-related complications in cirrhosis patients.

The current standard of care for patients with cirrhosis, such as patients with ESLD or cirrhotic sarcopenia, include lifestyle modifications, such as increased exercise and dietary interventions. Currently, there are no approved pharmacological interventions.

Given the lack of available therapies, there is still a need for agents, e.g., dietary compositions and therapeutics for treating liver diseases and disorders with hyperammonemia or muscle wasting, such as cirrhosis, cirrhotic sarcopenia, ESLD, hepatic insufficiency, or hepatic encephalopathy.

SUMMARY

Provided herein is a composition (e.g., an Active Moiety) including amino acid entities that is useful for improving one, two, three, or more (e.g., all) of liver function, hyperammonemia, muscle mass, or muscle function in a subject, e.g., a subject with a liver disease or disorder with one or both of hyperammonemia or muscle wasting. The composition can be used in a method of treating (e.g., reversing, reducing, ameliorating, or preventing) a liver disease or disorder with one or both of hyperammonemia or muscle wasting (e.g., cirrhosis, e.g., cirrhotic sarcopenia, End Stage Liver Disease (ESLD), hepatic insufficiency, or hepatic encephalopathy) in a subject in need thereof (e.g, a human).

In one aspect, the invention features a composition comprising, consisting of, or consisting essentially of:

a) a Branched Chain Amino Acid (BCAA) entity chosen from a leucine amino acid entity, an isoleucine amino acid entity, a valine amino acid entity, or a combination of two or three BCAA entities;

b) a Urea Cycle Amino Acid (UCAA) entity chosen from an ornithine amino acid entity, an aspartate amino acid entity, or a combination of two UCAA entities; and c) an essential amino acid (EAA) entity chosen from a histidine amino acid entity, a lysine amino acid entity, or a threonine amino acid entity or a combination of two or three EAA entities;

wherein at least one amino acid entity (e.g., two, three, four, five, six, seven, or eight amino acid entities) of (a)-(c) is not provided as a peptide of more than 20 amino acid residues in length.

In some embodiments, the ornithine amino acid entity is chosen from L-ornithine, ornithine α-ketoglutarate, ornithine HCl, citrulline, or a combination thereof.

In some embodiments, one, two, or all of phenylalanine, tyrosine, and glutamine are absent from the composition, or if present, are present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form).

In some embodiments, the total wt. % of (a)-(c) (e.g., three, four, five, six, seven, or eight amino acid entities in (a)-(c)) is greater than the total wt. % of other protein components (e.g., whey protein) or non-protein components (or both) in the composition on a dry weight basis, e.g., the total wt. % (a)-(c) is at least: 50 wt. %, 75 wt. %, or 90 wt. % of the total wt. of amino acid entities or total components in the composition (in dry form).

In some embodiments, three, four, five, six, seven, or eight amino acid entities in (a)-(c) are in one or both of free amino acid form or salt amino acid form in the composition, e.g., at least: 35 wt. %, 40 wt. %, 42 wt. %, 45 wt. %, 50 wt. %, 75 wt. %, 80 wt. %, 90 wt. %, or more, of the total wt. of the composition (in dry form) is three, four, five, six, seven, or eight amino acid entities in (a)-(c) in one or both of free amino acid form or salt amino acid form in the composition.

In some embodiments, the composition comprises a combination of 19 or fewer, 18 or fewer, 15 or fewer, 12 or fewer, or 10 or fewer amino acid entities. In some embodiments, the combination comprises at least: 42 wt. %, 75 wt. %, or 90 wt. % of the total wt. of amino acid entities or total components in the composition (in dry form).

In some embodiments, one, two, or more (e.g., all) of phenylalanine, tyrosine, or glutamine is absent from the composition, or if present, are present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form). In some embodiments, one, two, or more (e.g., all) of phenylalanine, tyrosine, or glutamine, if present, are present in one or both of free amino acid form or salt amino acid.

In some embodiments, the wt. % of the BCAA entities is at least 37 wt. %, 38 wt. %, 39 wt. %, 40 wt. %, 41 wt. %, 42 wt. %, 43 wt. %, 44 wt. %, 45 wt. %, or more of the total wt. of amino acid entities or total components in the composition (in dry form).

In some embodiments, the wt. % of the UCAA entities is at least 25 wt. %, 26 wt. %, 27 wt. %, 28 wt. %, 29 wt. %, 30 wt. %, 31 wt. %, 32 wt. %, 33 wt. %, 34 wt. %, 35 wt. %, or more of the total wt. of amino acid entities or total components in the composition (in dry form).

In some embodiments, the wt. % of the EAA entities is at least 16 wt. %, 17 wt. %, 18 wt. %, 19 wt. %, 20 wt. %, or more of the total wt. of amino acid entities or total components in the composition (in dry form).

In some embodiments, the composition does not comprise a peptide of more than 20 amino acid residues in length (e.g., whey protein), or if a peptide of more than 20 amino acid residues in length is present, the peptide is present at less than: 10 weight (wt.) %, 5 wt. %, 1 wt. %, 0.5 wt. %, 0.1 wt. %, 0.05 wt. %, 0.01 wt. %, 0.001 wt. %, or less of the total wt. of amino acid entities or total components of the composition (in dry form).

In some embodiments, the composition has one, two, or three of the following features:

d) the wt. % of the combination of three of the BCAA entities is greater than the wt. % of the UCAA entity or the combination of two of the UCAA entities, e.g., the wt. % of the combination of three of the BCAA entities is at least 5% greater than the wt. % of the UCAA entity or the combination of two of the UCAA entities; e.g., the wt. % of the combination of three of the BCAA entities is at least 10%, 15%, 20%, or more greater than the wt. % of the UCAA entity or the combination of two of the UCAA entities;

e) the wt. % of the combination of three of the BCAA entities is greater than the wt. % of the EAA entity or the combination of two or three of the EAA entities in (c); e.g., the wt. % of the combination of three of the BCAA entities is at least 30% greater than the wt. % of the EAA entity or the combination of two or three of the EAA entities in (c); e.g., the wt. % of the combination of three of the BCAA entities is at least 40%, 50%, or 55%, or more greater than the wt. % of the EAA entity or the combination of two or three of the EAA entities in (c);

f) the wt. % of the combination of the UCAA entity or two of the UCAA entities is greater than the wt. % of the EAA entity or the combination of two or three of the EAA entities in (c); e.g., the wt. % of the UAA entity or the combination of two of the UCAA entities is at least 25% greater than the wt. % of the EAA entity or the combination of two or three of the EAA entities in (c); e.g., the wt. % of the UCAA entity or the combination of two of the UCAA entities is at least 30%, 35%, 40%, or more greater than the wt. % of the EAA entity or the combination of two or three of the EAA entities in (c); or g) a combination of two or three of (d)-(f).

In some embodiments, a wt. ratio of the BCAA entity or BCAA entities:the UCAA entity or UCAA entities:the EAA entity or EAA entities in (c) is 20+/−15%:15+/−15%:9+/−15%, where the ratios are determined based on an equivalent amount of each amino acid in free form.

In some embodiments, three, four, five, six, seven, or eight amino acid entities in (a)-(c) is selected from Table 1.

In some embodiments, the composition (e.g., the Active Moiety) comprises, consists of, or consists essentially of: a) a leucine amino acid entity chosen from: i) L-leucine or a salt thereof, ii) a dipeptide or salt thereof, or tripeptide or salt thereof, comprising L-leucine, or iii) β-hydroxy-β-methylbutyrate (HMB) or a salt thereof; b) one or both of: i) an ornithine amino acid entity chosen from L-ornithine or a salt thereof or a dipeptide or salt thereof, or tripeptide or salt thereof, comprising L-ornithine; or ii) an aspartate amino acid entity chosen from L-aspartate or a salt thereof or a dipeptide or salt thereof, or tripeptide or salt thereof, comprising L-aspartate; and c) an EAA entity chosen from: i) L-histidine or a salt thereof, ii) a dipeptide or salt thereof, or tripeptide or salt thereof, comprising L-histidine, iii) L-lysine or a salt thereof, iv) a dipeptide or salt thereof, or tripeptide or salt thereof, comprising L-lysine, v) L-threonine or a salt thereof, or vi) a dipeptide or salt thereof, or tripeptide or salt thereof, comprising L-threonine. In some embodiments, the composition further comprises one or both of an isoleucine amino acid entity or a valine amino acid entity, wherein one or both of the isoleucine amino acid entity or the valine amino acid entity is not provided as a peptide of more than 20 amino acid residues in length.

In some embodiments, the isoleucine amino acid-entity is L-isoleucine or a salt thereof or a dipeptide or salt thereof, or tripeptide or salt thereof, comprising L-isoleucine. In some embodiments, the valine amino acid-entity is L-valine or a salt thereof or a dipeptide or salt thereof, or tripeptide or salt thereof, comprising L-valine.

In some embodiments, a wt. ratio of the leucine amino acid entity:the isoleucine amino acid entity:the valine amino acid entity:the ornithine amino acid entity:the aspartate amino acid entity:the histidine amino acid entity:the threonine amino acid entity:the lysine amino acid entity is 8+/−20%:4+/−20%:8+/−20%:7.5+/−20%:7.5+/−20%:3+/−20%:3+/−20%:3+/−20%, where the ratios are determined based on an equivalent amount of each amino acid in free form.

In some embodiments, the composition comprises, consists of, or consists essentially of: L-leucine or a salt thereof, L-isoleucine or a salt thereof, L-valine or a salt thereof, L-ornithine or a salt thereof, L-aspartate or a salt thereof, L-histidine or a salt thereof, L-threonine or a salt thereof, and L-lysine or a salt thereof (e.g., L-lysine acetate).

In some embodiments, the composition (e.g., the Active Moiety) is formulated with a pharmaceutically acceptable carrier. In some embodiments, the composition (e.g., the Active Moiety) is formulated as a dietary composition. In some embodiments, the dietary composition is chosen from a medical food, a functional food, or a supplement.

In another aspect, the invention features a method of improving one, two, three, or more (e.g., all) of liver function, hyperammonemia, muscle mass, or muscle function, comprising administering to a subject with cirrhosis an effective amount of a composition (e.g., an Active Moiety) of any of the aspects or embodiments disclosed herein, thereby improving one, two, three, or more (e.g., all) of liver function, hyperammonemia, muscle mass, or muscle function.

Another aspect of the invention features a method of improving or treating a symptom selected from one, two, three, four, five, six, seven, eight, nine, 10, 11, 12, 13, 14, 15, 16, 17, or more (e.g., all) of hyperammonemia, ascites or complications associated with ascites, variceal bleeding, infection, hepatic encephalopathy, ammonia toxicity, hepatic insufficiency, decreased urea synthesis, inflammation of hepatic tissue, fibrosis, cirrhosis, muscle wasting, muscle catabolism, muscle atrophy, hypoalbuminemia, malnutrition, frailty, or coagulopathy, comprising administering to a subject in need thereof an effective amount of a composition (e.g., an Active Moiety) of any of the aspects or embodiments disclosed herein, thereby improving or treating the symptom in the subject.

In another aspect, the invention features a method for treating or preventing a liver disease or disorder characterized by one or both of hyperammonemia or muscle wasting, comprising administering to a subject in need thereof an effective amount of a composition (e.g., an Active Moiety) of any of the aspects or embodiments disclosed herein, thereby treating the liver disease or disorder or muscle wasting in the subject.

In some embodiments, the subject has cirrhosis. In some embodiments, the subject has cirrhotic sarcopenia. In some embodiments, the subject has hepatic insufficiency. In some embodiments, the subject has End Stage Liver Disease. In some embodiments, the subject has hepatic encephalopathy.

In some embodiments, administration of the composition results in one, two, three, four, five, six, seven, eight, nine, ten, or more (e.g., all) of: a) increased level of BCAAs; b) decreased level of aromatic amino acids (AAAs); c) decreased level of ammonia; d) increased level of protein, e.g., increased protein synthesis; e) increased activation of mTORC1; f) decreased level of myostatin; g) decreased level of creatinine; h) increased level of albumin; i) decreased level of bilirubin; j) increased Fischer's ratio (e.g., increased level of BCAAs relative to the level of AAAs); or k) an increased level of valine relative to a level of phenylalanine.

DETAILED DESCRIPTION

Described herein, in part, is a composition (e.g., an Active Moiety) comprising amino acid entities and methods of improving one, two, three, or four of liver function, hyperammonemia, muscle mass, or muscle function by administering an effective amount of the composition. The composition can be administered to treat or prevent a liver disease or disorder with one or both of hyperammonemia or muscle wasting in a subject in need thereof.

Sarcopenia is a significant complication of cirrhosis and is associated with overall mortality in patients with end-stage liver disease. Limited therapies aimed at ameliorating sarcopenia in cirrhosis are available despite the fact that decreased muscle mass represents a significant risk-factor for other complications of cirrhosis, such as ascites, infection, and hepatic encephalopathy. As the liver is an important tissue for amino acid homeostasis, amino acid profiles are perturbed in patients with cirrhosis, which further exacerbates muscle wasting and cirrhosis-associated complications. The amino acid entities and relative amounts of the amino acid entities in the compositions disclosed herein have been optimized, e.g., to improve liver function, hyperammonemia, muscle function, muscle mass, and reduce complications associated with liver dysfunction (e.g., ascites, infection, or hepatic encephalopathy) in a subject that requires the coordination of many biological, cellular, and molecular processes. In some embodiments, the compositions disclosed herein improve ammonia detoxification within one or both of muscle or blood, while stimulating muscle anabolism, e.g., by improving the amino acid profile of a subject with a liver disease or disorder, such as cirrhosis.

Figure 1:
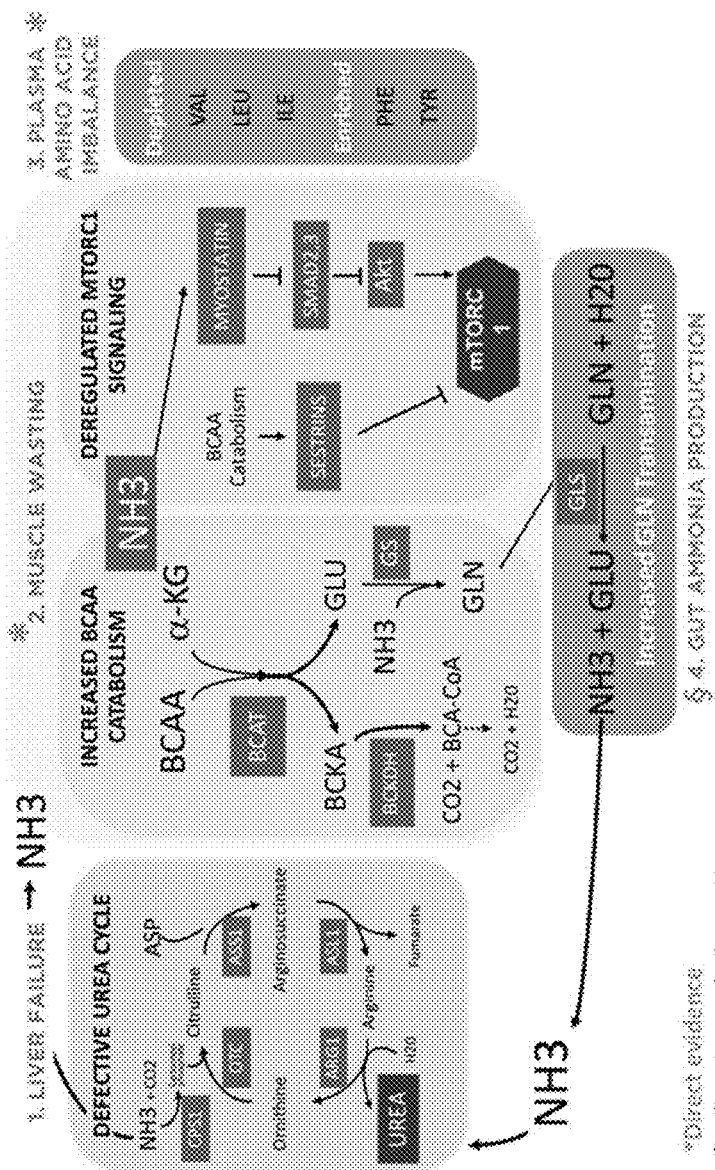
FIG. 1 is a schematic showing how the composition of the invention can reprogram the disordered multifactorial cascade of ammonia-induced muscle wasting in liver diseases and disorders, such as cirrhosis, by improving one, two, three, or four of a defective urea cycle, muscle wasting, plasma amino acid imbalance, or gut ammonia production.

Without being bound by any theory, it is understood that a composition of the invention can reprogram the disordered multifactorial cascade of ammonia-induced muscle wasting in liver diseases and disorders, such as cirrhosis, to improve one of more of: 1) a defective urea cycle (e.g., resulting in liver failure); 2) muscle wasting as a result of one or both of increased BCAA catabolism or deregulated mTORC1 signaling; 3) amino acid imbalance (e.g., a depletion of valine, isoleucine, and isoleucine with an enrichment of phenylalanine and tyrosine in plasma); and 4) gut ammonia production (e.g., as a result of increased glutamine transamination) (see FIG. 1). Similarly, administration of a composition of the invention can result in one, two, three or all of increase the Fischer's ratio (e.g., the ratio of a level of BCAAs to a level of AAAs), increase the valine to phenylalanine ratio, improve body composition toward a leaner phenotype, and improve the utilization of amino acids towards muscle protein synthesis, e.g., to lower ammonia levels, in a subject.

In some embodiments, a Fischer's ratio (e.g., the ratio of a level of BCAAs to a level of AAAs) is used to determine the plasma amino acid imbalance in a subject, e.g., to assess one or both of liver metabolism or the severity of liver dysfunction in a subject. In Example 1 described in detail below, a composition of the invention improved the Fischer's ratio of a human subject with mild to moderate hepatic insufficiency.

An increase in a level of valine to a level of phenylanine (e.g., the valine to phenylalanine ratio) can be indicative of one or both of increased protein synthesis or a decreased level of ammonia in a subject. In Example 1 described in detail below, a composition of the invention improved the valine to phenylalanine ratio of a human subject with mild to moderate hepatic insufficiency.

In certain embodiments, a level of ammonia in the subject is negatively correated with one or both of the Fischer's ratio or valine to phenylalanine ratio of the subject. A negative correlation between a level of ammonia and the Fischer's ratio or the valine to phenylalanine ratio of a subject can be indicative of ammonia consumption during muscle protein synthesis.

Definitions

Terms used in the claims and specification are defined as set forth below unless otherwise specified.

It must be noted that, as used in the specification and the appended claims, the singular forms "a," "an" and "the" include plural referents unless the context clearly dictates otherwise.

As used herein, the term "amino acid entity" refers to an amino acid in one or both of free form or salt form, an amino acid residue of a peptide (e.g., of a dipeptide, tripeptide, oligopeptide, or polypeptide), a derivative of an amino acid, a precursor of an amino acid, or a metabolite of an amino acid.

As used herein the term "XXX amino acid entity" refers to an amino acid entity that if a free amino acid, comprises free XXX or XXX in salt form; if a peptide, refers to a peptide (e.g., a dipeptide or a tripeptide) comprising an XXX residue; if a derivative, refers to a derivative of XXX; if a precursor, refers to a precursor of XXX; and if a metabolite, refers to a XXX metabolite (Table 1).

TABLE 1

Amino acid entities include amino acids, precursors, metabolites, and derivatives of the compositions described herein.

| Exemplary Amino Acid | Precursors | Metabolites | Derivatives | Salts |
|---|---|---|---|---|
| Leucine | L-Leucine | Oxo-leucine (Alpha-ketoisocaproate (KIC)) | HMB (beta-hydroxy-beta-methylbutyrate); Oxo-leucine; Isovaleryl-CoA | N-Acetyl-Leucine; | |
| Isoleucine | L-Isoleucine | 2-Oxo-3-methyl-valerate (Alpha-keto-beta-methylvaleric acid (KMV)); Threonine | 2-Oxo-3-methyl-valerate; Methylbutyryl-CoA | N-Acetyl-Isoleucine | |
| Valine | L-Valine | 2-Oxo-valerate (alpha-ketoisovalerate (KIV) | Isobutryl-CoA | N-Acetyl-Valine | |
| Ornithine | L-Ornithine | L-Arginine, Glycine | Citrulline | | Ornithine α-ketoglutarate, Ornithine HCl |
| Aspartate | L-Aspartate | Fumarate | Adenylosuccinate | | |
| Histidine | L-Histidine | Histidinol; Histidinal; Ribose-5-phosphate | Carnosine; Histamine; Urocanate | N-Acetyl-Histidine | |
| Lysine | L-Lysine | Diaminopimelate; Aspartate | Trimethylhistidine amino acid entity; Carnitine; Saccharopine | N-Acetyl-Lysine | L-Lysine Acetate |
| Threonine | L-Threonine | Homoserine; O-PhosphoHomoserine | Oxobutyrate | N-Acetyl-Threonine | |

For example, where XXX is leucine (L), then leucine amino acid entity refers to free L or L in salt form, a peptide (e.g., a dipeptide or a tripeptide) comprising a L residue, a L derivative, a L precursor, or a metabolite of L; where XXX is isoleucine(I), then isoleucine amino acid entity refers to free I or I in salt form, a peptide (e.g., a dipeptide or a tripeptide) comprising a I residue, a I derivative, a I precursor, or a metabolite of I; where XXX is valine (V), then valine amino acid entity refers to free V or V in salt form, a peptide (e.g., a dipeptide or a tripeptide) comprising a V residue, a V derivative, a V precursor, or a metabolite of V; where XXX is ornithine (Orn), then ornithine amino acid entity refers to free Orn or Orn in salt form, a peptide (e.g., a dipeptide or a tripeptide) comprising a Orn residue, a Orn derivative, a Orn precursor, or a metabolite of Orn; where XXX is aspartate (D), then aspartate amino acid entity refers to free D or D in salt form, a peptide (e.g., a dipeptide or a tripeptide) comprising a D residue, a D derivative, a D precursor, or a metabolite of D; where XXX is histidine (H), then histidine amino acid entity refers to free H or H in salt form, a peptide (e.g., a dipeptide or a tripeptide) comprising a H residue, a H derivative, a H precursor, or a metabolite of H; where XXX is lysine (K), then lysine amino acid entity refers to free K or K in salt form, a peptide (e.g., a dipeptide or a tripeptide) comprising a K residue, a K derivative, a K precursor, or a metabolite of K; and where XXX is threonine (T), then threonine amino acid entity refers to free T or T in salt form, a peptide (e.g., a dipeptide or a tripeptide) comprising a T residue, a T derivative, a T precursor, or a metabolite of T.

"About" and "approximately" shall generally mean an acceptable degree of error for the quantity measured given the nature or precision of the measurements. Exemplary degrees of error are within 15 percent (%), typically, within 10%, and more typically, within 5% of a given value or range of values.

An "amino acid" refers to an organic compound having an amino group ($-NH_2$), a carboxylic acid group ($-C(=O)OH$), and a side chain bonded through a central carbon atom, and includes essential and non-essential amino acids, as well as natural and unnatural amino acids. Unless otherwise indicated, amino acids referred to herein are L-isomers of amino acids.

As used herein, the term "Active Moiety" means a combination of four or more amino acid entities that, in aggregate, have the ability to have a physiological effect as described herein, e.g., improving one, two, three, or more (e.g., all) of liver function, hyperammonemia, muscle mass, or muscle function. For example, an Active Moiety can treat a liver disease or disorder with one or both of hyperammonemia or muscle wasting. An Active Moiety of the invention can contain other biologically active ingredients. In some examples, the Active Moiety comprises a defined combination of three or more amino acid entities, as set out in detail below. In other embodiments, the Active Moiety consists of a defined combination of three or more amino acid entities, as set out in detail below.

The individual amino acid entities are present in the composition, e.g., Active Moiety, in various amounts or ratios, which can be presented as amount by weight (e.g., in grams), ratio by weight of amino acid entities to each other, amount by mole, amount by weight percent of the composition, amount by mole percent of the composition, caloric content, percent caloric contribution to the composition, etc. Generally, this disclosure will provide grams of amino acid entity in a dosage form, weight percent of an amino acid entity relative to the weight of the composition, i.e., the weight of all the amino acid entities and any other biologically active ingredient present in the composition, or in ratios. In some embodiments, the composition, e.g., Active Moiety, is provided as a pharmaceutically acceptable preparation (e.g., a pharmaceutical product).

The term "effective amount" as used herein means an amount of an active of the invention in a composition of the invention, particularly a pharmaceutical composition of the invention, which is sufficient to reduce a symptom and/or improve a condition to be treated (e.g., provide a desired clinical response). The effective amount of an active for use in a composition will vary with the particular condition being treated, the severity of the condition, the duration of treatment, the nature of concurrent therapy, the particular active being employed, the particular pharmaceutically-acceptable excipient(s) and/or carrier(s) utilized, and like factors with the knowledge and expertise of the attending physician.

An "equivalent amount" of an amino acid entity is an amount that yields, physiologically, the same activity as that amount of the corresponding free amino acid for the amino acid entity.

A "pharmaceutical composition" described herein comprises at least one "Active Moiety" and a pharmaceutically acceptable carrier or excipient. In some embodiments, the pharmaceutical composition is used as a therapeutic. Other compositions, which need not meet pharmaceutical standards (GMP; pharmaceutical grade components) can be used as a nutraceutical, a medical food, or as a supplement, these are termed "consumer health compositions".

The term "pharmaceutically acceptable" as used herein, refers to amino acids, materials, excipients, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In a specific embodiment, "pharmaceutically acceptable" means free of detectable endotoxin or endotoxin levels are below levels acceptable in pharmaceutical products.

In a specific embodiment, "pharmaceutically acceptable" means a standard used by the pharmaceutical industry or by agencies or entities (e.g., government or trade agencies or entities) regulating the pharmaceutical industry to ensure one or more product quality parameters are within acceptable ranges for a medicine, pharmaceutical composition, treatment, or other therapeutic. A product quality parameter can be any parameter regulated by the pharmaceutical industry or by agencies or entities, e.g., government or trade agencies or entities, including but not limited to composition; composition uniformity; dosage; dosage uniformity; presence, absence, and/or level of contaminants or impurities; and level of sterility (e.g., the presence, absence and/or level of microbes). Exemplary government regulatory agencies include: Federal Drug Administration (FDA), European Medicines Agency (EMA), SwissMedic, China Food and Drug Administration (CFDA), or Japanese Pharmaceuticals and Medical Devices Agency (PMDA).

The term "pharmaceutically acceptable excipient" refers to an ingredient in a pharmaceutical formulation, other than an active, which is physiologically compatible. A pharmaceutically acceptable excipient can include, but is not limited to, a buffer, a sweetener, a dispersion enhancer, a flavoring agent, a bitterness masking agent, a natural coloring, an artificial coloring, a stabilizer, a solvent, or a preservative. In a specific embodiment, a pharmaceutically acceptable excipient includes one or both of citric acid or lecithin.

The term "protein component," as used herein, refers to a peptide (e.g., a polypeptide or an oligopeptide), a fragment thereof, a degraded peptide, an amino acid entity or a free amino acid. A protein component includes an amino acid in free form or salt form, a dipeptide of an amino acid, a tripeptide of an amino acid, a derivative of an amino acid, a precursor of an amino acid, or a metabolite of an amino acid. Exemplary protein components include, but are not limited to, one or more of whey protein, egg white protein, soy protein, casein, hemp protein, pea protein, brown rice protein, or a fragment or degraded peptide thereof.

The term "non-protein component," as used herein, refers to any component of a composition other than a protein component. Exemplary non-protein components can include, but are not limited to, a saccharide (e.g., a monosaccharide (e.g., dextrose, glucose, or fructose), a disaccharide, an oligosaccharide, or a polysaccharide); a lipid (e.g., a sulfur-containing lipid (e.g., alpha-lipoic acid), a long chain triglyceride, an omega 3 fatty acid (e.g., EPA, DHA, STA, DPA, or ALA), an omega 6 fatty acid (GLA, DGLA, or LA), a medium chain triglyceride, or a medium chain fatty acid); a vitamin (e.g., vitamin A, vitamin E, vitamin C, vitamin D, vitamin B6, vitamin B12, biotin, or pantothenic acid); a mineral (zinc, selenium, iron, copper, folate, phosphorous, potassium, manganese, chromium, calcium, or magnesium); or a sterol (e.g., cholesterol).

A composition, formulation or product is "therapeutic" if it provides a desired clinical effect. A desired clinical effect can be shown by lessening the progression of a disease and/or alleviating one or more symptoms of the disease.

A "unit dose" or "unit dosage" comprises the drug product or drug products in the form in which they are marketed for use, with a specific mixture of the active and inactive components (excipients), in a particular configuration (e.g, a capsule shell, for example), and apportioned into a particular dose (e.g., in multiple stick packs).

As used herein, the terms "treat," "treating," or "treatment" of liver disease or disorder or muscle wasting refers to ameliorating a liver disease or disorder with one or both of hyperammonemia or muscle wasting (e.g., slowing, arresting, or reducing the development of the liver disease or disorder with one or both of hyperammonemia or muscle wasting or at least one of the clinical symptoms thereof); alleviating or ameliorating at least one physical parameter including those which may not be discernible by the patient; and/or preventing or delaying the onset or development or progression of a liver disease or disorder with one or both of hyperammonemia or muscle wasting.

Compositions Comprising Amino Acid Entities

The composition of the invention as described herein (e.g., an Active Moiety) comprises amino acid entities, e.g., the amino acid entities shown in Table 1.

In certain embodiments, the leucine amino acid entity is chosen from Table 1, e.g., the leucine amino acid entity is chosen from L-leucine, β-hydroxy-β-methylbutyrate (HMB), oxo-leucine (alpha-ketoisocaproate (KIC)), isovaleryl-CoA, n-acetylleucine, or a combination thereof. In certain embodiments, the leucine amino acid entity is chosen from L-leucine, oxo-leucine (KIC), isovaleryl-CoA, n-acetyl-leucine, or a combination thereof.

In certain embodiments, the isoleucine amino acid entity is chosen from Table 1, e.g., the isoleucine amino acid entity is chosen from L-isoleucine, 2-oxo-3-methyl-valerate (alpha-keto-beta-methylvaleric acid (KMV)), threonine, methylbutyryl-CoA, D-isoleucine, N-acetyl-isoleucine, or a combination thereof.

In certain embodiments, the valine amino acid entity is chosen from Table 1, e.g., the valine amino acid entity is chosen from L-valine, 2-oxo-valerate (alpha-ketoisovalerate (KIV)), isobutyryl-CoA, N-acetyl-valine, or a combination thereof.

In certain embodiments, the ornithine amino acid entity is chosen from Table 1, e.g., the ornithine amino acid entity is chosen from L-ornithine, ornithine α-ketoglutarate, ornithine HCl, L-arginine, glycine, citrulline, or a combination thereof. In certain embodiments, the ornithine amino acid entity is chosen from L-ornithine, ornithine α-ketoglutarate, ornithine HCl, citrulline, or a combination thereof. In certain embodiments, the ornithine amino acid entity is chosen from L-ornithine, ornithine HCl, citrulline, or a combination thereof.

In certain embodiments, the aspartate amino acid entity is chosen from Table 1, e.g., the aspartate amino acid entity is chosen from L-aspartate, fumarate, adenylosuccinate, or a combination thereof.

In certain embodiments, the histidine amino acid entity is chosen from Table 1, e.g., the histidine amino acid entity is chosen from L-histidine, histidinol, histidinal, ribose-5-phosphate, carnosine, histamine, urocanate, and N-acetyl-histidine, or a combination thereof.

In certain embodiments, the lysine amino acid entity is chosen from Table 1, e.g., the lysine amino acid entity is chosen from L-lysine, diaminopimelate, aspartate, trimethylhistidine amino acid entity, carnitine, saccharopine, N-acetyl-lysine, or a combination thereof.

In certain embodiments, the threonine amino acid entity is chosen from Table 1, e.g., the threonine amino acid entity is chosen from L-threonine, homoserine, O-phosphohomoserine, oxobutyrate, N-acetyl-threonine, or a combination thereof.

In some embodiments, one, two, or three of (a) a leucine amino acid entity, an isoleucine amino acid entity, or a valine amino acid entity is in free amino acid form. In some embodiments, one, two, or three of (a) a leucine amino acid entity, an isoleucine amino acid entity, a valine amino acid entity is in salt amino acid form.

In some embodiments, one or both of (b) an ornithine amino acid entity or an aspartate amino acid entity is in free amino acid form. In some embodiments, one or both of (b) ornithine amino acid entity or an aspartate amino acid entity is in salt amino acid form (e.g., L-ornithine or a salt thereof and L-aspartate or a salt thereof are present in combination as a salt (LOLA)).

In some embodiments, one, two, or three of (c) a histidine amino acid entity, a lysine amino acid entity, or a threonine amino acid entity is in free amino acid form. In some embodiments, one, two, or three of (c) a histidine amino acid entity, a lysine amino acid entity, or a threonine amino acid entity is in salt amino acid form (e.g., L-lysine or a salt thereof is present as L-lysine acetate).

In some embodiments, at least: 35 wt. %, 40 wt. %, 42 wt. %, 45 wt. %, 50 wt. %, 55 wt. %, 60 wt. %, 70 wt. %, 80 wt. %, or more, of the total wt. of the composition (in dry form) is three, four, five, six, seven, or eight amino acid entities in (a)-(c) in free amino acid form. In some embodiments, at least: 15 wt. %, 20 wt. %, 25 wt. %, 35 wt. %, 40 wt. %, or more, of the total wt. of the composition (in dry form) is three, four, five, six, seven, or eight amino acid entities in (a)-(c) in salt form.

In some embodiments, three, four, five, six, seven, or eight amino acid entities in (a)-(c) is provided as part of a dipeptide or tripeptide, e.g., in an amount of at least: 0.01 wt. %, 0.1 wt. %, 0.5 wt. %, 1 wt. %, 5 wt. %, or 10 wt. %, or more of amino acid entities or total components of the composition.

In some embodiments, the composition further comprises L-alanine, L-arginine, L-tryptophan, carnitine, sodium acetate, or a combination thereof. In some embodiments, the composition further comprises a mineral, e.g., zinc. In some embodiments, the composition further comprises a vitamin, e.g., one, two, or three of vitamin A, vitamin D, vitamin E, or a combination thereof. In some embodiments, the composition further comprises an ammonia scavenger, e.g., phenyl acetate, acetyl-L-carnitine, citrulline, sodium benzoate, sodium phenylbutyrate, or a combination thereof.

In some embodiments, the composition can include sulfur AAs (SAAs), such as N-acetylcysteine (NAC). In an embodiment, the SAA (e.g., NAC) has anti-oxidant activity. In an embodiment, the SAA (e.g., NAC) results in decreased reactive oxygen species (ROS) or increased glutathione (GSH) in a subject administered the composition described herein.

In some embodiments, the composition comprises, consists of, or consists essentially of: a leucine amino acid entity, an isoleucine amino acid entity, valine amino acid entity, an ornithine amino acid entity, an aspartate amino acid entity, a histidine amino acid entity, a threonine amino acid entity, and a lysine amino acid entity.

In some embodiments, the composition (e.g., the Active Moiety) comprises, consists of, or consists essentially of: a) a leucine amino acid entity; b) an ornithine amino acid entity; and c) an essential amino acid (EAA)-entity chosen from a histidine amino acid entity, a lysine amino acid entity, or a threonine amino acid entity or a combination of two or three EAA entities; wherein at least one amino acid entity (e.g., two, three, four, or five amino acid entities) of (a)-(c) is not provided as a peptide of more than 20 amino acid residues in length.

In some embodiments, the composition (e.g., the Active Moiety) comprises, consists of, or consists essentially of: a) a leucine amino acid entity and a valine amino acid entity; b) an ornithine amino acid entity; and c) an essential amino acid (EAA)-entity chosen from a histidine amino acid entity, a lysine amino acid entity, or a threonine amino acid entity or a combination of two or three EAA entities; wherein at least one amino acid entity (e.g., two, three, four, or five amino acid entities) of (a)-(c) is not provided as a peptide of more than 20 amino acid residues in length. In some embodiments, the composition further comprises an isoleucine amino acid entity. In some embodiments, the composition further comprises an aspartate amino acid entity.

In some embodiments, the composition (e.g., the Active Moiety) comprises, consists of, or consists essentially of: a) a leucine amino acid entity, an isoleucine amino acid entity, and a valine amino acid entity; b) an ornithine amino acid entity; and c) an essential amino acid (EAA)-entity chosen from a histidine amino acid entity, a lysine amino acid entity, or a threonine amino acid entity or a combination of two or three EAA entities; wherein at least one amino acid entity (e.g., two, three, four, five, six, or seven amino acid entities) of (a)-(c) is not provided as a peptide of more than 20 amino acid residues in length. In some embodiments, the composition further comprises an aspartate amino acid entity.

In some embodiments, one, two, three, four, five, six, seven, or eight of the leucine amino acid entity, the isoleucine amino acid entity, the valine amino acid entity, the ornithine amino acid entity, the aspartate amino acid entity, the histidine amino acid entity, the lysine amino acid entity, or the threonine amino acid entity is provided as part of a dipeptide (e.g., a homodipeptide or heterodipeptide) or salt thereof. In some embodiments, the leucine amino acid entity is Ala-Leu. In some embodiments, one, two, three, four, five, six, seven, or eight of the leucine amino acid entity, the isoleucine amino acid entity, the valine amino acid entity, the ornithine amino acid entity, the aspartate amino acid entity, the histidine amino acid entity, the lysine amino acid entity, or the threonine amino acid entity is provided as part of a tripeptide (e.g., a homotripeptide or heterotripeptide) or salt thereof.

In some embodiments, the composition is capable of one, two, three, four, five, six, seven, eight, nine, or all (e.g., more) of: a) increasing a level of branched chain amino acids (BCAAs); b) decreasing a level of aromatic amino acids (AAAs); c) decreasing a level of ammonia; d) increasing a level of protein, e.g., increased protein synthesis; e) increasing activation of mTORC1; f) decreasing a level of myostatin; g) decreasing a level of creatinine; h) increasing a level of albumin; i) decreasing a level of bilirubin; j) restoring a Fischer's ratio (e.g., increasing the level of BCAAs relative to the level of AAAs); or k) increasing a level of valine relative to a level of phenylalanine.

In some embodiments the composition is capable of increasing, or increases, albumin production, e.g., by at least 50%, 60%, or 70%, as detected using an assay of albumin, e.g., in HepG2 hepatocellular carcinoma cells, e.g., using an antibody-based detection assay, e.g., an ELISA, e.g., as described in Example 9, e.g., relative to a reference composition (e.g., an amino acid composition comprising L-leucine alone; L-ornithine and L-aspartate in combination; L-histidine, L-lysine, and L threonine in combination; L-ornithine, L-aspartate, L-histidine, L-lysine, and L-threonine in combination; or L-leucine, L-isoleucine, and L-valine in combination).

In some embodiments the composition is capable of decreasing, or decreases, atrophy by at least 10%, 25%, 30%, 40%, 50%, or 60%, as detected using an assay of TNFα, e.g., in myotubes, e.g., using the MYOSCREEN™ platform, e.g., as described in Example 10, e.g., relative to a reference composition (e.g., an amino acid composition comprising L-histidine, L-lysine, and L-threonine in combination; L-leucine, L-isoleucine, L-valine, L-histidine, L-lysine, L-threonine, L-phenylalanine, L-methionine, and L-tryptophan in combination; L-ornithine, L-aspartate, L-histidine, L-lysine, and L-threonine in combination; L-ornithine, L-aspartate, L-leucine, L-isoleucine, L-valine, L-histidine, L-lysine, L-threonine, L-phenylalanine, L-methionine, and L-tryptophan in combination; or L-aspartate, L-leucine, L-isoleucine, L-valine, L-histidine, L-lysine, L-threonine, L-phenylalanine, L-methionine, and L-tryptophan in combination).

i. Amounts

An exemplary composition (e.g., an Active Moiety) can include 0.89 g of leucine or the equivalent amount of a leucine amino acid entity, 0.44 g of isoleucine or the equivalent amount of an isoleucine amino acid entity, 0.89 g of valine or the equivalent amount of a valine amino acid entity, 0.33 g of lysine or the equivalent amount of a lysine amino acid entity, 0.33 g of histidine or the equivalent amount of a histidine amino acid entity, 0.33 g of threonine or the equivalent amount of a threonine amino acid entity, 0.83 g of ornithine or the equivalent amount of an ornithine amino acid entity, and 0.83 g aspartate or the equivalent amount of an aspartate amino acid entity (see, e.g., packet (g) in Table 2).

TABLE 2

Exemplary composition comprising amino acids (e.g., an Active Moiety).

| Amino Acid | Packet (g) | Dose (g) (TID) | Total Daily (g) | Wt. Ratio | Wt. % (not including Acetate in L-Lysine) | Wt. % (including Acetate in L-Lysine) |
|---|---|---|---|---|---|---|
| L-Leucine | 0.89 | 2.67 | 8 | 8 | 18.2 | 17.7 |
| L-Isoleucine | 0.44 | 1.33 | 4 | 4 | 9.1 | 8.8 |
| L-Valine | 0.89 | 2.67 | 8 | 8 | 18.2 | 17.7 |
| L-Lysine (L-Lysine Acetate) | 0.33 (0.47 in salt form) | 1 (1.41 in salt form) | 3 (4.2 in salt form) | 3 (4.2 in salt form) | 6.8 | 9.4 |
| L-Histidine | 0.33 | 1 | 3 | 3 | 6.8 | 6.6 |
| L-Threonine | 0.33 | 1 | 3 | 3 | 6.8 | 6.6 |
| L-Ornithine | 0.83 | 2.5 | 7.5 | 7.5 | 17.1 | 33.2 |
| L-Aspartate | 0.83 | 2.5 | 7.5 | 7.5 | 17.1 | 17.7 |
| Total amino acids | 4.9 (5 with L-lysine acetate) | 14.7 (15.1 with L-lysine acetate) | 44 (45.2 with L-lysine acetate) | | 100 | 100 |

TABLE 2-continued

Exemplary composition comprising amino acids (e.g., an Active Moiety).

| Amino Acid | Packet (g) | Dose (g) (TID) | Total Daily (g) | Wt. Ratio | Wt. % (not including Acetate in L-Lysine) | Wt. % (including Acetate in L-Lysine) |
|---|---|---|---|---|---|---|
| Total BCAA | 2.23 | 6.67 | 20 | 20 | 45.5 | 44.2 |
| Total EAA | 1 | 3 | 9 | 9 | 20.4 | 22.6 |
| Total UCAA | 1.66 | 5 | 15 | 15 | 34.2 | 50.9 |
| Total UCAA + BCAA | 3.88 | 11.67 | 35 | 35 | 79.7 | 95.1 |

In some embodiments, the composition includes 0.89 g+/−20% of leucine or the equivalent amount of a leucine amino acid entity, 0.44 g+/−20% of isoleucine or the equivalent amount of an isoleucine amino acid entity, 0.89 g+/−20% of valine or the equivalent amount of a valine amino acid entity, 0.33 g+/−20% of lysine or the equivalent amount of a lysine amino acid entity, 0.33 g+/−20% of histidine or the equivalent amount of a histidine amino acid entity, 0.33 g+/−20% of threonine or the equivalent amount of a threonine amino acid entity, 0.83 g+/−20% of ornithine or the equivalent amount of an ornithine amino acid entity, and 0.83 g+/−20% aspartate or the equivalent amount of an aspartate amino acid entity.

In some embodiments, the composition includes 0.89 g+/−15% of leucine or the equivalent amount of a leucine amino acid entity, 0.44 g+/−15% of isoleucine or the equivalent amount of an isoleucine amino acid entity, 0.89 g+/−15% of valine or the equivalent amount of a valine amino acid entity, 0.33 g+/−15% of lysine or the equivalent amount of a lysine amino acid entity, 0.33 g+/−15% of histidine or the equivalent amount of a histidine amino acid entity, 0.33 g+/−15% of threonine or the equivalent amount of a threonine amino acid entity, 0.83 g+/−15% of ornithine or the equivalent amount of an ornithine amino acid entity, and 0.83 g+/−15% aspartate or the equivalent amount of an aspartate amino acid entity.

In some embodiments, the composition includes 0.89 g+/−10% of leucine or the equivalent amount of a leucine amino acid entity, 0.44 g+/−10% of isoleucine or the equivalent amount of an isoleucine amino acid entity, 0.89 g+/−10% of valine or the equivalent amount of a valine amino acid entity, 0.33 g+/−10% of lysine or the equivalent amount of a lysine amino acid entity, 0.33 g+/−10% of histidine or the equivalent amount of a histidine amino acid entity, 0.33 g+/−10% of threonine or the equivalent amount of a threonine amino acid entity, 0.83 g+/−10% of ornithine or the equivalent amount of an ornithine amino acid entity, and 0.83 g+/−10% aspartate or the equivalent amount of an aspartate amino acid entity.

In some embodiments, the composition includes 0.89 g+/−5% of leucine or the equivalent amount of a leucine amino acid entity, 0.44 g+/−5% of isoleucine or the equivalent amount of an isoleucine amino acid entity, 0.89 g+/−5% of valine or the equivalent amount of a valine amino acid entity, 0.33 g+/−5% of lysine or the equivalent amount of a lysine amino acid entity, 0.33 g+/−5% of histidine or the equivalent amount of a histidine amino acid entity, 0.33 g+/−5% of threonine or the equivalent amount of a threonine amino acid entity, 0.83 g+/−5% of ornithine or the equivalent amount of an ornithine amino acid entity, and 0.83 g+/−5% aspartate or the equivalent amount of an aspartate amino acid entity.

An exemplary composition (e.g., an Active Moiety) can include 0.89 g of leucine or the equivalent amount of a leucine amino acid entity, 0.44 g of isoleucine or the equivalent amount of an isoleucine amino acid entity, 0.89 g of valine or the equivalent amount of a valine amino acid entity, 0.33 g of lysine or the equivalent amount of a lysine amino acid entity, 0.33 g of histidine or the equivalent amount of a histidine amino acid entity, 0.33 g of threonine or the equivalent amount of a threonine amino acid entity, and 0.83 g of ornithine or the equivalent amount of an ornithine amino acid entity (see, e.g., packet (g) in Table 3).

TABLE 3

Exemplary composition comprising amino acids (e.g., an Active Moiety).

| Amino Acid | Packet (g) | Dose (g) (TID) | Total Daily (g) | Wt. Ratio | Wt. % |
|---|---|---|---|---|---|
| L-Leucine | 0.89 | 2.67 | 8 | 8 | 21.3 |
| L-Isoleucine | 0.44 | 1.33 | 4 | 4 | 10.5 |
| L-Valine | 0.89 | 2.67 | 8 | 8 | 21.3 |
| L-Lysine (L-Lysine Acetate) | 0.33 (0.47 in salt form) | 1 (1.41 in salt form) | 3 (4.2 in salt form) | 3 (4.2 in salt form) | 11.2 |
| L-Histidine | 0.33 | 1 | 3 | 3 | 7.9 |
| L-Threonine | 0.33 | 1 | 3 | 3 | 7.9 |
| L-Ornithine | 0.83 | 2.5 | 7.5 | 7.5 | 19.9 |
| Total amino acids | 4.0 (4.2 with L-lysine acetate) | 12.2 (12.6 with L-lysine acetate) | 36.5 (37.7 with L-lysine acetate) | | 100 |
| Total BCAA | 2.23 | 6.67 | 20 | | |
| Total EAA | 1 | 3 | 9 | | |

In some embodiments, the composition includes 0.89 g+/−20% of leucine or the equivalent amount of a leucine amino acid entity, 0.44 g+/−20% of isoleucine or the equivalent amount of an isoleucine amino acid entity, 0.89 g+/−20% of valine or the equivalent amount of a valine amino acid entity, 0.33 g+/−20% of lysine or the equivalent amount of a lysine amino acid entity, 0.33 g+/−20% of histidine or the equivalent amount of a histidine amino acid entity, 0.33 g+/−20% of threonine or the equivalent amount of a threonine amino acid entity, and 0.83 g+/−20% of ornithine or the equivalent amount of an ornithine amino acid entity.

In some embodiments, the composition includes 0.89 g+/−15% of leucine or the equivalent amount of a leucine amino acid entity, 0.44 g+/−15% of isoleucine or the equivalent amount of an isoleucine amino acid entity, 0.89 g+/−15% of valine or the equivalent amount of a valine amino acid entity, 0.33 g+/−15% of lysine or the equivalent amount of a lysine amino acid entity, 0.33 g+/−15% of histidine or the equivalent amount of a histidine amino acid entity, 0.33 g+/−15% of threonine or the equivalent amount of a threonine amino acid entity, and 0.83 g+/−15% of ornithine or the equivalent amount of an ornithine amino acid entity.

In some embodiments, the composition includes 0.89 g+/−10% of leucine or the equivalent amount of a leucine amino acid entity, 0.44 g+/−10% of isoleucine or the equivalent amount of an isoleucine amino acid entity, 0.89 g+/−10% of valine or the equivalent amount of a valine amino acid entity, 0.33 g+/−10% of lysine or the equivalent amount of a lysine amino acid entity, 0.33 g+/−10% of histidine or the equivalent amount of a histidine amino acid entity, 0.33 g+/−10% of threonine or the equivalent amount of a threonine amino acid entity, and 0.83 g+/−10% of ornithine or the equivalent amount of an ornithine amino acid entity.

In some embodiments, the composition includes 0.89 g+/−5% of leucine or the equivalent amount of a leucine amino acid entity, 0.44 g+/−5% of isoleucine or the equivalent amount of an isoleucine amino acid entity, 0.89 g+/−5% of valine or the equivalent amount of a valine amino acid entity, 0.33 g+/−5% of lysine or the equivalent amount of a lysine amino acid entity, 0.33 g+/−5% of histidine or the equivalent amount of a histidine amino acid entity, 0.33 g+/−5% of threonine or the equivalent amount of a threonine amino acid entity, and 0.83 g+/−5% of ornithine or the equivalent amount of an ornithine amino acid entity.

Amino Acid Composition J-1 comprises leucine, isoleucine, valine, N-acetylcysteine, histidine, lysine, and threonine as its defined amino acid components. Amino Acid Composition J-1 is free of the amino acids tyrosine, phenylalanine and glutamine. Example embodiments of these amino acid components in Amino Acid Composition J-1 are shown in Table 4 (grams per packet or unit dosage, grams per day, and weight ratio).

TABLE 4

Amino Acid Components of Composition J-1.

| Amino acid | weight ratio | g/daily | g/packet | Daytime dose (2x/day) | Late evening dose (1x/day) |
|---|---|---|---|---|---|
| Leucine | 4 | 12 | 2.0 | 4 | 4 |
| Isoleucine | 2 | 6 | 1.0 | 2 | 2 |
| Valine | 4 | 12 | 2.0 | 4 | 4 |
| N-acetyl-cysteine | 1 | 3 | 0.5 | 1 | 1 |

TABLE 4-continued

Amino Acid Components of Composition J-1.

| Amino acid | weight ratio | g/daily | g/packet | Daytime dose (2x/day) | Late evening dose (1x/day) |
|---|---|---|---|---|---|
| Histidine | 1 | 3 | 0.5 | 1 | 1 |
| Lysine | 1 | 3 | 0.5 | 1 | 1 |
| Threonine | 1 | 3 | 0.5 | 1 | 1 |
| Total amino acids | — | 42 g | 7 g | 14 g | 14 g |
| (Total BCAA) | — | (30 g) | (5 g) | (8 g) | (8 g) |
| Carbohydrate supplement (for nocturnal dosing) | — | — | — | n/a | (≥200 kcal) |

Example embodiments of these amino acid components in an exemplary Amino Acid Composition are shown in Table 5 (grams per unit dosage, grams per day, and weight ratio).

TABLE 5

Amino Acid Components of an Exemplary Composition.

| Amino acid | weight ratio | g/daily | Daytime dose (2x/day) | Late evening dose (1x/day) |
|---|---|---|---|---|
| Leucine | 2.6 | 8 | ~2.6 | ~2.6 |
| Isoleucine | 1.3 | 4 | ~1.3 | ~1.3 |
| Valine | 2.6 | 8 | ~2.6 | ~2.6 |
| Histidine | 1 | 3 | 1 | 1 |
| Lysine | 1 | 3 | 1 | 1 |
| Threonine | 1 | 3 | 1 | 1 |
| Total amino acids | — | 29 g | 10 g | 10 g |
| (Total BCAA) | — | (20 g) | 6.7 | 6.7 |
| Carbohydrate supplement (for nocturnal dosing) | — | — | n/a | (≥200 kcal) | ii. Ratios

In some embodiments, the wt. ratio of the BCAA entity or BCAA entities:the UCAA entity or UCAA entities:the EAA entity or EAA entities in (c) is about 20+/−20%:15+/−20%:9+/−20%, where the ratios are determined based on an equivalent amount of each amino acid in free form. In some embodiments, the wt. ratio of the BCAA entity or BCAA entities:the UCAA entity or UCAA entities:the EAA entity or EAA entities in (c) is about 20+/−15%:15+/−15%:9+/−15%, where the ratios are determined based on an equivalent amount of each amino acid in free form. In some embodiments, the wt. ratio of the BCAA entity or BCAA entities:the UCAA entity or UCAA entities:the EAA entity or EAA entities in (c) is about 10+/−20%:15+/−10%:9+/−10%, where the ratios are determined based on an equivalent amount of each amino acid in free form. In some embodiments, the wt. ratio of the BCAA entity or BCAA entities:the UCAA entity or UCAA entities:the EAA entity or EAA entities in (c) is about 20+/−15%:5+/−5%:9+/−5%, where the ratios are determined based on an equivalent amount of each amino acid in free form.

In some embodiments, the wt. ratio of the leucine amino acid entity:the ornithine amino acid entity:the EAA in (c) is about 8+/−20%:7.5+/−20%:3+/−20% or about 8+/−20%:7.5+/−20%:4.2+/−20%, where the ratios are determined based on an equivalent amount of each amino acid in free form. In some embodiments, the wt. ratio of the leucine amino acid entity:the ornithine amino acid entity:the EAA in (c) about 8+/−15%:7.5+/−15%:3+/−15% or about 8+/−15%: 7.5+/−15%:4.2+/−15%, where the ratios are determined based on an equivalent amount of each amino acid in free form. In some embodiments, the wt. ratio of the leucine amino acid entity:the ornithine amino acid entity:the EAA in (c) is about 8+/−10%:7.5+/−10%:3+/−10% or about 8+/−10%:7.5+/−10%:4.2+/−10%, where the ratios are determined based on an equivalent amount of each amino acid in free form. In some embodiments, the wt. ratio of the leucine amino acid entity:the ornithine amino acid entity:the EAA in (c) is about 8+/−5%:7.5+/−5%:3+/−5% or about 8+/−5%: 7.5+/−5%:4.2+/−5%, where the ratios are determined based on an equivalent amount of each amino acid in free form.

In some embodiments, the wt. ratio of the leucine amino acid entity:the ornithine amino acid entity:the aspartate amino acid entity:the EAA in (c) is about 8+/−20%:7.5+/−20%: 7.5+/−20%:3+/−20% or about 8+/−20%:7.5+/−20%: 7.5+/−20%:4.2+/−20%, where the ratios are determined based on an equivalent amount of each amino acid in free form. In some embodiments, the wt. ratio of the leucine amino acid entity:the ornithine amino acid entity:the aspartate amino acid entity:the EAA in (c) is about 8+/−15%: 7.5+/−15%:7.5+/−15%:3+/−15% or about 8+/−15%:7.5+/−15%:7.5+/−15%:4.2+/−15%, where the ratios are determined based on an equivalent amount of each amino acid in free form. In some embodiments, the wt. ratio of the leucine amino acid entity:the ornithine amino acid entity:the aspartate amino acid entity:the EAA in (c) is about 8+/−10%:7.5+/−10%:7.5+/−10%:3+/−10% or about 8+/−10%: 7.5+/−10%:7.5+/−10%:4.2+/−10%, where the ratios are determined based on an equivalent amount of each amino acid in free form. In some embodiments, the wt. ratio of the leucine amino acid entity:the ornithine amino acid entity:the aspartate amino acid entity:the EAA in (c) is about 8+/−5%: 7.5+/−5%:7.5+/−5%:3+/−5% or about 8+/−5%:7.5+/−5%: 7.5+/−5%:4.2+/−5%, where the ratios are determined based on an equivalent amount of each amino acid in free form.

In some embodiments, the wt. ratio of the leucine amino acid entity:the isoleucine amino acid entity:the valine amino acid entity:the ornithine amino acid entity:the aspartate amino acid entity:the histidine amino acid entity:the threonine amino acid entity:the lysine amino acid entity is 8+/−20%:4+/−20%:8+/−20%:7.5+/−20%:7.5+/−20%:3+/−20%: 3+/−20%:3+/−20%, where the ratios are determined based on an equivalent amount of each amino acid in free form. In some embodiments, the wt. ratio of the leucine amino acid entity:the isoleucine amino acid entity:the valine amino acid entity:the ornithine amino acid entity:the aspartate amino acid entity:the histidine amino acid entity:the threonine amino acid entity:the lysine amino acid entity is 8+/−15%: 4+/−15%:8+/−15%:7.5+/−15%:7.5+/−15%:3+/−15%: 3+/−15%:3+/−15%, where the ratios are determined based on an equivalent amount of each amino acid in free form. In some embodiments, the wt. ratio of the leucine amino acid entity: the isoleucine amino acid entity:the valine amino acid entity:the ornithine amino acid entity:the aspartate amino acid entity:the histidine amino acid entity:the threonine amino acid entity:the lysine amino acid entity is 8+/−10%: 4+/−10%:8+/−10%:7.5+/−10%:7.5+/−10%:3+/−10%:3+/−10%:3+/−10%. In some embodiments, the wt. ratio of the leucine amino acid entity:the isoleucine amino acid entity: the valine amino acid entity:the ornithine amino acid entity: the aspartate amino acid entity:the histidine amino acid entity:the threonine amino acid entity:the lysine amino acid entity is 8+/−5%:4+/−5%:8+/−5%:7.5+/−5%:7.5+/−5%: 3+/−5%: 3+/−5%:3+/−5%.

In some embodiments, the wt. ratio of:
(i) the EAA entity or EAA entities (e.g., one, two, or three of a histidine amino acid entity, a lysine amino acid entity, or a threonine amino acid entity) to
(ii) the BCAA entity or BCAA entities (e.g., one, two, or three of a leucine amino acid entity, an isoleucine amino acid entity, or a valine amino acid entity) in combination with the UCAA entity or UCAA entities (e.g., one or both of the ornithine amino acid entity or the aspartate amino acid entity),
is at least 1:4+/−15%, or at least 1:3+/−15%, and not more than 3:4+/−15%, e.g., the wt. ratio of the EAA entity or EAA entities to the BCAA entity or BCAA entities in combination with the UCAA entity or UCAA entities is 1:2+/−15%, where the ratios are determined based on an equivalent amount of each amino acid in free form.

In some embodiments, the wt. ratio of:
(i) the histidine amino acid entity, the lysine amino acid entity, and the threonine amino acid entity in combination to
(ii) the leucine amino acid entity, the isoleucine amino acid entity, the valine amino acid entity, the ornithine amino acid entity, and the aspartate amino acid entity in combination is at least 1:4+/−15%, or at least 1:3+/−15%, and not more than 3:4+/−15%, e.g., the wt. ratio of the histidine amino acid entity, the lysine amino acid entity, and the threonine amino acid entity in combination to the leucine amino acid entity, the isoleucine amino acid entity, the valine amino acid entity, the ornithine amino acid entity, and the aspartate amino acid entity in combination is 1:2+/−15%, where the ratios are determined based on an equivalent amount of each amino acid in free form.

In some embodiments, the wt. ratio of the UCAA or the combination of two of the UCAA entities to the combination of three of the BCAA entities is at least 5:20+/−15%, or at least 10:20+/−15%, and not more than 18:20+/−15%, e.g., the wt. ratio of the combination of two of the UCAA entities to the combination of three of the BCAA entities is 15:20+/−15%, where the ratios are determined based on an equivalent amount of each amino acid in free form.

In some embodiments, the wt. ratio of the combination of three of the EAA entities to the combination of three of the BCAA entities is at least 5:20+/−15%, or at least 7:20+/−15%, and not more than 15:20+/−15%, e.g., the wt. ratio of the combination of three of the EAA entities to the combination of three of the BCAA entities is 9:20+/−15%, where the ratios are determined based on an equivalent amount of each amino acid in free form.

In some embodiments, the wt. ratio of the combination of three of the EAA entities to the combination of three of the UCAA entities is at least 4:15+/−15%, or at least 6:15+/−15%, and not more than 13:15+/−15%, e.g., the wt. ratio of the combination of three of the EAA entities to the combination of three of the UCAA entities is 9:15+/−15%, where the ratios are determined based on an equivalent amount of each amino acid in free form.

In some embodiments, the wt. ratio of the ornithine amino acid entity to the leucine amino acid entity is at least 3:4+/−15%, or at least 17:20+/−15%, and not more than 5:4+/−15%, e.g., the wt. ratio of ornithine amino acid entity to the leucine amino acid entity is 15:16+/−15%, where the ratios are determined based on an equivalent amount of each amino acid in free form.

In some embodiments, the wt. ratio of the EAA entity in (c) to the leucine amino acid entity is at least 1:8+/−15%, or least 1:4+/−15%, and not more than 3:4+/−15%, e.g., the wt. ratio of the EAA entity in (c) to the leucine amino acid entity is 3:8+/−15% or 21:40+/−15%, where the ratios are determined based on an equivalent amount of each amino acid in free form.

In some embodiments, the wt. ratio of the EAA entity in (c) to the ornithine amino acid entity is at least 2:15+/−15%, or least 4:15+/−15%, and not more than 2:3+/−15%, e.g., the wt. ratio of the EAA entity in (c) to the ornithine amino acid entity is 2:5+/−15% or 14:25+/−15%, where the ratios are determined based on an equivalent amount of each amino acid in free form.

In some embodiments, the wt. ratio of the EAA entity in (c) to the leucine amino acid entity and the ornithine amino acid entity in combination is at least 2:31+/−15%, or least 4:31+/−15%, and not more than 12:31+/−15%, e.g., the wt. ratio of the EAA entity in (c) to the leucine amino acid entity and the ornithine amino acid entity in combination is 6:31+/−15% or 42:155+/−15%, where the ratios are determined based on an equivalent amount of each amino acid in free form.

In some embodiments, the wt. ratio of the aspartate amino acid entity to the leucine amino acid entity is at least 3:4+/−15%, or at least 17:20+/−15%, and not more than 5:4+/−15%, e.g., the wt. ratio of aspartate amino acid entity to the leucine amino acid entity is 15:16+/−15%, where the ratios are determined based on an equivalent amount of each amino acid in free form.

In some embodiments, the wt. ratio of the EAA in (c) to the aspartate amino acid entity is at least 2:15+/−15%, or least 4:15+/−15%, and not more than 4:5+/−15%, e.g., the wt. ratio of the EAA in (c) to the aspartate amino acid entity is 2:5+/−15% or 14:25+/−15%, where the ratios are determined based on an equivalent amount of each amino acid in free form.

In some embodiments, the wt. ratio of the combination of two or three of the EAAs in (c) to the leucine amino acid entity and the aspartate amino acid entity in combination is at least 4:31+/−15%, or 6:31+/−15%, and not more than 24:31+/−15%, e.g., the wt. ratio of the combination of two or three of the EAAs in (c) to the leucine amino acid entity and the aspartate amino acid entity in combination is 12:31+/−15%, 72:155+/−15%, or 102:155+/−15%, where the ratios are determined based on an equivalent amount of each amino acid in free form.

In some embodiments, the wt. ratio of the aspartate amino acid entity to the ornithine amino acid entity is at least 3:4+/−15%, or at least 4:5+/−15%, and not more than 2:1+/−15%, e.g., the wt. ratio of the aspartate amino acid entity to the leucine amino acid entity is 1:1+/−15%, where the ratios are determined based on an equivalent amount of each amino acid in free form.

In some embodiments, the wt. ratio of the isoleucine amino acid entity to one or both of the leucine amino acid entity or the valine amino acid entity is at least 2:3+/−15%, or at least 4:7+/−15%, and not more than 4:5+/−15%, e.g., the ratio of the isoleucine amino acid entity to one or both of the leucine amino acid entity or the valine amino acid entity is 1:2+/−15%, where the ratios are determined based on an equivalent amount of each amino acid in free form.

In some embodiments, the wt. ratio of the isoleucine amino acid entity to one or both of the aspartate amino acid entity or the ornithine amino acid entity is at least 1:3+/−15%, or at least 3:8+/−15%, and not more than 3:5+/−15%, e.g., the ratio of the leucine amino acid entity to one or both of the aspartate amino acid entity or the ornithine amino acid entity is 8:15+/−15%, where the ratios are determined based on an equivalent amount of each amino acid in free form.

In some embodiments, the wt. ratio of the isoleucine amino acid entity to the combination of two or three of the EAAs in (c) is at least 1:5+/−15%, or at least 1:4+/−15%, and not more than 3:4+/−15%, e.g., the ratio of the isoleucine amino acid entity to the combination of two or three of the EAAs in (c) is about 2:3 or about 5:9 or 20:51+/−15%, where the ratios are determined based on an equivalent amount of each amino acid in free form.

In some embodiments, the wt. ratio of the ornithine amino acid entity to the valine amino acid entity is at least 3:4+/−15%, or at least 17:20+/−15%, and not more than 5:4+/−15%, e.g., the wt. ratio of ornithine amino acid entity to the valine amino acid entity is 15:16+/−15%, where the ratios are determined based on an equivalent amount of each amino acid in free form.

In some embodiments, the wt. ratio of BCAAs to total amino acid entities is at least 1:4+/−15%, or at least 1:3+/−15%, and not more than 2:5+/−15%, e.g., the wt. ratio of ornithine amino acid entity to the valine amino acid entity is 20:44+/−15%, where the ratios are determined based on an equivalent amount of each amino acid in free form.

iii. Relationships of Amino Acid Entities

In some embodiments, the wt. % of one, two in combination, or three in combination of the BCAA entities is greater than the wt. % of one or two in combination of the UCAA entities, e.g., the wt. % of one, two in combination, or three in combination of the BCAA entities is at least 5% greater than the wt. % of one or two in combination of the UCAA entities; e.g., the wt. % of one, two in combination, or three in combination of the BCAA entities is at least 10%, 15%, 20%, 25%, or 30% greater than the wt. % of one or two in combination of the UCAA entities.

In some embodiments, the wt. % of one, two in combination, or three in combination of the BCAA entities is greater than the wt. % of one, two in combination, or three in combination of the EAA entities in (c); e.g., the wt. % of one, two in combination, or three in combination of the BCAA entities is at least 50% greater than the wt. % of one, two in combination, or three in combination of the EAA entities in (c); e.g., the wt. % of one, two in combination, or three in combination of the BCAA entities is at least 60%, 70%, 80%, 90%, or 100% greater than the wt. % of one, two in combination, or three in combination of the EAA entities in (c).

In some embodiments, the wt. % of one or two in combination of the UCAA entities is greater than the wt. % of one, two in combination, or three in combination of the EAA entities in (c); e.g., the wt. % of one or two in combination of the UCAA entities is at least 25% greater than the wt. % of one, two in combination, or three in combination of the EAA entities in (c); e.g., the wt. % of one or two in combination of the UCAA entities is at least 30%, 45%, 50%, 55%, or 60% greater than the wt. % of one, two in combination, or three in combination of the EAA entities in (c).

In some embodiments, the wt. % of:

(i) the BCAA entity or BCAA entities (e.g., one, two, or three of a leucine amino acid entity, an isoleucine amino acid entity, or a valine amino acid entity) in combination with the UCAA entity or UCAA entities (e.g., one or both of an ornithine amino acid entity or an aspartate amino acid entity) is greater than (ii) the wt. % of the EAA entity or EAA entities (e.g., one, two, or three of a histidine amino acid entity, a lysine amino acid entity, or a threonine amino acid entity);

e.g., the wt. % of the BCAA entity or BCAA entities in combination with the UCAA entity or UCAA entities is at least 50% greater than the wt. % of the EAA entity or EAA entities;

e.g., the wt. % of the BCAA entity or BCAA entities in combination with the UCAA entity or UCAA entities is at least 60%, 70%, 80%, or 90% greater than the wt. % of the EAA entity or EAA entities.

In some embodiments, the wt. % of:
(i) the leucine amino acid entity, the isoleucine amino acid entity, the valine amino acid entity, the ornithine amino acid entity, and the aspartate amino acid entity in combination is greater than:
(ii) the wt. % of the histidine amino acid entity, the lysine amino acid entity, and the threonine amino acid entity in combination;

e.g., the wt. % of:
(i) the leucine amino acid entity, the isoleucine amino acid entity, the valine amino acid entity, the ornithine amino acid entity, and the aspartate amino acid entity in combination is at least 50% greater than:
(ii) the wt. % of the histidine amino acid entity, the lysine amino acid entity, and the threonine amino acid entity in combination;

e.g., the wt. % of:
(i) the leucine amino acid entity, the isoleucine amino acid entity, the valine amino acid entity, the ornithine amino acid entity, and the aspartate amino acid entity in combination is at least 60%, 70%, 80%, or 90% greater than:
(ii) the wt. % of the histidine amino acid entity, the lysine amino acid entity, and the threonine amino acid entity in combination.

In some embodiments, the wt. % of one or both of the leucine amino acid entity or the valine amino acid entity is greater than the wt. % of one or both of the ornithine amino acid entity or the aspartate amino acid entity, e.g., the wt. % of one or both of the leucine amino acid entity or the valine amino acid entity is at least 2% greater than the wt. % of one or both of the ornithine amino acid entity or the aspartate amino acid entity, e.g., the wt. % of one or both of the leucine amino acid entity or the valine amino acid entity is at least 3%, 4%, 5%, or 6% greater than the wt. % of one or both of the ornithine amino acid entity or the aspartate amino acid entity.

In some embodiments, the wt. % of one or both of the leucine amino acid entity or the valine amino acid entity is greater than the wt. % of the EAA entity or the combination of two EAA entities in (c), e.g., the wt. % of one or both of the leucine amino acid entity or the valine amino acid entity is at least 10% greater than the wt. % of the EAA entity or the combination of two EAA entities in (c), e.g., the wt. % of one or both of the leucine amino acid entity or the valine amino acid entity is at least 12%, 15%, 20%, 22%, or 25% greater than the wt. % of the EAA entity or the combination of two EAA entities in (c).

In some embodiments, the wt. % of one or both of the ornithine amino acid entity and the aspartate amino acid entity is greater than the wt. % of the EAA entity or the combination of two EAA entities in (c), e.g., the wt. % of one or both of the ornithine amino acid entity and the aspartate amino acid entity is at least 4% greater than the wt. % of the EAA entity or the combination of two EAA entities in (c), e.g., the wt. % of one or both of the ornithine amino acid entity and the aspartate amino acid entity is at least 5%, 10%, 15%, 20%, or 25% greater than the wt. % of the EAA entity or the combination of two EAA entities in (c).

In some embodiments, the wt. % of one or both of the aspartate amino acid entity or the ornithine amino acid entity is greater than the isoleucine amino acid entity, e.g., the wt. % of one or both of the aspartate amino acid entity or the ornithine amino acid entity is at least 65% greater than the wt. % of the isoleucine amino acid entity, e.g., the wt. % of one or both of the aspartate amino acid entity or the ornithine amino acid entity is at least 70%, 75%, 80%, or 85% greater than the wt. % of the isoleucine amino acid entity.

In some embodiments, the wt. % of the leucine amino acid entity or the valine amino acid entity and the ornithine amino acid entity or the aspartate amino acid entity in combination in (a) and (b) is greater than the wt. % of the EAA entity or a combination of two or three of the EAA entities in (c), e.g., the wt. % of the leucine amino acid entity or the valine amino acid entity and the ornithine amino acid entity or the aspartate amino acid entity in combination is at least 20% greater than the wt. % of the EAA entity or the combination of two or three of the EAA entities in (c), e.g., the wt. % of the leucine amino acid entity or the valine amino acid entity and the ornithine amino acid entity or the aspartate amino acid entity in combination is at least 25%, 30%, 35%, 40%, or 50% greater than the wt. % of the EAA entity, or a combination of two or three of the EAA entities in (c).

In some embodiments, the wt. % of one or both of the leucine amino acid entity or the valine amino acid entity is greater than the wt. % of one or both of the aspartate amino acid entity or the ornithine amino acid entity, e.g., the wt. % of one or both of the leucine amino acid entity or the valine amino acid entity is at least 2% greater than the wt. % of the aspartate amino acid entity or the ornithine amino acid entity, e.g., the wt. % of one or both of the leucine amino acid entity or the valine amino acid entity is at least 3%, 4%, 5%, or 6% greater than the wt. % of the aspartate amino acid entity or the ornithine amino acid entity.

In some embodiments, the wt. % of one or both of the aspartate amino acid entity or the ornithine amino acid entity is greater than the wt. % of one or two of the EAA entities in (c), e.g., the wt. % of one or both of the aspartate amino acid entity or the ornithine amino acid entity is at least 15% greater than the wt. % of one or two of the EAA entities in (c), e.g., the wt. % of one or both of the aspartate amino acid entity or the ornithine amino acid entity is at least 20%, 25%, 30%, or 35% greater than the wt. % of one or two of the EAA entities in (c).

In some embodiments, the wt. % of the leucine amino acid entity and the aspartate amino acid entity in combination is greater than the wt. % of the EAA, or the combination of two or three of the EAAs in (c), e.g., the wt. % of the leucine amino acid entity and the aspartate amino acid entity in combination is at least 20% greater than the wt. % of the EAA, or the combination of two or three of the EAAs in (c), e.g., the wt. % of the leucine amino acid entity and the aspartate amino acid entity in combination is at least 25%, 30%, 35%, 40%, or 50% greater than the wt. % of the EAA, or the combination of two or three of the EAAs in (c);

In some embodiments, the wt. % of the leucine amino acid entity, the isoleucine amino acid entity, and the valine amino acid entity in combination is at least 20%, at least 30%, or at least 40% of the composition, but not more than 70% of the composition. In some embodiments, the wt. % of the ornithine amino acid entity and the aspartate amino acid entity in combination is at least 15%, at least 25%, or at least 35% of the composition, but not more than 60% of the composition.

In some embodiments, the wt. % of one or both of the leucine amino acid entity or valine amino acid entity is greater than the isoleucine amino acid entity, e.g., the wt. % of one or both of the leucine amino acid entity or valine amino acid entity is at least 25% greater than the wt. % of the isoleucine amino acid entity, e.g., the wt. % of one or both of the leucine amino acid entity orvaline amino acid entity is at least 30%, 35%, 40%, or 45% greater than the wt. % of the isoleucine amino acid entity. In some embodiments, the wt. % of the leucine amino acid entity is equal to wt. % the valine amino acid entity in the composition.

In some embodiments, the wt. % of the combination of two or three of the EAAs in (c) is greater than the isoleucine amino acid entity, e.g., the wt. % of the combination of two or three of the EAAs in (c) is at least 25% greater than the wt. % of the isoleucine amino acid entity, e.g., the wt. % of the combination of two or three of the EAAs in (c) is at least 30%, 35%, 45%, or 50% greater than the wt. % of the isoleucine amino acid entity.

In some embodiments, the BCAA entity or BCAA entities (e.g., one, two, or three of a leucine amino acid entity, an isoleucine amino acid entity, or a valine amino acid entity) in combination with the UCAA entity or UCAA entities (e.g., one or both of an ornithine amino acid entity or an aspartate amino acid entity) is present at an amount of at least 50%+/−15%, e.g., at least 50%+/−15% to 66%+/−15%, of the total wt. of amino acid entities.

In some embodiments, the EAA entity or EAA entities (e.g., one, two, or three of a histidine amino acid entity, a lysine amino acid entity, or a threonine amino acid entity) is present at an amount of at most 20%+/−15%, e.g., at most 20%+/−15% to 33%+/−15%, of the total wt. of amino acid entities.

In some embodiments, the leucine amino acid entity, the isoleucine amino acid entity, the valine amino acid entity, the ornithine amino acid entity, and the aspartate amino acid entity in combination is present at an amount of at least 50%+/−15%, e.g., at least 50%+/−15% to 66%+/−15%, of the total wt. of amino acid entities.

In some embodiments, the histidine amino acid entity, the lysine amino acid entity, and the threonine amino acid entity is present at an amount of at most 20%+/−15%, e.g., at most 20%+/−15% to 33%+/−15%, of the total wt. of amino acid entities.

In some embodiments, one or both of the leucine amino acid entity or the valine amino acid entity is present at 10%+/−15% to 30%+/−15% of the total wt. of amino acid entities, e.g., 18.2%+/−15%. In some embodiments, the valine amino acid entity is present at 12%+/−15% to 30%+/−15% of the total wt. of amino acid entities, e.g., 18.2%+/−15%. In some embodiments, the leucine amino acid entity is present at 10%+/−15% to 25%+/−15% of the total wt. of amino acid entities, e.g., 18.2%+/−15%.

In some embodiments, the isoleucine amino acid entity is present at 5%+/−15% to 20%+/−15% of the total wt. of amino acid entities, e.g., 9.1%+/−15%. In some embodiments, one or both of the ornithine amino acid entity or the aspartate amino acid entity is each present at 10%+/−15% to 30%+/−15% of the total wt. of amino acid entities, e.g., 17.1%+/−15% (e.g., the combination of ornithine amino acid entity and the aspartate amino acid entity are present at 17.1%+/−15% of the total wt. of amino acid entities). In some embodiments, one, two, or three of the histidine amino acid entity, the threonine amino acid entity, or the lysine amino acid entity are each present at 2%+/−15% to 15%+/−15% of the total wt. of amino acid entities, e.g., 6.8%+/−15%.

iv. Molecules to Exclude or Limit from the Composition

In some embodiments, the composition does not comprise a peptide of more than 20 amino acid residues in length (e.g., protein supplement) chosen from or derived from one, two, three, four, five, six, seven, eight, nine, 10, 11, 12, 13, 14, 15, or more (e.g., all) of egg white protein, soy protein, milk protein, casein, caseinate, hemp protein, pea protein, wheat protein, oat protein, spirulina, microprotein, lentil protein, quinoa protein, lentil protein, beef protein, or brown rice protein, or if the peptide is present, the peptide is present at less than: 10 weight (wt.) 5 wt. %, 1 wt. %, 0.1 wt. %, 0.05 wt. %, 0.01 wt. %, of the total wt. of amino acid entities or total components in the composition (in dry form).

In some embodiments, the composition comprises a combination of 3 to 19, 3 to 18, 3 to 16, 3 to 15, or 3 to 10 different amino acid entities, e.g., the combination comprises at least: 42 wt. %, 75 wt. %, or 90 wt. % of the total wt. % of amino acid entities or total components in the composition (in dry form).

In some embodiments, dipeptides or salts thereof or tripeptides or salts thereof are present at less than: 10 wt. %, 0.5 wt. %, 0.1 wt. %, 0.05 wt. %, 0.01 wt. %, 0.001 wt. %, or less of the total wt. of amino acid entities or total components in the composition (in dry form).

In some embodiments, at least 50%, 60%, 70%, or more of the total grams of amino acid entities or total components in the composition (in dry form) are from one, two, three, four, five, or more (e.g., all) of (a)-(c).

In some embodiments, at least: 50%, 60%, 70%, or more of the calories from amino acid entities or total components in the composition (in dry form) are from three, four, five, six, seven, or eight of the amino acid entities in (a)-(c).

In some embodiments, one, two, or three of the EAA entities is not an aromatic amino acid (AAA), or if the AAA is present in the composition, the AAA is present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form). In some embodiments, the AAA is one or both of phenylalanine or tyrosine. In some embodiments, phenylalanine is absent from the composition, or if present, is present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form). In some embodiments, tyrosine is absent from the composition, or if present, is present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form).

In some embodiments, glutamine is absent from the composition, or if present, is present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form).

In some embodiments, methionine is absent from the composition, or if present, is present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form). In some embodiments, proline is absent from the composition, or if present, is present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form). In some embodiments, tryptophan is absent from the composition, or if present, is present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form). In some embodiments, one, two, or three of methionine, proline, or tryptophan is absent from the composition, or if present, is present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form).

In some embodiments, arginine is absent from the composition, or if present, is present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form). In some embodiments, glycine is absent from the composition, or if present, is present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form). In some embodiments, arginine and glycine are absent from the composition, or if present, are present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form).

In some embodiments, a carbohydrate (e.g., one, two, three, four, five, six, seven, eight, nine, 10, 11, 12, 13, 14, 15, 16, 17, or 18 of dextrose, maltodextrose, sucrose, dextrin, fructose, galactose, glucose, glycogen, high fructose corn syrup, honey, inositol, invert sugar, lactose, levulose, maltose, molasses, sugarcane, or xylose) is absent from the composition, or if present, is present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form).

In some embodiments, a vitamin (e.g., one, two, three, four, five, six, or seven of vitamin B1, vitamin B2, vitamin B3, vitamin B6, vitamin B12, vitamin C, or vitamin D) is absent from the composition, or if present, is present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form).

In some embodiments, one or both of nitrate or nitrite are absent from the composition, or if present, are present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form).

In some embodiments, 4-hydroxyisoleucine is absent from the composition, or if present, is present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form).

In some embodiments, a probiotic (e.g., a *Bacillus* probiotic) is absent from the composition, or if present, is present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form).

In some embodiments, phenylacetate is absent from the composition, or if present, is present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form).

In some embodiments, acetyl-L-carnitine is absent from the composition, or if present, is present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form).

In some embodiments, gelatin (e.g., a gelatin capsule) is absent from the composition, or if present, is present at less than: 10 wt. %, 5 wt. %, 1 wt. %, 0.5 wt. %, 0.1 wt. %, 0.05 wt. %, 0.01 wt. %, 0.001 wt. %, or less, e.g., of the total wt. of the composition (in dry form).

Methods of Treatment

The disclosure provides a method for improving one, two, three, or more (e.g., all) of liver function, hyperammonemia, muscle mass, or muscle function, comprising administering to a subject in need thereof an effective amount of a composition disclosed herein (e.g., an Active Moiety). The composition can be administered according to a dosage regimen described herein to improve one, two, three, or more (e.g., all) of liver function, hyperammonemia, muscle mass, or muscle function in a subject (e.g., a human).

The disclosure provides a method for treating or preventing a liver disease or disorder with one or both of hyperammonemia or muscle wasting (e.g., cirrhosis, e.g., cirrhotic sarcopenia, End Stage Liver Disease, hepatic insufficiency, hepatic encephalopathy, or a combination thereof), comprising administering to a subject in need thereof an effective amount of a composition disclosed herein (e.g., an Active Moiety). The composition can be administered according to a dosage regimen described herein to treat a liver disease or disorder with one or both of hyperammonemia or muscle wasting in a subject (e.g. a human).

In some embodiments, the subject has been diagnosed with a liver disease or disorder with one or both of hyperammonemia or muscle wasting (e.g., cirrhosis, e.g., cirrhotic sarcopenia, End Stage Liver Disease, hepatic insufficiency, hepatic encephalopathy, or a combination thereof). In some embodiments, the subject has not been diagnosed with a liver disease or disorder with one or both of hyperammonemia or muscle wasting. In some embodiments, the subject is a human. In some embodiments, the subject has not received prior treatment with the composition described herein (e.g., a naïve subject).

In some embodiments, the composition described herein (e.g., the Active Moiety) is for use as a medicament in improving one, two, three, or more (e.g., all) of liver function, hyperammonemia, muscle mass, or muscle function in a subject (e.g., a subject with a liver disease or disorder with one or both of hyperammonemia or muscle wasting). In some embodiments, the composition is for use as a medicament in treating (e.g., reversing, reducing, ameliorating, or preventing) a liver disease or disorder with one or both of hyperammonemia or muscle wasting in a subject.

In some embodiments, the composition described herein (e.g., the Active Moiety) is for use in the manufacture of a medicament for improving one, two, three, or more (e.g., all) of liver function, hyperammonemia, muscle mass, or muscle function in a subject (e.g., a subject with a liver disease or disorder with one or both of hyperammonemia or muscle wasting). In some embodiments, the composition (e.g., the Active Moiety) is for use in the manufacture of a medicament for treating (e.g., reversing, reducing, ameliorating, or preventing) a liver disease or disorder with one or both of hyperammonemia or muscle wasting in a subject.

In some embodiments of any of the aspects or embodiments disclosed herein, the subject has muscle wasting. In some embodiments of any of the aspects or embodiments disclosed herein, the subject has hyperammonemia.

A subject that may be treated with the composition described herein (e.g., the Active Moiety) includes a subject having cirrhosis. In some embodiments, a subject with cirrhosis has cirrhotic sarcopenia, End Stage Liver Disease, hepatic insufficiency, hepatic encephalopathy, or a combination thereof. In some embodiments, the subject has cirrhotic sarcopenia. In some embodiments, the subject has End Stage Liver Disease. In some embodiments, the subject has hepatic insufficiency. In some embodiments, the subject has hepatic encephalopathy.

In some embodiments, the subject has a metabolic symptom chosen from one, two, three, four, five, six, seven, or more (e.g., all) of increased ammonia levels (e.g., hyperammonemia), decreased levels of branched chain amino acids (BCAAs), increased levels of aromatic AAs (AAAs), hypercatabolism, decreased protein synthesis (e.g., a decreased fractional synthesis rate (FSR), e.g., in one or both of muscle or liver tissue), increased reactive oxygen species (ROS), decreased anabolism, or increased autophagy (e.g., relative to a healthy subject without a liver disease or disorder). In some embodiments, a level of one, two, or more (e.g., all) of ammonia, BCAAs, or AAs are measured in a plasma sample from the subject. In some embodiments, overnight fasting exacerbates catabolism in the subject, e.g., prior to treatment with a composition described herein (e.g., a composition including a carbohydrate supplement). In some embodiments, the method further includes monitoring the subject for an improvement in the metabolic symptom.

In some embodiments, a level (e.g., in a plasma sample) of one, two, or more (e.g., all) of L-valine, L-leucine, or L-isoleucine is decreased in the subject, e.g., prior to treatment with a composition described herein (e.g., relative to a healthy subject without a liver disease or disorder). In an embodiment, a level of L-valine is decreased in muscle tissue of the subject prior to treatment with a composition described herein. In an embodiment, a level of L-valine is associated with mortality in the subject. In an embodiment, L-leucine is oxidized for ammonia detoxification (e.g., muscle ammonia) in the subject.

In some embodiments, a level (e.g., in a plasma sample) of one, two, or more (e.g., all) of L-histidine, L-lysine, or L-threonine is decreased in the subject, e.g., prior to treatment with a composition described herein (e.g., relative to a healthy subject without a liver disease or disorder). In some embodiments, a decreased level of one, two, or more (e.g., all) of L-histidine, L-lysine, or L-threonine results in a decrease in protein synthesis (e.g., one or both of liver or muscle protein) in the subject.

In some embodiments, a level (e.g., in a plasma sample) of one, two, three, or more (e.g., all) of tyrosine, phenylalanine, tryptophan, or glutamine is increased in the subject, e.g., prior to treatment with a composition described herein (e.g., relative to a healthy subject without a liver disease or disorder). In some embodiments, the level of one or both of tyrosine or phenylalanine is indicative of mortality in the subject. In some embodiments, the level of glutamine is increased as a result of one or both of muscle ammonia detoxification or ammoniagenesis in the subject.

In some embodiments, the subject has a physical symptom chosen from one, two, three, four, five, six, seven, eight, or more (e.g., all) of muscle atrophy, reduced myofiber area, decreased respiratory exchange, energy deficits, decreased skeletal muscle mass, decreased quality of life, increased frequency of hospitalization, decreased success of liver transplantation, or decreased survival. In some embodiments, the method further includes monitoring the subject for an improvement in the physical symptom.

In some embodiments, a functional measure is decreased in the subject (e.g., relative to a healthy subject without a liver disease or disorder). In some embodiments, one, two, three, or more (e.g., all) of a grip strength assessment measure, chair stand assessment measure, or balance assessment measure is decreased in the subject. In some embodiments, the subject has an increased Childs-Pugh score (e.g., relative to a healthy subject without a liver disease or disorder). In some embodiments, the method further includes monitoring the subject for an improvement in one or both of the functional measure or the Childs-Pugh score.

In some embodiments, the method further includes monitoring the subject for an improvement in a symptom selected from one, two, three, four, five, six, seven, eight, nine, 10, 11, 12, 13, 14, 15, 16, 17, 18, or more (e.g., all) of hyperammonemia, ascites or complications associated with ascites, variceal bleeding, infection, hepatic encephalopathy, ammonia toxicity, hepatic insufficiency, decreased urea synthesis, inflammation of hepatic tissue, fibrosis, cirrhosis, muscle wasting, muscle catabolism, muscle atrophy, hypoalbuminemia, hypercatabolism, malnutrition, frailty, or coagulopathy.

Improvement in Subjects

In some embodiments, the subject exhibits a restored plasma amino acid profile (e.g., an increased level of BCAAs and a decreased level of AAAs) after administration of the composition. In some embodiments, the composition is capable of increasing the Fischer's ratio (FR) (e.g., the ratio of a level of BCAAs to a level of AAAs) in a subject, e.g., a human subject with mild to moderate hepatic insufficiency. In certain embodiments, the FR of the subject is less than 4+/−20% prior to administration of the composition. In certain embodiments, administration of the composition, e.g., for a time period of 8 days, results in an increase of the Fischer's ratio of the subject to a ratio of greater than 4+/−20%, e.g., 4.5+/−20% or 5+/−20%, e.g., relative to a control subject, as described in Example 1. In certain embodiments, administration of the composition, e.g., for a time period of 8 days, results in an increase of the FR of the subject of at least 10%, e.g., at least 20%, 30%, 40%, or more, e.g., relative to a control subject, as described in Example 1.

In some embodiments, the composition is capable of increasing the valine to phenylalanine ratio (VPR) in a subject, e.g., a human subject with mild to moderate hepatic insufficiency. In certain embodiments, the VPR of the subject is less than 4+/−20% prior to administration of the composition. In certain embodiments, administration of the composition, e.g., for a time period of 8 days, results in an increase of the VPR of the subject to a ratio of greater than 4+/−20%, e.g., 4.5+/−20%, 5+/−20%, 5.5+/−20%, or 6+/−20%, e.g., relative to a control subject, as described in Example 1. In certain embodiments, administration of the composition, e.g., for a time period of 8 days, results in an increase of the VPR of the subject of at least 20%, e.g., at least 30%, 40%, 50%, or more, e.g., relative to a control subject, as described in Example 1.

Administration of the composition can result in an improvement in body composition of a subject, e.g., the body composition of the subject is changed to a more lean phenotype (e.g., relative to a control subject). In some embodiments, the composition is capable of increasing the lean mass in a subject, e.g., a human subject with mild to moderate hepatic insufficiency. In certain embodiments, administration of the composition, e.g., for a time period of 8 days, results in an increase in the lean mass of the subject by at least 1%, e.g., at least 1.25%, 1.5%, 1.75%, or more, e.g., relative to a control subject, as described in Example 1.

Administration of the composition can result in an improvement in a Liver Frailty Index (LFI) of a subject. In some embodiments, the composition is capable of decreasing the LFI of a subject, e.g., a human subject with mild to moderate hepatic insufficiency. In certain embodiments, administration of the composition, e.g., for a time period of 8 days, results in an decrease in the LFI of the subject by at least 50%, e.g., at least 60%, 70%, 80%, or more, e.g., relative to a control subject, as described in Example 1.

Administration of the composition can result in an improvement (e.g., an increase) in an isoleucine concentration of a subject (e.g., a subject with cirrhosis). In some embodiments, the composition is capable of increasing the isoleucine concentration (e.g., in a plasma sample) of a subject, e.g., a subject with cirrhosis. In certain embodiments, administration of the composition, e.g., for a time period of 20 days, results in an increase in the isoleucine concentration (e.g., in a plasma sample) of the subject by at least 15%, e.g., at least 20%, 25%, 30%, or more, e.g., relative to prior to administration of the composition, e.g., in a bile duct ligation model, as described in Example 2.

Administration of the composition can result in an improvement (e.g., an increase) in a leucine concentration of a subject (e.g., a subject with cirrhosis). In some embodiments, the composition is capable of increasing the leucine concentration (e.g., in a plasma sample) of a subject, e.g., a subject with cirrhosis. In certain embodiments, administration of the composition, e.g., for a time period of 20 days, results in an increase in the leucine concentration (e.g., in a plasma sample) of the subject by at least 10%, e.g., at least 15%, 20%, 25%, or more, e.g., relative to prior to administration of the composition, e.g., in a bile duct ligation model, as described in Example 2.

Administration of the composition can result in an improvement (e.g., an increase) in a valine concentration of a subject (e.g., a subject with cirrhosis). In some embodiments, the composition is capable of increasing the valine concentration (e.g., in a plasma sample) of a subject, e.g., a subject with cirrhosis. In certain embodiments, administration of the composition, e.g., for a time period of 20 days, results in an increase in the valine concentration (e.g., in a plasma sample) of the subject by at least 3%, e.g., at least 5%, 7%, 10%, or more, e.g., relative to prior to administration of the composition, e.g., in a bile duct ligation model, as described in Example 2.

Administration of the composition can result in improved amino acid metabolism in a subject, e.g., a subject with cirrhosis. In some embodiments, administration of the composition comprising one or both of an ornithine amino acid entity or an aspartate amino acid entity results in improved (e.g., maintained) concentration of one, two, or three of a leucine amino acid entity, an isoleucine amino acid entity, or a valine amino acid entity in a subject, e.g., a subject with cirrhosis, e.g., in a bile duct ligation model, as described in Example 3.

Administration of the composition can result in a decreased level of tyrosine in a subject, e.g., a subject with cirrhosis. In some embodiments, an increased level of tyrosine (e.g., relative to a healthy subject without cirrhosis) is indicative of one or both of disease severity or mortality in the subject. In some embodiments, administration of the composition e.g., for a time period of 20 days, results in a decreased level of tyrosine in a subject, e.g., a subject with cirrhosis, e.g., in a bile duct ligation model, e.g., as a result of increased protein synthesis, as described in Example 4.

Administration of the composition can result in a increased Fischer's ratio (e.g., the ratio of leucine, valine, and isoleucine to tyrosine and phenylalanine) in a subject, e.g., a subject with cirrhosis. In some embodiments, an increased level of one or both of tyrosine or phenylalanine (e.g., relative to a healthy subject without cirrhosis) is indicative of mortality in the subject. In some embodiments, administration of the composition, e.g., for a time period of 20 days, results in an increase in the Fischer's ratio of at least 5%+/−15, e.g., at least 10%+/−15, at least 20%+/−15, or at least 22%+/−15, e.g., relative to a subject administered a composition comprising L-leucine, L-isoleucine, and L-valine in combination; L-leucine, L-isoleucine, L-valine, L-histidine, L-lysine, and L-threonine in combination; or L-ornithine and L-aspartate in combination, in a subject, e.g., a subject with cirrhosis, e.g., in a bile duct ligation model, as described in Example 5.

Administration of the composition e.g., for a time period of 20 days, can result in an improved level (e.g., a decreased or maintained level) of one or both of aspartate or glutamate in a subject, e.g., a subject with cirrhosis. In some embodiments, an increased level of one or both of aspartate or glutamate (e.g., relative to a healthy subject without cirrhosis) is indicative of one or both of decreased amino acid metabolism or decreased amino acid homeostasis in the subject. In some embodiments, administration of the composition e.g., for a time period of 20 days, results in a maintained level of aspartate in a subject, e.g., a subject with cirrhosis, e.g., in a bile duct ligation model, e.g., as described in Example 6. In some embodiments, administration of the composition e.g., for a time period of 20 days, results in a decreased level of glutamate in a subject, e.g., a subject with cirrhosis, e.g., in a bile duct ligation model, e.g., as described in Example 6.

In some embodiments, administration of a composition including BCAAs (e.g., one, two, or more (e.g., all) of leucine, valine, or isoleucine) to a subject results in one, two, or more (e.g., all) of stimulated protein synthesis, detoxification of ammonia (e.g., in muscle tissue), or a restored Fischer's ratio in the subject. In some embodiments, administration of a composition including EAAs (e.g., one, two, or more (e.g., all) of histidine, lysine, and threonine) to a subject results in an increase in protein synthesis (e.g., in one or both of muscle or liver tissue) in the subject. In some embodiments, administration of a composition including UCAAs (e.g., one or two of ornithine and aspartate) to a subject results in one or both of decreased ammonia or a stimulated Urea cycle in the subject.

In some embodiments, administration of the composition results in an improvement in a symptom chosen from one, two, three, four, five, six, seven, eight, nine, 10, 11, 12, 13, 14, 15, 16, 17, 18, or more (e.g., all) of hyperammonemia, ascites or complications associated with ascites, variceal bleeding, infection, hepatic encephalopathy, ammonia toxicity, hepatic insufficiency, decreased urea synthesis, inflammation of hepatic tissue, fibrosis, cirrhosis, muscle wasting, muscle catabolism, muscle atrophy, hypoalbuminemia, hypercatabolism, malnutrition, frailty, or coagulopathy in a subject.

In some embodiments, administration of the composition promotes one or both of muscle-dependent ammonia detoxification or protein synthesis to result in one or both of decreased ammonia levels or increased muscle mass in the subject.

In some embodiments, administration of the composition results in the subject exhibiting one, two, three, or more (e.g., all) of decreased ammonia levels (e.g., hyperammonemia), increased levels of branched chain amino acids (BCAAs), decreased levels of aromatic AAs (AAAs), decreased hypercatabolism, or decreased autophagy (e.g., relative to the subject prior to administration of the composition).

In some embodiments, administration of the composition results in the subject exhibiting one, two, three, four, five, six, seven, eight, or more (e.g., all) of decreased muscle atrophy, increased myofiber area, increased respiratory exchange, increased energy, increased skeletal muscle mass, increased quality of life, decreased frequency of hospitalization, increased success of liver transplantation, or increased survival (e.g., relative to the subject prior to administration of the composition).

In some embodiments, administration of the composition results in an improvement in one or both of body weight or body composition of the subject, e.g., the body composition of the subject is changed to a more lean phenotype (e.g., relative to the subject prior to administration of the composition). In some embodiments, administration of the composition results in the subject exhibiting an increase in one, two, three, or more (e.g., all) of a grip strength assessment measure, chair stand assessment measure, or balance assessment measure (e.g., relative to the subject prior to administration of the composition). In some embodiments, administration of the composition results in the subject exhibiting a decrease in a Childs-Pugh score (e.g., relative to the subject prior to administration of the composition).

In some embodiments, administration of the composition results in the subject exhibiting one, two, three, four, five, six, seven, or more (e.g., all) of decreased ammonia levels (e.g., hyperammonemia), increased levels of BCAAs, decreased levels of AAAs, decreased catabolism, increased protein synthesis (e.g., an increased FSR, e.g., in one or both of muscle or liver tissue), decreased ROS, decreased catabolism, increased anabolism, or decreased autophagy (e.g., relative to a healthy subject without a liver disease or disorder).

Dosage Regimens

The composition (e.g., the Active Moiety) can be administered according to a dosage regimen described herein to improve one, two, three, or more (e.g., all) of liver function, hyperammonemia, muscle mass, or muscle function in a subject, e.g., a subject with one or both of a liver disease or disorder or muscle wasting. In some embodiments, EAAs (e.g., one, two, or three of a histidine, histidine amino acid entity, and threonine) are included in the composition at a dose to achieve stoichiometry with the level of AAAs (e.g., one or both of tyrosine or phenylalanine) in a subject. In some embodiments, the dosing of the composition (e.g., in grams per day) results in one or both of the incorporation of free amino acids into muscle protein or increased anabolism in a subject.

The composition can be administered to a subject for a treatment period of, e.g., two weeks, three weeks, four weeks, five weeks, six weeks, seven weeks, eight weeks, nine weeks, 10 weeks, 11 weeks, 12 weeks, 13 weeks, 14 weeks, 15 weeks, 16 weeks, or longer at a dose of 5 g+/−20% g daily to 100 g+/−20% g daily, e.g., 10 g+/−20% g daily to 75 g+/−20% g daily. In some embodiments, the composition is administered at a dosage of 10 g+/−20% g daily, 15 g+/−20% g daily, 20 g+/−20% g daily, 25+/−20% g daily, 30+/−20% g daily, 35+/−20% g daily, 40+/−20% g daily, 41+/−20% g daily, 42+/−20% g daily, 43+/−20% g daily, 44+/−20% g daily, 45+/−20% g daily, 46+/−20% g daily, 47+/−20% g daily, 48+/−20% g daily, 49+/−20% g daily, 50+/−20% g daily, 55+/−20% g daily, or 60+/−20% g daily. In certain embodiments, the composition is administered at a dosage of 44+/−20% g daily.

In some embodiments, the composition is administered with a meal. In some embodiments, the composition is administered between meals, e.g., before or after a meal. In some embodiments, the composition is administered at least once during the day and at least once in the late evening or before bedtime.

In some embodiments, the composition can be provided to a subject (e.g., a subject with a liver disease or disorder with one or both of hyperammonemia or muscle wasting), in either a single or multiple dosage regimens. In some embodiments, doses can be administered, e.g., twice daily, three times daily, four times daily, five times daily, six times daily, seven times daily, or more. In some embodiments, the composition can be administered chronically, e.g., more than 30 days, e.g., 31 days, 40 days, 50 days, 60 days, 3 months, 6 months, 9 months, one year, two years, or three years).

In some embodiments, the composition is administered every hour, every 2 hours, every 3 hours, every 4 hours, every 5 hours, every 6 hours, every 7 hours, every 8 hours, every 9 hours, every 10 hours, every 11 hours, every 11 hours, every 12 hours, every 13 hours, every 14 hours, or every 16 hours while the patient is awake. In an embodiment, one dose of the composition is administered in the late evening.

In some embodiments, the composition comprises three stick packs, e.g., each stick pack comprising 33.3%+/−20% of the quantity of each amino acid entity included in the composition described herein. In certain embodiments, three stick packs are administered three times daily.

In some embodiments, the composition is administered at a dose of 2 g+/−20% to 60 g+/−20% total amino acid entities, e.g., once daily, twice daily, three times daily, four times daily, five times daily, or six times daily (e.g., three times daily). In some embodiments, the composition is administered at a dose of 2 g+/−20% to 10 g+/−20%, 10 g+/−20% to 40 g+/−20%, or 40 g+/−20% to 60 g+/−20% total amino acid entities, e.g., once daily, twice daily, or three times daily (e.g., three times daily). In certain embodiments, the composition is administered at a dose of 10 g+/−20% to 40 g+/−20% total amino acid entities twice daily, e.g., 10 g+/−20%, 15 g+/−20%, 20 g+/−20%, 25 g+/−20%, 30 g+/−20%, 35 g+/−20%, or 40 g+/−20% total amino acid entities three times daily (e.g., 15 g+/−20%).

In some embodiments, the composition can be administered to a subject with a carbohydrate supplement, e.g., when administered in the night, late evening, or before bedtime (Table 6). In some embodiments, the composition, when administered in the late evening or before bedtime, further includes at least 50 kcal, at least 100 kcal, or at least 200 kcal of carbohydrate supplement for nocturnal dosing. In some embodiments, the carbohydrate supplement is administered at a dose of 30 g+/−20% to 90 g+/−20% (e.g. 55 g+/−20%) in the late evening with the composition. In some embodiments, the carbohydrate supplement can include a polysaccharide (e.g., maltodextrin (e.g., 50+/−20% g of maltodextrin)) and a fermentable fiber or prebiotic (e.g., one or both of beta-glucan (e.g., 2.5+/−20% g of beta-glucan) or resistant starch (e.g., 2.5+/−20% g of resistance starch)). In some embodiments, the carbohydrate supplement can be provided in a powder or liquid form and mixed with the composition for administration (e.g., at night) to a subject. In some embodiments, administration of the composition with the carbohydrate supplement supports overnight anabolic metabolism in a subject.

TABLE 6

Exemplary carbohydrate supplement for administration with the composition.

| Component | Grams | Est kcal/g | Est kcal | Exemplary Function in Composition |
|---|---|---|---|---|
| Maltodextrin | 50 | 4 | 200 | Polyaccharide as a major source of glucose and caloric content. |
| Beta-glucan | 2.5 | 4 | 10 | Fermentable fiber/prebiotic to slow absorption of glucose (from maltodextrin), provide additional caloric content, and promote restorative changes in gut microbiota. |
| Resistant Starch | 2.5 | 2 | 5 | Fermentable fiber/prebiotic to slow absorption of glucose (from maltodextrin), provide additional caloric content, and promote restorative changes in gut microbiota. |
| Total carbs/day | 55 | | | |
| Estimated cal/day | | | 215 | |

Production of Active Moiety and Pharmaceutical Compositions

The present disclosure features a method of manufacturing or making a composition (e.g., an Active Moiety) of the foregoing invention. Amino acid entities used to make the compositions may be agglomerated, and/or instantized to aid in dispersal and/or solubilization.

The compositions may be made using amino acid entities from the following sources, or other sources may used: e.g., FUSI-BCAA™ Instantized Blend (L-Leucine, L-Isoleucine and L-Valine in 2:1:1 weight ratio), instantized L-Leucine, and other acids may be obtained from Ajinomoto Co., Inc. Pharma. grade amino acid entity raw materials may be used in the manufacture of pharmaceutical amino acid entity products. Food (or supplement) grade amino acid entity raw materials may be used in the manufacture of dietary amino acid entity products.

To produce the compositions of the instant disclosure, the following general steps may be used: the starting materials (individual amino acid entities and excipients) may be blended in a blending unit, followed by verification of blend uniformity and amino acid entity content, and filling of the blended powder into stick packs or other unit dosage form. The content of stick packs or other unit dosage forms may be dispersed in water at time of use for oral administration.

When combining raw materials, e.g., pharmaceutical grade amino acid entities and/or excipients, into a composition, contaminants may be present in the composition. A composition meets a standard for level of contamination when the composition does not substantially comprise (e.g., comprises less than 10, 9, 8, 7, 6, 5, 4, 3, 2, 1, 0.1, 0.01, or 0.001% (w/w)) a contaminant. In some embodiments, a composition described in a method herein does not comprise a contaminant. Contaminants include any substance that is not deliberately present in the composition (for example, pharmaceutical grade amino acid entities and excipients, e.g., oral administration components, may be deliberately present) or any substance that has a negative effect on a product quality parameter of the composition (e.g., side effects in a subject, decreased potency, decreased stability/shelf life, discoloration, odor, bad taste, bad texture/mouthfeel, or increased segregation of components of the composition). In some embodiments, contaminants include microbes, endotoxins, metals, or a combination thereof. In some embodiments, the level of contamination, e.g., by metals, lecithin, choline, endotoxin, microbes, or other contaminants (e.g., contaminants from raw materials) of each portion of a composition is below the level permitted in food.

Excipients

The amino acid compositions of the present disclosure may be compounded or formulated with one or more excipients. Non-limiting examples of suitable excipients include a tastant, a flavorant, a buffering agent, a preservative, a stabilizer, a binder, a compaction agent, a lubricant, a dispersion enhancer, a disintegration agent, a flavoring agent, a sweetener, and a coloring agent.

In some embodiments, the excipient comprises a buffering agent. Non-limiting examples of suitable buffering agents include citric acid, sodium citrate, magnesium carbonate, magnesium bicarbonate, calcium carbonate, and calcium bicarbonate.

In some embodiments, the excipient comprises a preservative. Non-limiting examples of suitable preservatives include antioxidants, such as alpha-tocopherol and ascorbate, and antimicrobials, such as parabens, chlorobutanol, and phenol.

In some embodiments, the composition comprises a binder as an excipient. Non-limiting examples of suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, and combinations thereof.

In some embodiments, the composition comprises a lubricant as an excipient. Non-limiting examples of suitable lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

In some embodiments, the composition comprises a dispersion enhancer as an excipient. Non-limiting examples of suitable dispersants include starch, alginic acid, polyvinylpyrrolidones, guar gum, kaolin, xanthan gum, bentonite, purified wood cellulose, sodium starch glycolate, isoamorphous silicate, and microcrystalline cellulose as high HLB emulsifier surfactants.

In some embodiments, the composition comprises a disintegrant as an excipient. In some embodiments, the disintegrant is a non-effervescent disintegrant. Non-limiting examples of suitable non-effervescent disintegrants include starches such as corn starch, potato starch, pregelatinized and modified starches thereof, sweeteners, clays, such as bentonite, microcrystalline cellulose, alginates, sodium starch glycolate, gums such as agar, guar, locust bean, karaya, pecitin, and tragacanth. In some embodiments, the disintegrant is an effervescent disintegrant. Non-limiting examples of suitable effervescent disintegrants include sodium bicarbonate in combination with citric acid, and sodium bicarbonate in combination with tartaric acid.

Particular excipients may include one or more of: citric acid, lecithin, (e.g. Alcolec F100), sweeteners (e.g. sucralose, sucralose micronized NF, acesulfame potassium (e.g. Ace-K)), a dispersion enhancer (e.g. xanthan gum (e.g. Ticaxan Rapid-3)), flavorings (e.g. vanilla custard #4306, Nat Orange WONF #1326, lime 865.0032U, and lemon 862.2169U), a bitterness masking agent (e.g. 936.2160U), and natural or artificial colorings (e.g. FD&C Yellow 6). Exemplary ingredient contents for each stick pack are shown in Table 7.

TABLE 7

Ingredient contents in each stick pack.

| INGREDIENT | GRADE | FUNCTION | SOURCE; COMMENT |
|---|---|---|---|
| Amino Acids | USP | Active Pharmaceutical Ingredient (API) | Various sources; Non-instantized form (MFG scale) |
| Citric Acid | USP | pH, Flavor | Spectrum Chems; f(volume) ≤1.0% w/v |
| Acesulfame K | NF | Sweetness (rapid onset) | Spectrum Chems; Target 1 Sweetener |
| Sucralose | NF | Sweetness (slow onset) | Spectrum Chems; WHO ADI ≤15 mg/kg |
| Lecithin (Alecolec F100) | FCC | Wetting Agent | American Lecithin Company |
| Xanthan Gum | FCC | Stabilizer/Thickener | TIC Gums; f(volume) ≤0.5% w/v |
| Vanilla Custard (Art) | GRAS | Taste/Aroma | David Michael; Mask sulfur |
| Orange (Natural and WONF) | GRAS | 1° flavor | David Michael; Citrus profile matches low pH |
| Lime (Natural and WONF) | GRAS | 2° flavor | FONA; Single flavor supplier |
| Lemon (Natural and artificial) | GRAS | 2° flavor | FONA; Single flavor supplier |
| Taste Modifier | GRAS | Bitterness masking | FONA; Useful at low volume |
| FD&C Yellow No. 6 | USP | Color | Sensient; Match flavor profile |

In some embodiments, the excipient comprises a flavoring agent. Flavoring agents can be chosen from synthetic flavor oils and flavoring aromatics; natural oils; extracts from plants, leaves, flowers, and fruits; and combinations thereof. In some embodiments, the flavoring agent is selected from cinnamon oils; oil of wintergreen; peppermint oils; clover oil; hay oil; anise oil; eucalyptus; vanilla; citrus oil such as lemon oil, orange oil, grape and grapefruit oil; and fruit essences including apple, peach, pear, strawberry, raspberry, cherry, plum, pineapple, and apricot.

In some embodiments, the excipient comprises a sweetener. Non-limiting examples of suitable sweeteners include glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; Stevia Rebaudiana (Stevioside); chloro derivatives of sucrose such as sucralose; and sugar alcohols such as sorbitol, mannitol, sylitol, and the like. Also contemplated are hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof. In some embodiments, the composition comprises a coloring agent. Non-limiting examples of suitable color agents include food, drug and cosmetic colors (FD&C), drug and cosmetic colors (D&C), and external drug and cosmetic colors (Ext. D&C). The coloring agents can be used as dyes or their corresponding lakes.

In another embodiment, excipients are limited to citric acid, a sweetener (e.g., sucralose), xanthan gum, an aroma agent (e.g., vanilla custard #4036), a flavoring agent (e.g., Nat orange WONF #1362), and a coloring agent (e.g., FD&C Yellow 6), e.g., the excipient specifically excludes lecithin (Table 8).

TABLE 8

Exemplary contents in each stick pack.

| INGREDIENT | GRADE | FUNCTION |
|---|---|---|
| Amino Acids | USP | Active Pharmaceutical Ingredient (API) |
| Citric Acid | USP | pH, Flavor |
| Sucralose | NF | Sweetness (slow onset) |
| Xanthan Gum | FCC | Stabilizer/Thickener |
| Vanilla Custard (Art) | GRAS | Aroma |
| Orange (Nat + WONF) | GRAS | 1° flavor |
| FD&C Yellow No. 6 | USP | Color |

Dietary Compositions

The composition (e.g., Active Moiety) including amino acid entities can be formulated and used as a dietary composition, e.g., chosen from a medical food, a functional food, or a supplement. In such an embodiment, the raw materials and final product should meet the standards of a food product.

The composition of any of the aspects and embodiments disclosed herein can be for use as a dietary composition, e.g., chosen from a medical food, a functional food, or a supplement. In some embodiments, the dietary composition is for use in a method, comprising administering the composition to a subject. The composition can be for use in a dietary composition for the purpose of improving one, two, three, or more (e.g., all) of liver function, hyperammonemia, muscle mass, or muscle function in a subject.

In some embodiments, the dietary composition is chosen from a medical food, a functional food, or a supplement. In some embodiments, the composition is in the form of a nutritional supplement, a dietary formulation, a functional food, a medical food, a food, or a beverage comprising a composition described herein. In some embodiments, the nutritional supplement, the dietary formulation, the functional food, the medical food, the food, or the beverage comprising a composition described herein for use in the management of a liver disease or disorder with one or both of hyperammonemia or muscle wasting (e.g., cirrhosis, e.g., cirrhotic sarcopenia, End Stage Liver Disease, hepatic insufficiency, hepatic encephalopathy, or a combination thereof) in a subject.

The present disclosure features a method of improving one, two, three, four, five, six, seven, eight, nine, 10, 11, 12, 13, 14, 15, 16, 17, 18, or more (e.g., all) of hyperammonemia, ascites or complications associated with ascites, variceal bleeding, infection, hepatic encephalopathy, ammonia toxicity, hepatic insufficiency, decreased urea synthesis, inflammation of hepatic tissue, fibrosis, cirrhosis, muscle wasting, muscle catabolism, muscle atrophy, hypoalbuminemia, hypercatabolism, malnutrition, frailty, or coagulopathy, comprising administering to a subject an effective amount of a dietary composition described herein.

The present disclosure features a method of providing nutritional support or supplementation to a subject with a liver disease or disorder with one or both of hyperammonemia or muscle wasting, comprising administering to the subject an effective amount of a composition described herein.

The present disclosure features a method of providing nutritional support or supplementation that aids in the management of a liver disease or disorder with one or both of hyperammonemia or muscle wasting, comprising administering to a subject in need thereof an effective amount of a composition described herein.

In some embodiments, the subject has cirrhosis.

In some embodiments, the subject has cirrhotic sarcopenia. In some embodiments, the subject has hepatic insufficiency. In some embodiments, the subject has End Stage Liver Disease. In some embodiments, the subject has hepatic encephalopathy.

The compositions can be used in methods of dietary management of a subject (e.g., a subject without a liver disease or disorder with one or both of hyperammonemia or muscle wasting). In some embodiments, the subject does not have a liver disease or disorder with one or both of hyperammonemia or muscle wasting.

Biomarkers

Any of the methods disclosed herein can include evaluating or monitoring the effectiveness of administering a composition including amino acid entities to a subject, e.g., a subject having a liver disease or disorder with one or both of hyperammonemia or muscle wasting (e.g., cirrhosis, e.g., cirrhotic sarcopenia, End Stage Liver Disease, hepatic insufficiency, hepatic encephalopathy, or a combination thereof).

In embodiments, the value of effectiveness to the composition in treating a subject comprises a measure of one, two, three, four, five, six, seven, eight, nine, 10, 11 or more (e.g., all) of the following: a) the ratio of BCAAs to AAAs (e.g., the Fischer's ratio), b) a level of ammonia, c) a level of valine relative to a level of phenylalanine, d) a level of albumin (e.g. meal-induced albumin), e) a level of myostatin, f) a level or activity of mTOR, g) a level of creatinine, h) a level of bilirubin, i) a level of urinary 3-methylhistidine, j) a level of AMPK, k) a level of Gcn2, or l) a level of protein synthesis.

In some embodiments of any of the methods disclosed herein, the measure of one or more of a)-l) is obtained from a sample acquired from the subject. In some embodiments, the sample is chosen from a blood sample (e.g., a plasma sample), a liver sample, or a muscle sample.

In some embodiments, the subject is evaluated prior to receiving, during, or after receiving, a composition including defined amino acid components.

In some embodiments, the level of BCAAs and AAAs are determined using a Fischer's Ratio.

In some embodiments, administration of the composition results in one, two, three, four, five, six, seven, eight, nine, 10, 11, or more (e.g., all) of: a) increased level of BCAAs to AAAs (e.g., increased Fischer's ratio), b) decreased level of ammonia, c) an increased level of valine relative to a level of phenylalanine, d) an increased level of albumin (e.g. meal-induced albumin), e) a decreased level of myostatin, f) an increased level or activity of mTOR, g) a decreased level of creatinine, h) a decreased level of bilirubin, i) a decreased level of urinary 3-methylhistidine, j) a decreased level of AMPK, k) a decreased level of Gcn2, or l) an increased level of protein synthesis.

In some embodiments, administration of the composition results in an increase in amino acid entities (e.g., one, two, there, four, five, or six of L-valine, L-leucine, L-isoleucine, L-histidine, L-lysine, or L-threonine) in one, two, or more (e.g., all) of blood, plasma, or serum of the subject, e.g., in a blood, plasma, or serum sample from the subject.

In some embodiments, administration of the composition results in an improvement in one, two, three, four, five, six, seven, eight, nine, 10, 11, or more (e.g., all) of a)-l) after a treatment period of 24 hours (e.g., after 48 hours or 72 hours).

EXAMPLES

The Examples below are set forth to aid in the understanding of the inventions, but are not intended to, and should not be construed to, limit its scope in any way.

Example 1: Treatment of Hepatic Insufficiency Subjects with an Amino Acid Composition The study described herein features the administration of a composition including amino acids to subjects with mild to moderate hepatic insufficiency. The goal of this pre-IND and IRB approved study was to determine the safety and tolerability of an amino acid composition as well as its impact on the structure and function of human physiology by looking at various markers of amino acid metabolism, liver function/health, and ammonia detoxification, after 7 days and 14 days of administration. The composition included about 0.8889 g of L-leucine, about 0.4444 g of L-isoleucine, about 0.8889 g of L-valine, about 0.4703 g of L-lysine acetate (or about 0.3333 g of L-lysine), about 0.3333 g of L-histidine, about 0.3333 g of L-threonine, and about 1.6667 g of L-ornithine L-aspartate per stick packet, for administration in three stick packs three times per day (e.g., a total of about 44.1 g per day, or about 14.7 g three times per day). The total amounts (in grams) of the amino acids in the composition per stick pack are shown in Table 9.

TABLE 9

Components of the amino acid composition in grams (g) per individual stick pack.

| Amino Acid Entity | Total Amount (g) |
|---|---|
| L-Leucine | 0.8889 g |
| L-Isoleucine | 0.4444 g |
| L-Valine | 0.8889 g |
| L-Lysine Acetate | 0.4703 g |
| | (0.3333 g L-Lysine) |
| L-Histidine | 0.3333 g |
| L-Threonine | 0.3333 g |
| L-Ornithine L-Aspartate | 1.6667 g |

In this study, subjects received the amino acid composition three times daily for 14 days. Amino acids were provided in powder form to be dissolved in 8 oz. of water. Participants were given the amino acid composition for the 14 day study period.

Figure 2:
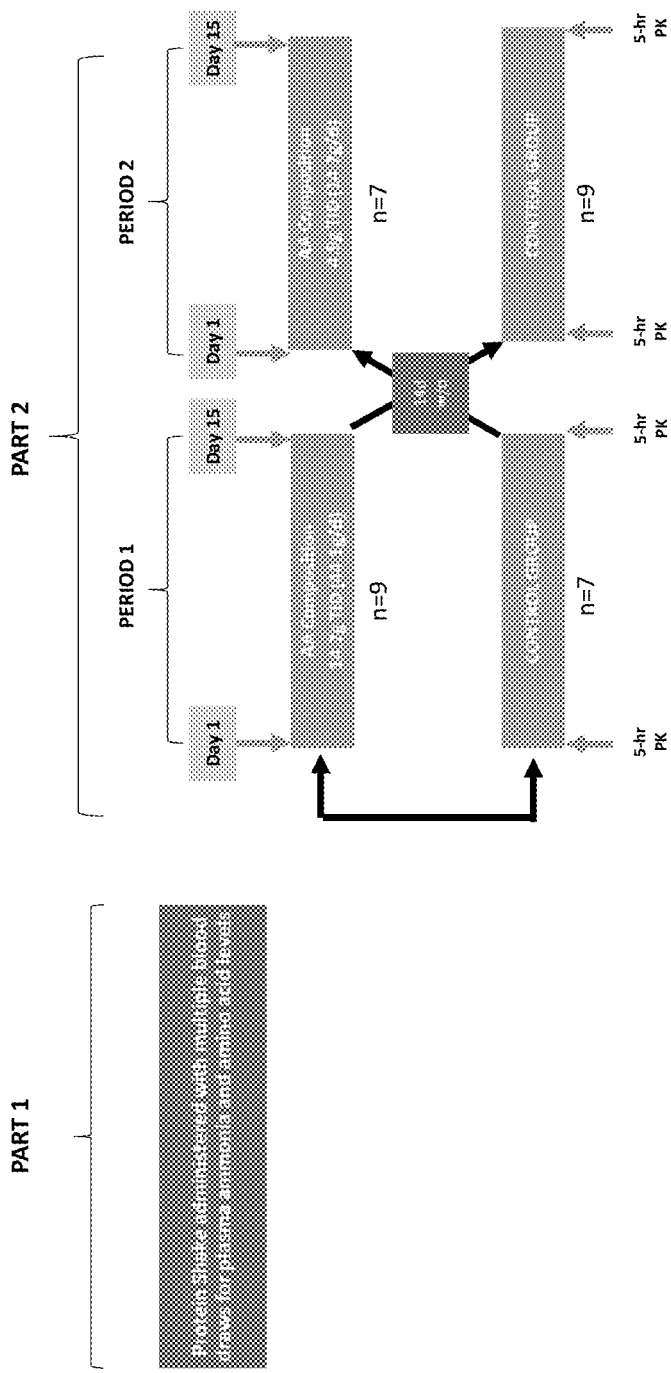
FIG. 2 is a schematic showing the design of a clinical study featuring the administration of an amino acid composition to subjects having hepatic insufficiency. Arrows indicate the crossover design for 2 different dosages (14.7 g TID and 4.9 g TID) of the amino acid composition (dosed over 15 days per period) with a control group. PK and physiological assessments of structure (body weight and composition) and function (hand grip, chair stand, and balance assessment) were determined on Day 1, Day 8, and Day 15 of each period.

The study described herein included Part 1 and 2 (FIG. 2). The purpose of Part 1 was to determine how subjects with mild to moderate hepatic insufficiency responded to a standard protein meal, e.g., with respect to endogenous amino acid levels. As part of the intended safety evaluation, plasma ammonia levels were assessed in response to this protein meal. After an overnight fast, vital signs, body weight/composition, hand grip strength, chair stand, and balance assessment of subject were measured, followed by a baseline blood draw, prior to administration of a standardized protein shake containing 35 g of protein. For 5 hours following the protein meal, blood samples were collected at specified time points to measure ammonia and plasma amino acids.

Part 2 featured a 2-period crossover design for two different amounts of the amino acid composition (dosed over 15 days per period) with natural history as control. During Part 2, subjects were administered the amino acid composition three times daily at two different amounts (14.7 g TID during Period 1 and 4.9 TID during Period 2 for 14 days each) (FIG. 2). Each administration was composed of 3 stick packs of the amino acid composition mixed into 8 oz. of water (by mixing or shaking for at least 30 sec before consumption), and administered orally three times per day, approximately one hour after breakfast, one hour after lunch, and one hour after dinner. During Period 2, each administration was composed of 1 stick pack of the amino acid composition mixed into 4 oz. of water (by mixing or shaking for at least 30 sec before consumption), and administered orally three times per day, approximately one hour after breakfast, one hour after lunch, and one hour after dinner.

In Period 1, the subjects from Part 1 were split into two groups: one group received 14.7 g of the amino acid composition administered TID plus a standardized bedtime snack (one LARABAR®) for 14 days. The second group received the standardized bedtime snack without the amino acid composition for 14 days. Following a washout of up to 14 days, subjects that received 14.7 g of the amino acid composition TID in Period 1 received only the standard bedtime snack in Period 2 and subjects that received the bedtime snack only in Period 1 received 4.9 g of the amino acid composition TID plus the standardized bedtime snack in Period 2. Body weight/composition, hand grip strength, plasma amino acid levels, serum total protein, albumin, total alpha-amino nitrogen, and urinary urea and alpha-amino nitrogen were determined.

The primary outcome measure of this study was safety and tolerability. The secondary outcome measures were to examine the impact on human physiology through biomarkers that pertain to amino acid metabolism and liver function. Assessments were performed at baseline (day 1), at day 8, and at day 15 of the study. Amino acid levels in plasma and ammonia levels in serum were measured using standard analytical methods in a clinical laboratory.

Dry lean mass was determined at day 1 and day 15. Body composition including dry lean mass was measured using the InBody 770 system, which measures intracellular and extracellular body water, lean, fat, and muscle mass.

Components of the liver frailty index (hand grip strength, chair stands, and balance) were measured at day 1 and day 15. Measures of full handgrip strength were taken using a calibrated hand dynamometer (Jamar). Subjects used their dominant hand to squeeze the dynamometer, then released, and repeated the test three times. The chair stand assessment measured the time that it took a subject to stand up and sit down in a chair 5 times without using their arms. Balance was tested in 3 positions for 10 seconds in each position. For each position, a stop watch was started when the subject's feet were in the correct pose and the subject let go of any support.

Results

Figure 3A:
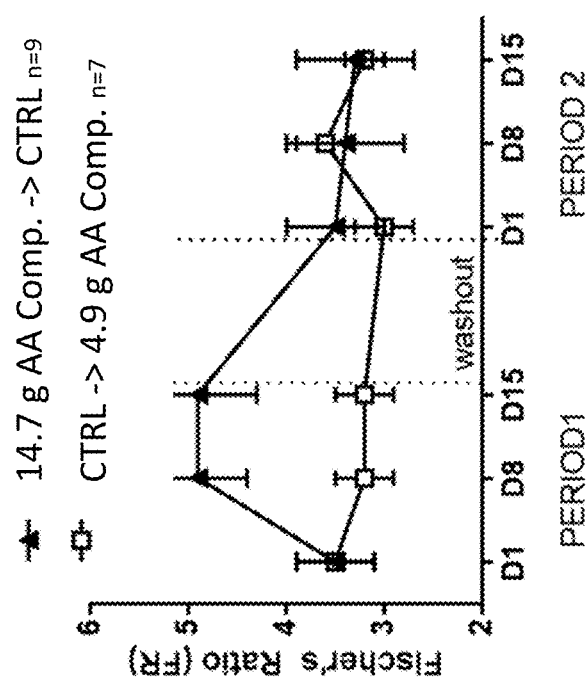
FIGS. 3A-3B are a series of graphs showing the Fischer's ratio (FR) and valine:phenylalanine ratio (VPR) of subjects on Day 1, Day 8, and Day 15 of Period 1 and Period 2 of the clinical study. Measurements are mean+/−standard error of the mean (SEM). The number of subjects in the 14.7 g TID amino acid composition to control group was 9. The number of subjects in the control to 4.9 g TID amino acid composition group was 7.
Figure 3B:
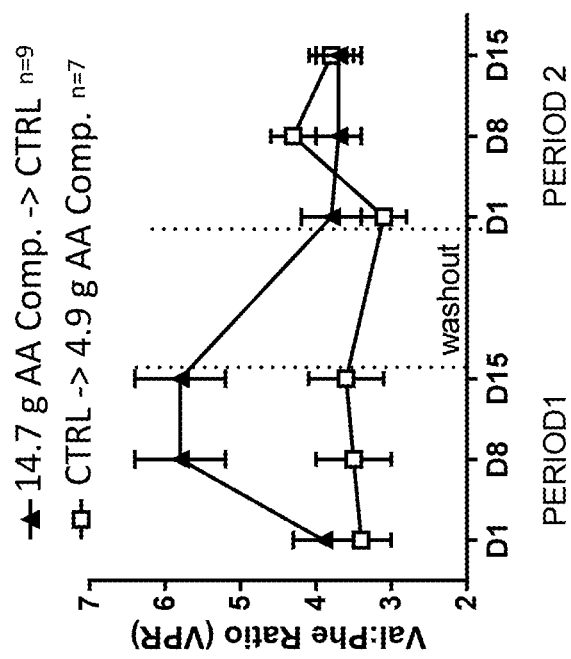
Figure 4A:
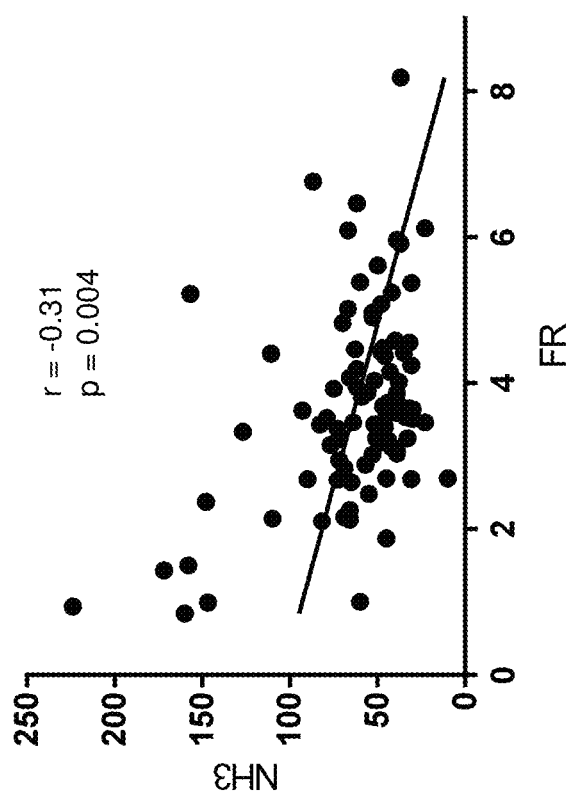
FIGS. 4A-4B are a series of graphs showing a negative correlation between levels of ammonia and the FR and VPR of subjects administered 14.7 g TID of the amino acid composition on Day 15 of Period 1 of the clinical study.
Figure 4B:
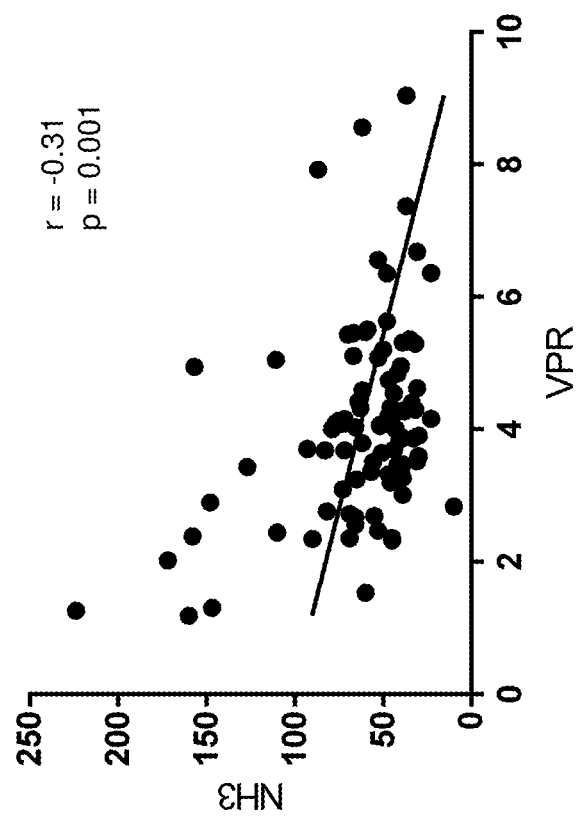

In Period 1, subjects administered 14.7 g of the amino acid composition TID demonstrated a robust 40-50% increase in the Fischer's ratio (FR) and valine:phenylalanine ratio (VPR) by Day 8 and these levels were maintained on Day 15 as compared to control group (FIG. 3A-3B). When the amino acid composition was washed out for 14 days, Fischer's ratio and VPR ratio levels returned to baseline. Following the washout, in period 2, when the same subjects in period 1 that were administered 14.7 g of the amino acid composition were crossed over to control, the increase in Fischer's ratio and VPR ratio was not observed. Subjects that were in the control group in Period 1, when crossed over to 4.9 g of the amino acid composition TID in Period 2 demonstrated minimal to no increase in Fischer's ratio or valine:phenylalanine ratio relative to the higher dose of the amino acid composition group. There was a strong negative correlation between ammonia and the FR or the VPR on Day 15 for the group administered 14.7 g of the amino acid composition, which suggests ammonia consumption during muscle protein synthesis (FIGS. 4A and 4B).

Figure 5A:
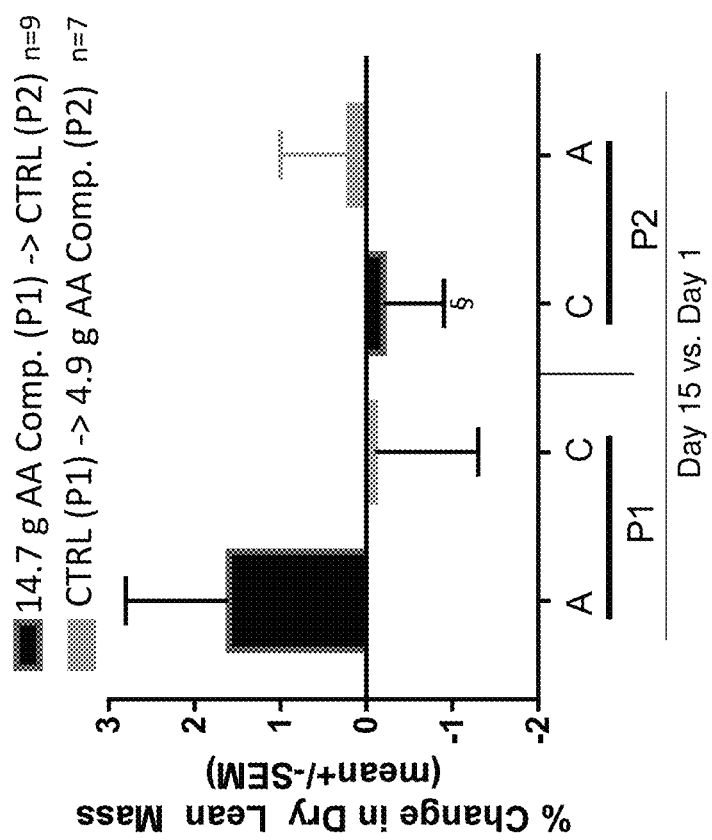
FIGS. 5A-5B are a series of graphs showing the % change of dry lean mass and Liver Frailty Index (LFI) of subjects on Day 15 vs. Day 1 of Period 1 (P1) and Period 2 (2) of the clinical study. A represents the amino acid composition group, and C represents the control group. Measurements are mean+/−SEM. The number of subjects in the 14.7 g TID amino acid composition to control group was 9. The number of subjects in the control to 4.9 g TID amino acid composition group was 7. § indicates that the improvement in lean mass or the liver frailty index appears to be lost once the amino acid composition was withdrawn. † indicates a relative improvement in LFI of 80% compared to the control group.
Figure 5B:
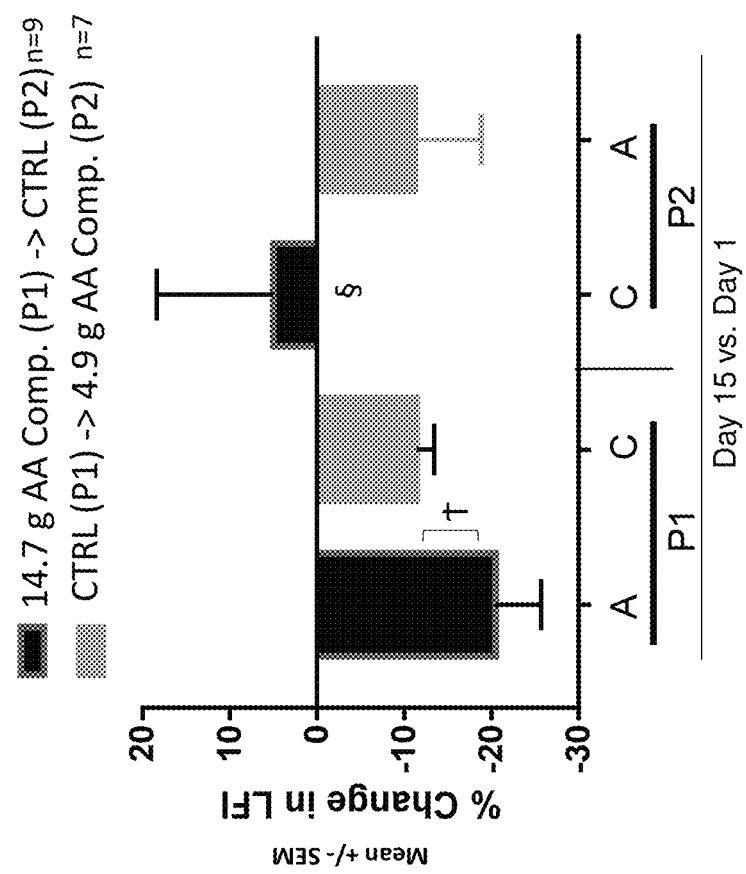

In Period 1, subjects administered 14.7 g of the amino acid composition TID demonstrated a robust 2% change in dry lean mass and 80% relative improvement in the Liver Frailty Index (LFI) at Day 15 relative to control group (FIG. 5A-5B). Following the washout, in period 2, when the same subjects in period 1 that were administered 14.7 g of the amino acid composition were crossed over to control, the increase in dry lean mass and decrease in the LFI was not observed. Thus, the improvement in lean mass and LFI appeared to be lost once administration of amino acid composition was withdrawn. Subjects that were in the control group in Period 1, when crossed over to 4.9 g of the amino acid composition TID in Period 2, demonstrated minimal to no increase in dry lean mass and minimal to no decrease in the LFI relative to the higher dose of the amino acid composition group.

Together these findings demonstrate a robust pharmacological effect of the amino acid composition on these parameters, and suggest that the amino acid composition has a favorable safety and tolerability profile and impacts biomarkers for the structure and function of the human body that relate to amino acid metabolism, improved liver function/health, and improved ammonia detoxification.

Example 2: ODLIVHKT Improves Basal BCAA Concentrations

Basal plasma concentrations of branched chain amino acids are measured in animals treated with ODLIVHKT or comparative constituents on day 1 and day 20 of treatment.

Rationale: Branched chain amino acids are depleted in plasma of patients with liver cirrhosis and low levels correlate with survival in end stage liver disease. BCAA depletion occurs because catabolism to glutamate for intramuscular ammonia detox is a consequence of failed nitrogen handling resulting from failed liver. Branched chain amino acids improve albumin in hypoalbuminemic cirrhotic individuals but have not been efficacious in other aspects of pathophysiology of cirrhosis. Valine levels are the most highly correlated with mortality in cirrhosis (Kinny-Koster 2015).

Methods: 8-week old Sprague-Dawley rats are subjected to bile duct ligation (BDL), a well-established model of cholestasis-induced liver cirrhosis. Three weeks post-bile duct ligation, the animals were hyperammonemic and displayed perturbed plasma amino acid profiles, and treatment with ODLIVHKT or constituent treatment groups (see Table 10 for treatment groups) was commenced by BID oral administration for 20 days. On Day 1 and Day 20 of the study animals were fed ad libitum overnight, food was removed 1 hour prior to administration of the amino acid compositions and blood was sampled at that time. Amino acid concentrations were measured from flash-frozen heparinized plasma samples.

TABLE 10

BDL Treatment Groups for Examples 2 to 5

| Group | Amino acid composition |
|---|---|
| 1 | Vehicle |
| 2 | LIV |
| 3 | LIVHKT |
| 4 | OD |
| 5 | ODLIVHKT |

Results: ODLIVHKT treatment resulted in an increase in basal BCAA levels on day 20 compared to day 1 while other treatment groups caused a worsening or no change (Table 11). Vehicle treated animals showed considerable reductions in the basal levels of Leucine, Isoleucine and Valine (all p values <0.1) on day 20 compared to day 1. Isoleucine levels significantly worsened over the treatment period for animals treated with LIV and LIVHKT, OD treated animals showed slight improvement, and ODLIVHKT treated animals showed the biggest increase in isoleucine concentrations. Leucine levels were significantly decreased on day 20 compared to day 1 for LIV and LIVHKT treated animals. OD treated animals showed no change in leucine concentrations, while ODLIVHKT animals showed increased basal levels that trend toward significance. Valine levels are significantly decreased on day 20 in LIV and LIVHKT treated animals compared to day 1 and OD treated animals decrease though no significantly. ODLIVHKT is the only treatment group that shows increases in basal valine levels on day 20 compared to day 1.

TABLE 11

Basal BCAA concentrations in BDL Rats

| Compound | Treatment group | Day | Mean plasma Concentration (uM) | Plasma Concentration standard deviation | n | p-value T-test Day 1 vs Day20 |
|---|---|---|---|---|---|---|
| Isoleucine | 1. Vehicle | 1 | 65.12 | 14.80 | 5 | 0.078 |
| | | 20 | 49.68 | 13.38 | 8 | |
| | 2. LIV | 1 | 85.97 | 9.31 | 5 | 0.034 |
| | | 20 | 65.50 | 17.25 | 8 | |
| | 3. LIVHKT | 1 | 98.77 | 13.74 | 5 | 0.001 |
| | | 20 | 53.95 | 20.10 | 8 | |
| | 4. OD | 1 | 74.85 | 22.15 | 5 | 0.382 |
| | | 20 | 90.12 | 31.01 | 6 | |
| | 5. ODLIVHKT | 1 | 58.37 | 20.51 | 5 | 0.075 |
| | | 20 | 86.98 | 23.66 | 5 | |
| Leucine | 1. Vehicle | 1 | 99.54 | 24.57 | 5 | 0.094 |
| | | 20 | 77.96 | 18.04 | 8 | |
| | 2. LIV | 1 | 131.25 | 14.27 | 5 | 0.007 |
| | | 20 | 93.00 | 23.32 | 8 | |
| | 3. LIVHKT | 1 | 160.03 | 24.84 | 5 | 0.000 |
| | | 20 | 73.12 | 25.07 | 8 | |
| | 4. OD | 1 | 137.67 | 42.96 | 5 | 0.955 |
| | | 20 | 136.06 | 48.51 | 6 | |
| | 5. ODLIVHKT | 1 | 98.72 | 36.55 | 5 | 0.178 |
| | | 20 | 134.39 | 39.79 | 5 | |
| Valine | 1. Vehicle | 1 | 138.78 | 34.07 | 5 | 0.071 |
| | | 20 | 108.41 | 21.31 | 8 | |
| | 2. LIV | 1 | 193.96 | 26.31 | 5 | 0.001 |
| | | 20 | 122.29 | 30.19 | 8 | |
| | 3. LIVHKT | 1 | 220.26 | 44.40 | 5 | 0.000 |
| | | 20 | 101.74 | 35.82 | 8 | |
| | 4. OD | 1 | 181.82 | 47.43 | 5 | 0.581 |
| | | 20 | 162.77 | 60.22 | 6 | |

TABLE 11-continued

| | | | | Basal BCAA concentrations in BDL Rats | | |
|---|---|---|---|---|---|---|
| Compound | Treatment group | Day | Mean plasma Concentration (uM) | Plasma Concentration standard deviation | n | p-value T-test Day 1 vs Day20 |
| | 5. ODLIVHKT | 1 20 | 147.57 166.33 | 51.29 51.28 | 5 5 | 0.579 |

Example 3: Amino Acid Composition Influences Pharmacokinetic Properties of Administered Amino Acids and Extended Treatment Results in Improved Amino Acid Metabolism Pharmacokinetic properties (maximum concentration, CMAX) of ODLIVHKT or constituent compositions were measured on Day1 and Day20.

Relevance: The balance between amino acid catabolism and protein synthesis is disrupted in cirrhotic individuals (Muller et al., 1999; Tessari et al., 2003). Responses to anabolic stimuli are diminished compared to healthy animals but how metabolism of specific amino acids is affected based on context of dosed amino acids is not known or appreciated (Tsien et al., 2015). Although LIV and LIVHKT were unable to prevent worsening of BCAA basal levels, ODLIVHKT treatment was able to increase levels in response to treatment (Example 2), but how BCAA metabolism is affected by LIV containing compositions is unknown.

Methods: 8-week old Sprague-Dawley rats were subjected to bile duct ligation (BDL), a well-established model of cholestasis-induced liver cirrhosis. Three weeks post-bile duct ligation, the animals were hyperammonemic and displayed perturbed plasma amino acid profiles, and treatment with ODLIVHKT or constituent treatment groups (see Table 10 for treatment groups) was commenced by BID oral administration for 20 days. On Day 1 and Day 20 of the study animals were fed ad libitum overnight, food was removed 1 hour prior to administration of the amino acid compositions and blood was sampled at that time. Blood was collected again prior to administration of the amino acid compositions and 0.25, 0.5, 1, 2, 3, and 4 hour thereafter. Basal amino acid concentrations were assessed from flash-frozen heparinized plasma samples using LC-MS based methodology. Maximum concentrations of LIV are measured over the 4 hour time course.

Results: Maximum concentration of LIV in response to amino acid administration declined on Day 20 compared to Day 1 in vehicle, LIV, and LIVHKT treated animals. OD administration maintained, or prevented the decrease in, LIV CMAX on day 20 compared to Day 1. ODLIVHT causes an increase in CMAX on day 20, the only treatment group that improves response to amino acid administration. Importantly, the highest CMAX observed was on day 20 in the ODLIVHKT treatment group (Table 12).

TABLE 12

| | | | | Unique pharmacokinetic properties of amino acid treatment groups | | |
|---|---|---|---|---|---|---|
| Compound | Treatment group | Day | Mean C-Max (uM) | C-Max standard deviation | n | p-value Ttest Day 1 vs Day20 |
| Isoleucine | 1. Vehicle | 1 | 99.70 | 11.52 | 5 | 0.000 |
| | | 20 | 55.76 | 13.70 | 8 | |
| | 2. LIV | 1 | 284.45 | 42.98 | 5 | 0.184 |
| | | 20 | 258.18 | 24.58 | 8 | |
| | 3. LIVHKT | 1 | 286.66 | 72.20 | 5 | 0.016 |
| | | 20 | 181.50 | 60.48 | 8 | |
| | 4. OD | 1 | 88.80 | 10.30 | 5 | 0.398 |
| | | 20 | 99.84 | 25.97 | 6 | |
| | 5. ODLIVHKT | 1 | 225.44 | 99.65 | 5 | 0.303 |
| | | 20 | 293.59 | 96.13 | 5 | |
| Leucine | 1. Vehicle | 1 | 152.63 | 24.08 | 5 | 0.000 |
| | | 20 | 86.76 | 20.28 | 8 | |
| | 2. LIV | 1 | 537.18 | 101.58 | 5 | 0.481 |
| | | 20 | 507.49 | 46.15 | 8 | |
| | 3. LIVHKT | 1 | 564.11 | 125.12 | 5 | 0.014 |
| | | 20 | 350.64 | 129.95 | 8 | |
| | 4. OD | 1 | 157.80 | 20.80 | 5 | 0.976 |
| | | 20 | 158.43 | 39.83 | 6 | |
| | 5. ODLIVHKT | 1 | 404.56 | 29.24 | 5 | 0.086 |
| | | 20 | 581.00 | 199.12 | 5 | |
| Valine | 1. Vehicle | 1 | 209.37 | 43.03 | 5 | 0.001 |
| | | 20 | 122.16 | 31.07 | 8 | |
| | 2. LIV | 1 | 862.61 | 120.90 | 5 | 0.526 |
| | | 20 | 811.23 | 146.20 | 8 | |
| | 3. LIVHKT | 1 | 899.55 | 191.25 | 5 | 0.036 |
| | | 20 | 599.15 | 235.63 | 8 | |
| | 4. OD | 1 | 200.05 | 22.97 | 5 | 0.716 |
| | | 20 | 190.96 | 49.62 | 6 | |

TABLE 12-continued

Unique pharmacokinetic properties of amino acid treatment groups

| Compound | Treatment group | Day | Mean C-Max (uM) | C-Max standard deviation | n | p-value Ttest Day 1 vs Day20 |
|---|---|---|---|---|---|---|
| | 5. ODLIVHKT | 1 | 668.28 | 61.14 | 5 | 0.059 |
| | | 20 | 892.89 | 220.51 | 5 | |

Example 4: Amino Acid Composition Reduces Tyrosine Exposure which is Associated with Disease Severity Effects on Basal AA Profiles of Cirrhotic Animals and Concentrations of Plasma Amino Acids Associated with and Mortality in Liver Cirrhosis Disposal of Tyrosine, which is associated with decreased liver function and mortality in liver disease was measured in response to treatment with ODLIVHKT or constituent treatment groups.

Relevance: Patients with end-stage liver disease have plasma amino acid concentrations that correlate with disease severity and survival in liver cirrhosis (Kinny-Koster et al., 2016). Aromatic amino acids are elevated in liver patients and correlate with overall mortality and have been predicted to promote hepatic encephalopathy (Soeters and Fischer et al., 1976). Tyrosine tolerance is disrupted in liver disease, and patients take longer to return to fasting levels with tyrosine ingestion (Levine and Conn, 1969).

Methods: 8-week old Sprague-Dawley rats were subjected to bile duct ligation (BDL), a well-established model of cholestasis-induced liver cirrhosis. Three weeks post-bile duct ligation, the animals were hyperammonemic and displayed perturbed plasma amino acid profiles, and treatment with ODLIVHKT or constituent treatment groups (see Table 10 for treatment groups) was commenced by BID oral administration for 20 days. On Day 1 and Day 20 of the study, animals were fed ad libitum overnight, food was removed 1 hour prior to administration of the amino acid compositions and blood was sampled at that time. Blood was collected again prior to administration of the amino acid compositions and 0.25, 0.5, 1, 2, 3, and 4 hour thereafter. Basal amino acid concentrations were assessed from flash-frozen heparinized plasma samples using LC-MS based methodology. Total exposure of amino acids was measured by subtracting baseline concentrations from each timepoint and then calculating the area under the curve (AUC) of the amino acid concentration during the four hour time course.

Results: Endogenous tyrosine levels were decreased with amino acid treatments as indicated by AUC values calculated over the time course (Table 13). On Day 1, all amino acid compositions decrease Tyrosine exposure at somewhat equivalent levels, LIVHKT had the greatest effect and vehicle administration had no effect. The highest clearance of tyrosine for the LIVHKT treated animals on day 1 is consistent with increased utilization for protein synthesis compared to the LIV composition, and suggests that addition of other essential amino acids may not be necessary. Interestingly, the ability of amino acid to decrease Tyrosine exposure became compromised over the 20 day treatment period, consistent with disease progression and worsened liver function. However, ODLIVHKT treatment group was the only group that showed an improvement compared to day 1, in other words the effect on decreasing tyrosine exposure with ODLIVHKT administration was better on Day 20 compared to Day 1 indicating that the treatment period had improved amino acid handling and metabolism. This is contrast to LIV, LIVHKT, and OD all of which had worsened handling of Tyrosine on Day 20 compared to Day 1. Moreover, ODLIVHKT trends toward significance when compared to vehicle treated groups while the other treatment groups showed no difference.

TABLE 13

Tyrosine exposure with amino acid administration

| Treatment group | Day | AUC mean | AUC sd | n | P value - two-way anova Day 20 compared to vehicle |
|---|---|---|---|---|---|
| 1. Vehicle | 1 | 55.01 | 164.2 | 5 | — |
| | 20 | -48.25 | 44.5 | 8 | — |
| 2. LIV | 1 | -247.32 | 125.3 | 5 | 0.9828 |
| | 20 | -73.03 | 74.9 | 8 | |
| 3. LIVHKT | 1 | -404.55 | 118.1 | 5 | 0.999 |
| | 20 | -59.33 | 133.4 | 7 | |
| 4. OD | 1 | -191.11 | 150.9 | 5 | 0.9238 |
| | 20 | -89.43 | 116.0 | 6 | |
| 5. ODLIVHKT | 1 | -80.24 | 170.4 | 5 | 0.1353 |
| | 20 | -192.03 | 125.0 | 5 | |

Example 5: Amino Acid Composition Improves Fischer's Ratio in Cirrhosis

Fischer's Ratio, the ratio of LIV to FY, is measured in response to treatment with ODLIVHKT or constituent treatment groups (Table 10)

Relevance: Patients with liver cirrhosis have altered plasma amino acid profiles owing to the disrupted and perturbed amino acid metabolism that results from liver failure. BCAAs L, I, and V, are highly depleted in liver cirrhosis and predictive of mortality. On the other hand, aromatic amino acids F and Y are enriched in liver patients and also predict mortality. A low Fischer's ratio is strong correlated with decreased survival of liver patients Methods: 8-week old Sprague-Dawley rats were subjected to bile duct ligation (BDL), a well-established model of cholestasis-induced liver cirrhosis. Three weeks post-bile duct ligation, the animals were hyperammonemic and displayed perturbed plasma amino acid profiles, and treatment with ODLIVHKT or constituent treatment groups (see Table 10 for treatment groups) was commenced by BID oral administration for 20 days. On Day 1 and Day 20 of the study, animals were fed ad libitum overnight, food was removed 1 hour prior to administration of the amino acid compositions and blood was sampled at that time. Amino acid concentrations were measured from flash-frozen heparinized plasma samples.

Results: Over the treatment period, LIV and LIVHKT treated animals had a greater than 25% worsening of their Fischer's ratio score. OD treated animals worsened by 5%. ODLIVHKT treated animals were the only group that showed an improved Fischer's Ratio in response to amino acid treatment which is surprising because all the constituent treatments worsened over the treatment period. ODLIVHKT treated animals had a greater than 20% improvement in their Fischer's Ratio (Table 14).

TABLE 14

Fischer's Ratio with amino acid treatment

| Group | Day | Fischer's Ratio (mean) | Fischer's Ratio (sd) | n | Fischer's Ratio % change |
|---|---|---|---|---|---|
| 1. Vehicle | 1 | 1.26 | 0.12 | 5 | 5.2 |
|  | 20 | 1.32 | 0.53 | 8 |  |
| 2. LIV | 1 | 1.82 | 0.82 | 5 | −27.3 |
|  | 20 | 1.32 | 0.55 | 8 |  |
| 3. LIVHKT | 1 | 1.61 | 0.45 | 5 | −29.0 |
|  | 20 | 1.14 | 0.48 | 8 |  |
| 4. OD | 1 | 1.78 | 0.70 | 5 | −5.6 |
|  | 20 | 1.68 | 0.96 | 6 |  |
| 5. ODLIVHKT | 1 | 1.50 | 0.41 | 5 | 22.2 |
|  | 20 | 1.83 | 0.84 | 5 |  |

Example 6: Amino Acid Composition Unexpectedly Influences Non-Essential Amino Acid (NEAA) Metabolism of Both Dosed (Aspartate) and Non-Dosed (Glutamate) Amino Acids with Acute and Prolonged Treatment, Suggesting Different Pharmacodynamic Properties Plasma concentrations of NEAAs (Aspartate and Glutamate) were measured in response to ODLIVHKT treatment and constituent comparators.

Relevance: Patients with liver cirrhosis have disrupted amino acid homeostasis and deregulated response to amino acid ingestion. Protein ingestion results in elevated ammonia production in cirrhosis due to hypercatabolism and anabolic resistance. Aspartate is an NEAA in the urea cycle important for nitrogen donation in urea production. Glutamate which is generated for Leucine, Isoleucine, Valine, and Aspartate, is an ammonia acceptor in skeletal muscle in a reaction producing glutamine. Aspartate and glutamate are formed from different essential amino acids and their concentrations indicate metabolic state of patients with liver disease.

Methods: 8-week old Sprague-Dawley rats were subjected to bile duct ligation (BDL), a well-established model of cholestasis-induced liver cirrhosis. Three weeks post bile duct ligation, the animals were hyperammonemic and displayed perturbed plasma amino acid profiles. Ad libitum fed animals were treated BID with ODLIVHKT or constituent treatment groups by oral gavage for 20 days and PK properties on Day 1 and Day 20 were assessed by measuring concentrations of NEAAs from flash-frozen heparinized plasma collected over a 5 hour treatment time course using LC-MS technology. CMAX is calculated as in Example 3.

Results: On Day 1, Vehicle treatment had no effect on CMAX of Aspartate relative to basal concentrations (20 uM, data not shown). LIV and LIVHKT resulted in a significant drop in Aspartate levels compared to vehicle. OD induced an increase in Aspartate to the highest concentration of all groups measured on Day 1, which is interesting because ODLIVHKT induces a smaller CMAX despite an equivalent amount of Aspartate being administered. On Day 20, the ability LIV or LIVHKT to cause a depletion in Aspartate was no longer observed. OD treatment resulted in a two-fold increase in CMAX compared to Day 1. Surprisingly, ODLIVHKT did not alter basal levels of Aspartate and the effect on CMAX was not changed compared to Day 1 (Table 15). Glutamate levels were not significantly influenced by vehicle, LIV, or LIVHKT on Day 1 or Day 20 but treatment with OD or ODLIVHKT significantly induced Glutamate CMAX. Surprisingly, the effect of 20 days of treatment resulted in a lowering of Glutamate CMAX in ODLIVHKT treatment group compared to Day 1, although treatment with OD alone continued to induce a significant amount glutamate. Taken together, the aspartate and glutamate levels induced by amino acid treatment suggest that amino acid metabolism and homeostasis had been considerably changed in the ODLIVHKT treatment group (Table 15).

TABLE 15

Pharmacokinetics of dosed and non-dosed NEAA constituents

| Compound | Treatment group | Day | Mean C-Max (uM) | C-Max standard deviation | n | p-value T-test Day 1 vs Day20 |
|---|---|---|---|---|---|---|
| Aspartic Acid | 1. Vehicle | 1 | 24.590 | 7.43 | 5 | 0.026 |
|  |  | 20 | 14.440 | 6.63 | 8 |  |
|  | 2. LIV | 1 | 4.029 | 5.54 | 5 | 0.000 |
|  |  | 20 | 25.933 | 7.06 | 8 |  |
|  | 3. LIVHKT | 1 | 4.642 | 4.92 | 5 | 0.007 |
|  |  | 20 | 20.406 | 9.79 | 8 |  |
|  | 4. OD | 1 | 48.152 | 21.19 | 5 | 0.010 |
|  |  | 20 | 87.580 | 19.34 | 6 |  |
|  | 5. ODLIVHKT | 1 | 27.781 | 30.55 | 5 | 0.731 |
|  |  | 20 | 32.869 | 9.54 | 5 |  |
| Glutamic Acid | 1. Vehicle | 1 | 53.635 | 9.51 | 5 | 0.127 |
|  |  | 20 | 32.767 | 26.83 | 8 |  |
|  | 2. LIV | 1 | 33.275 | 15.47 | 5 | 0.155 |
|  |  | 20 | 47.667 | 17.13 | 8 |  |
|  | 3. LIVHKT | 1 | 42.506 | 14.03 | 5 | 0.408 |
|  |  | 20 | 51.774 | 21.20 | 8 |  |
|  | 4. OD | 1 | 127.818 | 54.15 | 5 | 0.945 |
|  |  | 20 | 125.747 | 43.18 | 6 |  |
|  | 5. ODLIVHKT | 1 | 120.871 | 64.99 | 5 | 0.158 |
|  |  | 20 | 67.364 | 41.28 | 5 |  |

Example 7: Amino Acid Composition Effects on Cirrhosis-Induced Hyperammonemia Despite Nitrogen Load Provided Basal ammonia levels in animals treated with ODLIVHKT relative to other treatments, basal level differential day 1 to day 20 (ad libitum) and stable basal fasted levels at day 14 (fasted) will be measured.

Relevance: High protein diets are recommended for patients with liver cirrhosis, but protein ingestion results in increased plasma amino acid concentrations (Loza, 2014). Cirrhosis and portal hypertension result in increased plasma ammonia which both accelerate muscle wasting and induce hepatic encephalopathy (Dam et al., 2013). Lowering plasma ammonia levels has been a foundational strategy in the treatment and management of cirrhosis associated complications.

Methods: 8-week old Sprague-Dawley rats will be subjected to bile duct ligation (BDL), a well-established model of cholestasis-induced liver cirrhosis. Three weeks post bile duct ligation, the animals will be hyperammonemic and will display perturbed plasma amino acid profiles, and treatment with ODLIVHKT or constituent treatment groups (see Table 10) will be commenced by twice daily oral administration for 20 days. Flash-frozen heparinized plasma will be collected on Day 1 (ad libitum fed), Day 14 (fasted) and Day 20 (ad libitum fed) and ammonia will be measured according to manufacturer's instructions using a plate based assay (Abcam catalogue number Ab83360).

Ammonia concentrations in ODLIVHKT treated animals compared to constituent treatments will be measured.

Example 8: Additional Bile Duct Ligation Experiments (Generic Description of BDL Protocol and Measures)

Bile duct ligated rats will be used to model effects of amino acid compositions on pharmacokinetic and pharmacodynamic properties, including but not limited to markers of amino acid homeostasis, disease pathophysiology, disease histology, and functional consequences, in animals with liver cirrhosis.

Relevance: End-stage liver disease results in a complex pathophysiology arising from liver failure that has systemic consequences across all organs. As the liver is a critical organ for maintaining amino acid homeostasis, liver failure has profound dysregulation of plasma amino acid concentrations which are associated with disease severity and mortality. As the largest reservoir of protein in the body, skeletal muscle is a critical source of amino acids and profound wasting is observed in patients with liver source and skeletal muscle mass predicts mortality in cirrhotic patients. Bile duct ligation is a well-accepted model of cholestasis-induced liver disease that manifests with hyperammonemia and dysregulation of plasma amino acids. Muscle mass and function worsen over time in the BDL rat. As such, the BDL rat is a useful pre-clinical model to understand the complex pathophysiology arising from liver failure and examine consequences of various interventions on multi-systemic effects and markers of disease Methods: 6-week old rats will be subjected to a surgical procedure where a section of the bile duct is isolated, ligated, and cauterized. Starting one to two weeks post-surgery, the animals will be treated twice daily by oral gavage with amino acid compositions (e.g. amino acid composition treatments as in Table 10 and/or Table 16) for one month.

Pharmacokinetic properties of the amino acid compositions will be assessed in both the fed and fasted state at the beginning, middle, and end of the treatment period. Pharmacokinetic analysis will be performed by collecting blood from the jugular vein in heparin tubes prior to and 0.25 hr, 0.5 hr, 1 hr, 1.5 hr, 2 hr, 3 hr, and 4 hr after administration of the amino acid composition. Plasma amino acid concentrations will be assessed by LC-MS or an equivalent method. In addition, plasma will be analyzed for ammonia levels, cytokine and chemokine levels (e.g., TNF, IL-6, etc.), markers of liver damage (e.g. ALT, AST), and protein (e.g. Total, albumin, etc).

Muscle function will be measured by assessing forelimb and hindlimb grip strength using a standard meter and testing at the beginning, middle, and end of the treatment period. At the end of the study, hindlimb muscles will be collected, weighed, and embedded in OCT freezing medium. Thin cryosections will be prepared and immunostained or stained with hematoxylin and eosin (H&E), and muscle mass will be assessed by quantifying the cross-sectional area of myofibers of each muscle in the section.

Effects on liver function will be assessed by collecting the entire liver at the end of the study, weighing it, and preparing it for paraffin embedding by fixing specific lobes in 10% formalin overnight. H&E staining, staining for fibrosis (Sirius Red), Inflammation, and other standard measures and routine assessments will be made.

Effects on amino acid homeostasis will be assessed using targeted metabolite profiling and untargeted metabolomics of plasma, liver and muscle. Plasma collections at the beginning, middle, and end of the study will serve to measure disease progression and tissue analysis will be used to determine further consequences of treatment with various amino acid compositions.

Example 9: Amino Acid Composition Effects on Hepatic Albumin Production in Cirrhosis-Induced Hypoalbuminemia Media composed of amino acids consistent with profiles of cirrhotic individuals was tested for effect on production of albumin. Effects of ODLIVHKT, components and comparator compositions on albumin production were determined.

Relevance: Plasma amino acid concentrations are disrupted in patients with liver cirrhosis and predict mortality in end stage liver disease (Kinny-Koster et al., 2016). Plasma albumin levels are an important metric in Child's-Pugh scoring of liver disease severity and malnutrition which results in hypoalbuminemia is a significant complication of liver cirrhosis (Loza, 2014). BCAAs (specifically LIVact) has been approved outside the United States for the treatment of hypoalbuminemia in liver cirrhosis.

Methods: The ability of ODLIVHKT to increase hepatocyte albumin production was assessed using the C3A derivative clone of the HepG2 Hepatocellular Carcinoma cell line (ATCC, CRL-10741). 2.0e4 cells per well were seeded on day 0 in a 96-well microplate (Corning; 3903) in Dulbecco's Modified Eagle Medium (DMEM, Corning) supplemented with 10% fetal bovine serum (Corning) and 0.2% Primocin (InVivoGen, San Diego, Calif.) and incubated for 24 hours at 37° C., 5% $CO_2$. On day 1, the cell medium was replaced with amino acid free DMEM (US Biologicals, Salem, Mass.) supplemented with 0.1% heat inactivated fetal bovine serum (HI-FBS, HyClone), 100 ug/mL Primocin (InVivoGen), amino acids supplemented at 0.5× concentrations relative to plasma levels consistent with rations observed in cirrhotic individuals (Kakazu et al., 2013) and a dose curve of defined amino acid compositions at 5×, 10×, 20× and 40× of basal media concentrations was added to the cells (see Table 16). Cells were cultured for 48 hours at 37° C., 5% $CO_2$, media was collected, cells were washed 1× in PBS, fixed in 4% paraformaldehyde, washed 2× in PBS, nuclei were stained with Hoechst 33342 according to manufacturer's instructions (Life Technologies, H3570) and then washed 2× in PBS. Media albumin levels were assessed by R&D Systems's DuoSet ELISA Development System for Human Serum Albumin (R&D Systems, DY1455) and nuclei were counted using Molecular Devices Image Express High Content Screening platform and pre-installed nuclei counting analysis pipeline. Albumin levels were normalized to total nuclei in order to derive a per cell albumin production ratio.

Albumin production was determined in ODLIVHKT, constituent and comparator treated cells. Results: The composition comprising ODLIVHKT had significant albumin promoting activity in the context of cirrhosis-induced hypoalbuminemia in vitro. This is a surprising observation in the context that OD and HKT had mild inhibitory activity, while ODHKT was a potent inhibitor of albumin production. However, when combined together ODLIVHKT had more potent and significant albumin producing activity than the LIV combination alone.

TABLE 16

Treatment groups for Examples 9 and 10

1. L
2. LIV
3. HKT
4. LIVHKT
5. LIVHKTFMW
6. OD
7. ODLIV
8. ODHKT
9. ODLIVHKT
10. ODLIVHKTFMW
11. OLIV
12. OLIVHKT
13. DLIVHKT

Note:
I, D, H, K, T present at levels indicated by dose, L, V present at level 2x indicated by dose, 0 present at levels equivalent to D

TABLE 17

Cirrhosis-induced hypoalbuminemia (Example 9)

| Treatment Group | Dose | Albumin/Nuclei (mean) | Albumin/Nuclei (sd) | n | p-value Rel to ctrl | Effect on Albumin |
|---|---|---|---|---|---|---|
| L | 5X | −0.087 | 0.532 | 6 | 0.704 | No Effect |
|  | 10X | −0.116 | 0.259 | 6 | 0.320 |  |
|  | 20X | −0.219 | 0.676 | 6 | 0.463 |  |
|  | 40X | 0.148 | 0.519 | 6 | 0.516 |  |
| LIV | 5X | 0.265 | 0.607 | 6 | 0.334 | Promotes |
|  | 10X | 0.244 | 0.540 | 6 | 0.319 |  |
|  | 20X | 0.172 | 0.309 | 6 | 0.230 |  |
|  | 40X | 0.612 | 0.249 | 6 | 0.002 |  |
| HKT | 5X | 0.182 | 0.374 | 6 | 0.287 | Inhibits |
|  | 10X | −0.164 | 0.424 | 6 | 0.388 |  |
|  | 20X | −1.121 | 0.269 | 6 | 0.000 |  |
|  | 40X |  | TOXIC |  |  |  |
| LIVHKT | 5X | 0.031 | 0.628 | 6 | 0.907 | No effect |
|  | 10X | 0.146 | 0.536 | 6 | 0.535 |  |
|  | 20X | 0.511 | 0.691 | 6 | 0.130 |  |
|  | 40X | 0.389 | 0.587 | 6 | 0.166 |  |
| LIVHKTFMW | 5X | 1.184 | 0.285 | 6 | 0.000 | Promotes |
|  | 10X | 0.503 | 0.403 | 6 | 0.028 |  |
|  | 20X | 0.119 | 0.325 | 6 | 0.409 |  |
|  | 40X | −0.690 | 0.853 | 6 | 0.104 |  |
| OD | 5X | −0.082 | 0.107 | 6 | 0.118 | Inhibits |
|  | 10X | −0.279 | 0.357 | 6 | 0.114 |  |
|  | 20X | −0.135 | 0.406 | 6 | 0.451 |  |
|  | 40X | −0.409 | 0.369 | 6 | 0.042 |  |
| ODLIV | 5X | −0.243 | 0.316 | 6 | 0.118 | no effect |
|  | 10X | −0.074 | 0.310 | 6 | 0.583 |  |
|  | 20X | −0.177 | 0.340 | 6 | 0.258 |  |
|  | 40X |  | TOXIC |  |  |  |
| ODHKT | 5X | −0.112 | 0.411 | 6 | 0.535 | Inhibits |
|  | 10X | −0.193 | 0.277 | 6 | 0.149 |  |
|  | 20X | −0.621 | 0.341 | 6 | 0.007 |  |
|  | 40X | −1.781 | 0.803 | 6 | 0.003 |  |
| ODLIVHKT | 5X | 0.188 | 0.470 | 6 | 0.372 | Promotes |
|  | 10X | 0.397 | 0.347 | 6 | 0.038 |  |
|  | 20X | 0.368 | 0.428 | 6 | 0.089 |  |
|  | 40X | 0.587 | 0.421 | 6 | 0.019 |  |
| ODLIVHKTFMW | 5X | 0.505 | 0.324 | 6 | 0.012 | Promotes |
|  | 10X | 0.828 | 0.473 | 6 | 0.008 | (low dose) |
|  | 20X | 0.117 | 0.312 | 6 | 0.400 | Inhibits |
|  | 40X | −1.023 | 0.245 | 6 | 0.000 | (high dose) |
| OLIV | 5X | −0.088 | 0.145 | 6 | 0.197 | Promotes |
|  | 10X | 0.009 | 0.184 | 6 | 0.907 |  |
|  | 20X | 0.717 | 0.515 | 6 | 0.019 |  |
|  | 40X | 0.607 | 0.353 | 6 | 0.008 |  |
| OLIVHKT | 5X | −0.214 | 0.317 | 6 | 0.160 | Promotes |
|  | 10X | 0.163 | 0.282 | 6 | 0.216 |  |

TABLE 17-continued

Cirrhosis-induced hypoalbuminemia (Example 9)

| Treatment Group | Dose | Albumin/Nuclei (mean) | Albumin/Nuclei (sd) | n | p-value Rel to ctrl | Effect on Albumin |
|---|---|---|---|---|---|---|
| | 20X | 0.283 | 0.303 | 6 | 0.071 | |
| | 40X | 0.324 | 0.370 | 6 | 0.084 | |
| DLIVHKT | 5X | 0.115 | 0.338 | 6 | 0.442 | Promotes |
| | 10X | 0.333 | 0.288 | 6 | 0.037 | |
| | 20X | 0.597 | 0.259 | 6 | 0.002 | |
| | 40X | 0.178 | 0.322 | 6 | 0.235 | |

Example 10: OLIV Ameliorates TNF-Induced Defects in Myoblast Fusion

Relevance: Patients with liver cirrhosis and concomitant muscle wasting (Cirrhotic Sarcopenia, CS) are especially susceptible to co-morbidities and complications associated with end stage liver disease. Muscle wasting in cirrhosis is multifactorial and complex but driven by inflammation, altered plasma amino acid availability, hyperammonemia, and myostatin expression. TNFalpha drives myostatin expression and inhibits protein synthesis both of which are important pathologies CS (Qiu et al., 2013).

Methods: Experiment was performed using the MYO-SCREEN™ platform (CYTOO, France). Briefly, MYO-SCREEN™ is a proprietary technology based on micropatterning and defined microenvironments that establish highly mature primary human myotubes with substantial striation and low morphological variability. Primary cells derived from skeletal muscle of healthy human donors are differentiated to form myotubes (multinucleated syncytia) that are highly reminiscent of human muscle tissue. MYO-SCREEN™ is a fully automated platform that interrogates multiple phenotypes relevant for muscle physiology including myotube area, fusion index, and total nuclei.

On Day 0 expanded primary myoblasts from a healthy human donor were seeded at 10,000 cells per well for 24 hour at 37 deg C. On Day 1, cells were incubated according to Cytoo's instructions/protocol in differentiation media based on DMEM comprising 0.1% horse serum and containing indicated amino acid combinations (Table 16) at 4×, 10×, 20×, and 30× of the concentration in the cirrhosis media or with IGF-1 (150 ng/mL) as a positive control. Importantly, treatment groups were prepared in PBS and final concentration in all wells, including controls, was 10% PBS.

On Day 2 cells were switched to Cirrhosis Media based on DMEM comprising 0.1% horse serum and 0.5× amino acids at ratios of plasma of cirrhosis (Kakazu et al., 2013) containing atrophy inducer TNFalpha (10 ng/mL) and again treated according to Day 1 and Table 16. On Day 6 cells were fixed with 5% Formalin for 30 minutes at room temperature. Fixed cells were processed for immunostaining with primary antibody against Troponin T to stain myotubes and Hoeschst dye for nuclei. Image acquisition was done at 10× magnification using Operetta High Content Imaging System and analysis was performed using a proprietary and dedicated algorithm on the Acapella High Content Imaging System (Perkin Elmer, CYTOO).

Results: Five amino acid compositions promoted atrophy in response to TNF: HKT, LIVHKTFMW, ODHKT, ODLIVHKTFMW, DLIVHKTFMW. Atrophy promoting compositions contained essential amino acids H, K, T, F, M, W. Importantly the atrophy inducing activity of HKT was only observed at the highest dose levels this effect was ameliorated when combined with ODLIV to comprise the ODLIVHKT composition that is the focus of this application. Moreover, the atrophy promoting activity of EAAs was maintained with ODLIV when FMW were also present which serves as stronger rationale for the exclusion of MFW from the amino acid composition. Interestingly, only one composition was able to significantly reduce atrophy that was induced by TNF alpha, OLIV. In line with this observation, combinations containing OLIV perform worse in the atrophy assay when aspartate (D) is present (e.g. ODLIV). These observations suggest that high levels of OLIV are able reduce atrophy and prevent atrophy-inducing activity of HKT activity at high doses. From these observations it is concluded that lower levels of essential amino acids are to be combined with higher levels of OLIV to form a maximally efficacious combination.

TABLE 18

TNF induced myotube atrophy (Example 10)

| Treatment Group | Dose | N | Fusion Index | | | Myotube Area | | | Effect on Atrophy |
| | | | mean | sd | p Value Rel to ctrl | mean | sd | p Value Rel to ctrl | |
|---|---|---|---|---|---|---|---|---|---|
| L | 30X | 3 | 0.092 | 0.004 | ns | 4579.231 | 34.450 | ns | no effect |
| | 20X | 3 | 0.091 | 0.010 | ns | 4679.729 | 607.356 | ns | |
| | 10x | 3 | 0.094 | 0.004 | ns | 4480.850 | 247.066 | ns | |
| | 5X | 3 | 0.087 | 0.008 | ns | 4499.140 | 82.537 | ns | |
| LIV | 30X | 3 | 0.089 | 0.002 | ns | 4575.922 | 200.106 | ns | no effect |
| | 20X | 3 | 0.090 | 0.009 | ns | 4236.517 | 638.328 | ns | |
| | 10x | 3 | 0.098 | 0.009 | ns | 4606.486 | 138.861 | ns | |
| | 4X | 3 | 0.070 | 0.005 | ns | 4185.897 | 389.395 | ns | |
| HKT | 30X | 3 | 0.055 | 0.004 | ** | 3263.231 | 252.763 | ns | Promotes |
| | 20X | 3 | 0.069 | 0.015 | ns | 3522.930 | 639.455 | ns | |
| | 10x | 3 | 0.069 | 0.014 | ns | 3916.858 | 476.721 | ns | |
| | 4X | 3 | 0.064 | 0.011 | ns | 3883.118 | 606.967 | ns | |

TABLE 18-continued

TNF induced myotube atrophy (Example 10)

| Treatment Group | Dose | N | Fusion Index mean | sd | p Value Rel to ctrl | Myotube Area mean | sd | p Value Rel to ctrl | Effect on Atrophy |
|---|---|---|---|---|---|---|---|---|---|
| LIVHKT | 30X | 3 | 0.057 | 0.004 | ns | 3444.098 | 674.328 | ns | no effect |
|  | 20X | 3 | 0.067 | 0.002 | ns | 3805.351 | 130.059 | ns |  |
|  | 10x | 3 | 0.067 | 0.008 | ns | 3468.788 | 274.967 | ns |  |
|  | 4X | 3 | 0.074 | 0.008 | ns | 3660.795 | 536.539 | ns |  |
| LIVHKTFMW | 30X | 3 | 0.060 | 0.008 | *** | 3925.155 | 271.955 | ns | Promotes |
|  | 20X | 3 | 0.069 | 0.005 | * | 3478.838 | 493.485 | ns |  |
|  | 10x | 3 | 0.075 | 0.005 | ns | 4348.045 | 558.006 | ns |  |
|  | 4X | 3 | 0.075 | 0.001 | ns | 4192.110 | 127.880 | ns |  |
| OD | 30X | 3 | 0.075 | 0.006 | ns | 4051.888 | 226.568 | ns | no effect |
|  | 20X | 3 | 0.080 | 0.001 | ns | 4431.503 | 920.363 | ns |  |
|  | 10x | 3 | 0.080 | 0.011 | ns | 3820.013 | 523.558 | ns |  |
|  | 4X | 3 | 0.077 | 0.007 | ns | 3920.680 | 249.408 | ns |  |
| ODLIV | 30X | 3 | 0.084 | 0.010 | ns | 4282.417 | 76.449 | ns | no effect |
|  | 20X | 3 | 0.085 | 0.013 | ns | 4191.100 | 762.571 | ns |  |
|  | 10x | 3 | 0.079 | 0.019 | ns | 3709.459 | 928.450 | ns |  |
|  | 4X | 3 | 0.085 | 0.005 | ns | 3722.999 | 374.231 | ns |  |
| ODHKT | 30X | 3 | 0.061 | 0.004 | * | 3684.651 | 450.573 | ns | Promotes |
|  | 20X | 3 | 0.060 | 0.002 | * | 3507.377 | 138.827 | ns |  |
|  | 10x | 3 | 0.055 | 0.007 | ** | 3101.190 | 413.936 | * |  |
|  | 4X | 3 | 0.065 | 0.006 | ns | 3653.910 | 262.316 | ns |  |
| ODLIVHKT | 30X | 3 | 0.063 | 0.011 | ns | 3631.053 | 334.554 | ns | no effect |
|  | 20X | 3 | 0.072 | 0.003 | ns | 3742.228 | 188.088 | ns |  |
|  | 10x | 3 | 0.075 | 0.004 | ns | 3702.738 | 123.149 | ns |  |
|  | 4X | 3 | 0.083 | 0.008 | ns | 3880.888 | 120.571 | ns |  |
| ODLIVHKTFMW | 30X | 3 | 0.054 | 0.008 | ** | 3241.510 | 208.275 | ** | Promotes |
|  | 20X | 3 | 0.066 | 0.004 | ns | 3753.753 | 195.129 | ns |  |
|  | 10x | 3 | 0.069 | 0.004 | ns | 3559.084 | 312.937 | ns |  |
|  | 4X | 3 | 0.063 | 0.003 | ns | 3632.304 | 202.403 | ns |  |
| OLIV | 30X | 3 | 0.090 | 0.011 | ns | 4475.513 | 300.512 | ns | REDUCES |
|  | 20X | 3 | 0.100 | 0.020 | * | 3971.022 | 107.047 | ns |  |
|  | 10x | 3 | 0.096 | 0.010 | * | 4169.086 | 495.358 | ns |  |
|  | 4X | 3 | 0.074 | 0.005 | ns | 3714.271 | 521.271 | ns |  |
| OLIVHKT | 30X | 3 | 0.066 | 0.008 | ns | 3313.880 | 22.068 | ns | no effect |
|  | 20X | 3 | 0.080 | 0.010 | ns | 3686.219 | 166.702 | ns |  |
|  | 10x | 3 | 0.066 | 0.009 | ns | 3518.345 | 123.865 | ns |  |
|  | 4X | 3 | 0.069 | 0.004 | ns | 3492.752 | 253.222 | ns |  |
| DLIVHKT | 30X | 3 | 0.067 | 0.002 | ** | 3473.320 | 349.476 | ** | Promotes |
|  | 20X | 3 | 0.060 | 0.010 | ns | 3181.747 | 231.378 | ns |  |
|  | 10x | 3 | 0.070 | 0.002 | ns | 3641.507 | 831.654 | ns |  |
|  | 4X | 3 | 0.075 | 0.005 | ns | 3631.062 | 116.719 | ns |  | p Values generated by one-way Anova compared to control condition
* $p < .05$
** $p < .01$
*** $p < .001$

SUMMARY

Results in in vitro model systems (hepatocytes and myotubes) combined with pharmacokinetic profiles of amino acids highlighted the importance of considering doses, potential interactions, and target tissues when designing combinations.

In the case of ornithine and aspartate, ornithine is beneficial in both liver (Examples 2-6 and 9) and muscle model systems (Example 10) while aspartate is only beneficial to the liver model (Example 2-6 and 9). In this context the surprising PK profile of ODLIVHKT minimizing D exposure to peripheral tissues is highly relevant. Pharmacokinetic (PK) results from BDL and healthy rats and humans with mild hepatic insufficiency demonstrate that the composition ODLIVHKT reduces overall peripheral exposure of D while maintaining exposure of 0. Since ODLIVHKT is administered by oral dosing, it is predicted here that portal circulation should contain higher levels of D and achieve desired exposure to the liver while limiting exposure to the muscle tissue. Administration of equivalent doses of OD alone results in an approximately four-fold increase in plasma D whereas an equivalent dose as part of the composition ODLIVHKT results in less than two-fold increase.

In the case of HKT, compositions containing high doses of HKT performed worse in both the myotube atrophy and hepatic albumin production assays. The negative effects of HKT are diminished when combined with ODLIV at high doses. Since essential amino acids HKT are necessary to support protein synthesis, a desired PD response of ODLIVHKT, these amino acids should be dosed at lower ratios than ODLIV in order to achieve efficacy and minimize negative effects.

Therefore, ODLIV should be included in the composition in higher amounts than HKT. In other words, HKT should be dosed at lower ratios than ODLIV. The composition should comprise more of ODLIV than of H, K and/or T. For example, the composition could comprise about 2:1 ODLIV to HKT, or at least 50 to 66% ODLIV and at most 20 to 33% HKT.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

What is claimed is:

1. A composition comprising:
   a) a Branched Chain Amino Acid (BCAA) entity chosen from a leucine amino acid entity, an isoleucine amino acid entity, a valine amino acid entity, or a combination of two or three BCAA entities;
   b) a Urea Cycle Amino Acid (UCAA) entity chosen from an ornithine amino acid entity chosen from L-ornithine or a salt thereof, citrulline, or a combination of either thereof; an aspartate amino acid entity; or a combination of two UCAA entities; and
   c) an essential amino acid (EAA) entity chosen from a histidine amino acid entity, a lysine amino acid entity, or a threonine amino acid entity or a combination of two or three EAA entities;
   wherein:
   i) at least one amino acid entity of (a)-(c) is not provided as a peptide of more than 20 amino acid residues in length;
   ii) the total weight (wt.) % of (a)-(c) is greater than the total wt. % of non-protein components or other protein components in the composition on a dry weight basis;
   iii) one or two of tyrosine or glutamine, if present, is present at less than 1 wt. % of the total wt. of the composition on a dry weight basis; and
   iv) two or three of phenylalanine, methionine, or tryptophan are absent from the composition.

2. The composition of claim 1, wherein two, three, four, five, six, seven, or eight amino acid entities of (a)-(c) is not provided as a peptide of more than 20 amino acid residues in length.

3. The composition of claim 1, wherein the composition does not comprise a peptide of more than 20 amino acid residues in length, or if a peptide of more than 20 amino acid residues in length is present, the peptide is present at less than 10 wt. % of the total wt. of amino acid entities in the composition in dry form.

4. The composition of claim 1, wherein three, four, five, six, seven, or eight amino acid entities in (a)-(c) are in one or both of free amino acid form or salt amino acid form in the composition in dry form.

5. The composition of claim 4, wherein at least 35 wt. % of the total wt. of the composition in dry form is three, four, five, six, seven, or eight amino acid entities in (a)-(c) in one or both of free amino acid form or salt amino acid form.

6. The composition of claim 1, wherein:
   i) the wt. % of the BCAA entities is at least 37 wt. % of the total wt. of amino acid entities in the composition in dry form;
   ii) the wt. % of the UCAA entities is at least 25 wt. % of the total wt. of amino acid entities in the composition in dry form; or
   iii) the wt. % of the EAA entities is at least 16 wt. % of the total wt. of amino acid entities in the composition in dry form.

7. The composition of claim 1, wherein a wt. ratio of the BCAA entity or BCAA entities:the UCAA entity or UCAA entities:the EAA entity or EAA entities is 20+/−15%: 15+/−15%: 9+/−15%, where the ratios are determined based on an equivalent amount of each amino acid in free form.

8. The composition of claim 1, wherein three, four, five, six, or seven amino acid entities in (a)-(c) are selected as follows:
   i) the leucine amino acid entity is selected from: L-Leucine, Oxo-leucine (Alphaketoisocaproate (KIC)), HMB (betahydroxy-betamethylbutyrate), Isovaleryl-CoA, or N-Acetyl-Leucine;
   ii) the isoleucine amino acid entity is selected from: L-Isoleucine, 2-Oxo-3-methyl-valerate (Alpha-keto-betamethylvaleric acid (KMV)), Threonine, Methylbutyrl-CoA, or N-Acetyl-Isoleucine;
   iii) the valine amino acid entity is selected from: L-Valine, 2-Oxo-valerate (alphaketoisovalerate (KIV)), Isobutryl-CoA, or N-Acetyl-Valine;
   iv) the ornithine amino acid entity is selected from: L-ornithine or salt thereof, or citrulline;
   v) the aspartate amino acid entity is selected from: L-Aspartate, Fumarate, or Adenylosuccinate;
   vi) the histidine amino acid entity is selected from: L-Histidine, Histidinol, Histidinal, Ribose-5-phosphate, Carnosine, Histamine, Urocanate, or N-Acetyl-Histidine;
   vii) the lysine amino acid entity is selected from: L-Lysine, Diaminopimelate, Aspartate Trimethylhistidine, Carnitine, Saccharopine, N-Acetyl-Lysine, or L-Lysine Acetate; or
   viii) the threonine amino acid entity is selected from: L-Threonine, Homoserine, O-PhosphoHomoserine, Oxobutyrate, or N-Acetyl-Threonine.

9. The composition of claim 1, wherein the composition comprises:
   a) the leucine amino acid entity is chosen from:
      i) L-leucine or a salt thereof,
      ii) a dipeptide or salt thereof, or tripeptide or salt thereof, comprising L-leucine, or
      iii) β-hydroxy-β-methylbutyrate (HMB) or a salt thereof;
   b) one or both of:
      i) the ornithine amino acid entity is L-ornithine or a salt thereof or a dipeptide or salt thereof, or tripeptide or salt thereof, comprising L-ornithine; or
      ii) the aspartate amino acid entity is L-aspartate or a salt thereof or a dipeptide or salt thereof, or tripeptide or salt thereof, comprising L-aspartate; and
   c) the EAA entity is chosen from:
      i) L-histidine or a salt thereof,
      ii) a dipeptide or salt thereof, or tripeptide or salt thereof, comprising L-histidine,
      iii) L-lysine or a salt thereof,
      iv) a dipeptide or salt thereof, or tripeptide or salt thereof, comprising L-lysine,
      v) L-threonine or a salt thereof, or
      vi) a dipeptide or salt thereof, or tripeptide or salt thereof, comprising L-threonine.

10. The composition of claim 9, wherein the composition further comprises one or both of an isoleucine amino acid entity or a valine amino acid entity.

11. The composition of claim 10, wherein the isoleucine amino acid-entity is L-isoleucine or a salt thereof or a dipeptide or salt thereof, or tripeptide or salt thereof, comprising L-isoleucine.

12. The composition of claim 10, wherein the valine amino acid entity is L-valine or a salt thereof or a dipeptide or salt thereof, or tripeptide or salt thereof, comprising L-valine.

13. The composition of claim 10, wherein a wt. ratio of the leucine amino acid entity:the isoleucine amino acid entity:the valine amino acid entity:the ornithine amino acid entity:the aspartate amino acid entity:the histidine amino acid entity:the threonine amino acid entity:the lysine amino acid entity is 8+/−20%:4+/−20%:8+/−20%:7.5+/−20%: 7.5+/−20%:3+/−20%:3+/−20%:3+/−20%, where the ratios are determined based on an equivalent amount of each amino acid in free form.

14. The composition of claim 1, wherein the composition comprises: L-leucine or a salt thereof, L-isoleucine or a salt thereof, L-valine or a salt thereof, L-ornithine or a salt thereof, L-aspartate or a salt thereof, L-histidine or a salt thereof, L-threonine or a salt thereof, and L-lysine or a salt thereof.

15. The composition of claim 1, wherein the composition is formulated with a pharmaceutically acceptable carrier.

16. The composition of claim 1, wherein the composition is formulated as a dietary composition.

17. The composition of claim 1, wherein the composition comprises:
  (a) a leucine amino acid entity chosen from:
    (i) L-leucine or a salt thereof,
    (ii) a dipeptide or salt thereof, or tripeptide or salt thereof, comprising L-leucine, or
    (iii) β-hydroxy-β-methylbutyrate (HMB) or a salt thereof;
  (b) an isoleucine amino acid entity chosen from:
    (i) L-isoleucine or a salt thereof, or
    (ii) a dipeptide or salt thereof, or tripeptide or salt thereof, comprising L-isoleucine;
  (c) a valine amino acid entity chosen from:
    (i) L-valine or a salt thereof, or
    (ii) a dipeptide or salt thereof, or tripeptide or salt thereof, comprising L-valine;
  (d) an ornithine amino acid entity chosen from:
    (i) L-ornithine or a salt thereof,
    (ii) a dipeptide or salt thereof, or tripeptide or salt thereof, comprising L-ornithine,
    (iii) L-citrulline or a salt thereof, or
    (iv) a dipeptide or salt thereof, or tripeptide or salt thereof, comprising L-citrulline; and
  (e) an essential amino acid (EAA) entity chosen from:
    (i) L-histidine or a salt thereof,
    (ii) a dipeptide or salt thereof, or tripeptide or salt thereof, comprising L-histidine,
    (iii) L-lysine or a salt thereof,
    (iv) a dipeptide or salt thereof, or tripeptide or salt thereof, comprising L-lysine,
    (v) L-threonine or a salt thereof,
    (vi) a dipeptide or salt thereof, or tripeptide or salt thereof, comprising L-threonine, or
    (vii) or a combination of one, two, or three EAA entities, wherein:
  (f) the total weight (wt.) % of (a)-(e) is greater than the total wt. % of non-protein components or other protein components in the composition on a dry weight basis;
  (g) glutamine, if present, is present at less than 1 wt. % of the total wt. of the composition on a dry weight basis; and
  (h) two or three of phenylalanine, methionine, or tryptophan are absent from the composition.

18. The composition of claim 17, wherein the wt. % of the leucine amino acid entity, isoleucine amino acid entity, and valine amino acid entity is greater than the wt. % of the ornithine amino acid entity.

19. The composition of claim 17, wherein the wt. % of the leucine amino acid entity, isoleucine amino acid entity, valine amino acid entity, and ornithine amino acid entity is greater than the wt. % of the EAA or the combination or two or three EAAs.

20. The composition of claim 17, further comprising an aspartate amino acid entity chosen from L-aspartate or a salt thereof, or a dipeptide or salt thereof, or tripeptide or salt thereof, comprising L-aspartate; fumarate; adenylosuccinate; or a combination thereof.

21. The composition of claim 20, wherein a wt. ratio of the leucine amino acid entity:the isoleucine amino acid entity:the valine amino acid entity:the ornithine amino acid entity:the aspartate amino acid entity:the L-histidine or a dipeptide or salt thereof, or tripeptide or salt thereof, comprising L-histidine:the L-threonine or a salt thereof or a dipeptide or salt thereof, or tripeptide or salt thereof, comprising L-threonine:the L-lysine or a salt thereof or a dipeptide or salt thereof, or tripeptide or salt thereof, comprising L-lysine is 8+/−20%:4+/−20%:8+/−20%:7.5+/−20%:7.5+/−20%:3+/−20%:3+/−20%:3+/−20%, where the ratios are determined based on an equivalent amount of each amino acid in free form.

22. The composition of claim 1, wherein methionine is absent from the composition.

23. The composition of claim 1, wherein tryptophan is absent from the composition.

24. The composition of claim 1, wherein methionine and tryptophan are absent from the composition.

25. The composition of claim 1, wherein methionine, phenylalanine, and tryptophan are absent from the composition.

26. A composition comprising:
  a) a Branched Chain Amino Acid (BCAA) entity chosen from a leucine amino acid entity, an isoleucine amino acid entity, a valine amino acid entity, or a combination of two or three BCAA entities;
  b) a Urea Cycle Amino Acid (UCAA) entity chosen from an ornithine amino acid entity chosen from L-ornithine or salt thereof, citrulline, or a combination of either thereof; an aspartate amino acid entity; or a combination of two UCAA entities; and
  c) an essential amino acid (EAA) entity chosen from a histidine amino acid entity, a lysine amino acid entity, or a threonine amino acid entity or a combination of two or three EAA entities;
wherein:
  i) at least one amino acid entity of (a)-(c) is not provided as a peptide of more than 20 amino acid residues in length;
  ii) the total weight (wt.) % of (a)-(c) is greater than the total wt. % of non-protein components or other protein components in the composition on a dry weight basis;
  iii) two or more of phenylalanine, tyrosine, or glutamine is absent from the composition, or if present, is present at less than 1 wt. % of the total wt. of the composition on a dry weight basis; and
  iv) wherein a wt. ratio of the BCAA entity or BCAA entities:the UCAA entity or UCAA entities:the EAA entity or EAA entities is 20+/−15%: 15+/−15%: 9+/−15%, where the ratios are determined based on an equivalent amount of each amino acid in free form.

27. A composition comprising:
  (a) a leucine amino acid entity chosen from:
    (i) L-leucine or a salt thereof,
    (ii) a dipeptide or salt thereof, or tripeptide or salt thereof, comprising L-leucine, or
    (iii) β-hydroxy-β-methylbutyrate (HMB) or a salt thereof;

(b) an isoleucine amino acid entity chosen from:
  (i) L-isoleucine or a salt thereof, or
  (ii) a dipeptide or salt thereof, or tripeptide or salt thereof, comprising L-isoleucine;
(c) a valine amino acid entity chosen from:
  (i) L-valine or a salt thereof, or
  (ii) a dipeptide or salt thereof, or tripeptide or salt thereof, comprising L-valine;
(d) an ornithine amino acid entity chosen from:
  (i) L-ornithine or a salt thereof,
  (ii) a dipeptide or salt thereof, or tripeptide or salt thereof, comprising L-ornithine,
  (iii) L-citrulline or a salt thereof, or
  (iv) a dipeptide or salt thereof, or tripeptide or salt thereof, comprising L-citrulline; and
(e) an essential amino acid (EAA) entity chosen from:
  (i) L-histidine or a salt thereof,
  (ii) a dipeptide or salt thereof, or tripeptide or salt thereof, comprising L-histidine,
  (iii) L-lysine or a salt thereof,
  (iv) a dipeptide or salt thereof, or tripeptide or salt thereof, comprising L-lysine,
  (v) L-threonine or a salt thereof,
  (vi) a dipeptide or salt thereof, or tripeptide or salt thereof, comprising L-threonine, or
  (vii) or a combination of one, two, or three EAA entities, and
(f) an aspartate amino acid entity chosen from:
  (i) L-aspartate or a salt thereof, or a dipeptide or salt thereof, or tripeptide or salt thereof, comprising L-aspartate,
  (ii) fumarate,
  (iii) adenylosuccinate, or
  (iv) a combination thereof,
wherein:
  (g) the total weight (wt.) % of (a)-(f) is greater than the total wt. % of non-protein components or other protein components in the composition on a dry weight basis;
  (h) glutamine, if present, is present at less than 1 wt. % of the total wt. of the composition on a dry weight basis; and
  (i) a wt. ratio of the leucine amino acid entity:the isoleucine amino acid entity:the valine amino acid entity:the ornithine amino acid entity:the aspartate amino acid entity:the L-histidine or a dipeptide or salt thereof, or tripeptide or salt thereof, comprising L-histidine:the L-threonine or a salt thereof or a dipeptide or salt thereof, or tripeptide or salt thereof, comprising L-threonine:the L-lysine or a salt thereof or a dipeptide or salt thereof, or tripeptide or salt thereof, comprising L-lysine is 8+/−20%:4+/−20%:8+/−20%:7.5+/−20%:7.5+/−20%:3+/−20%:3+/−20%:3+/−20%, where the ratios are determined based on an equivalent amount of each amino acid in free form.

28. A composition comprising:
(a) L-leucine or a salt thereof;
(b) L-isoleucine or a salt thereof;
(c) L-valine or a salt thereof;
(d) L-ornithine or a salt thereof;
(e) L-histidine or a salt thereof;
(f) L-lysine or a salt thereof;
(g) L-threonine or a salt thereof; and
(h) L-aspartate or a salt thereof,
wherein:
  (h) the total weight (wt.) % of (a)-(h) is greater than the total wt. % of non-protein components or other protein components in the composition on a dry weight basis; and
  (i) two or three of phenylalanine, methionine, and tryptophan is absent from the composition.

29. The composition of claim 28, wherein the L-ornithine or a salt thereof is chosen from L-ornithine, L-ornithine L-aspartate (LOLA), ornithine α-ketoglutarate, or ornithine HCl.

30. The composition of claim 28, wherein the L-ornithine or a salt thereof in (d) and the L-aspartate or salt thereof in (h) are provided as L-ornithine L-aspartate (LOLA).

31. The composition of claim 28, wherein methionine, phenylalanine, and tryptophan are absent from the composition.

32. The composition of claim 1, wherein the L-ornithine or salt thereof is chosen from L-ornithine, L-ornithine L-aspartate (LOLA), ornithine α-ketoglutarate, or ornithine HCl.

33. The composition of claim 1, wherein the combination of two UCAA entities of b) comprises the ornithine amino acid entity and the aspartate amino acid entity.

34. The composition of claim 33, wherein the ornithine amino acid entity is L-ornithine or a salt thereof, and the aspartate amino acid entity is L-aspartate or a salt thereof.

35. The composition of claim 34, wherein the L-ornithine or a salt thereof and the L-aspartate or salt thereof are provided as L-ornithine L-aspartate (LOLA).

36. The composition of claim 26, wherein the combination of two UCAA entities of b) comprises the ornithine amino acid entity and the aspartate amino acid entity.

37. The composition of claim 36, wherein the ornithine amino acid entity is L-ornithine or a salt thereof, and the aspartate amino acid entity is L-aspartate or a salt thereof.

38. The composition of claim 37, wherein the L-ornithine or a salt thereof and the L-aspartate or salt thereof are provided as L-ornithine L-aspartate (LOLA).

39. The composition of claim 26, wherein the L-ornithine or salt thereof is chosen from L-ornithine, L-ornithine L-aspartate (LOLA), ornithine α-ketoglutarate, or ornithine HCl.

40. The composition of claim 27, wherein the ornithine amino acid entity comprises L-ornithine or a salt thereof and the aspartate amino acid entity comprises L-aspartate or a salt thereof.

41. The composition of claim 40, wherein the L-ornithine or a salt thereof and the L-aspartate or salt thereof are provided as L-ornithine L-aspartate (LOLA).

42. The composition of claim 27, wherein the L-ornithine or salt thereof is chosen from L-ornithine, L-ornithine L-aspartate (LOLA), ornithine α-ketoglutarate, or ornithine HCl.

* * * * *